US010786559B2

(12) United States Patent
Talaat et al.

(10) Patent No.: US 10,786,559 B2
(45) Date of Patent: *Sep. 29, 2020

(54) IMMUNOGENIC COMPOSITIONS AGAINST TUBERCULOSIS

(71) Applicant: Wisconsin Alumni Research Foundation, Madison, WI (US)

(72) Inventors: Adel M. Talaat, Madison, WI (US); Sarah K. Ward, Madison, WI (US); Bassam Abomoelak, Orlando, FL (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/914,172

(22) Filed: Mar. 7, 2018

(65) Prior Publication Data
US 2018/0177856 A1  Jun. 28, 2018

Related U.S. Application Data

(63) Continuation of application No. 14/950,197, filed on Nov. 24, 2015, now abandoned, which is a continuation of application No. 13/733,777, filed on Jan. 3, 2013, now Pat. No. 9,220,764, which is a continuation of application No. 12/800,374, filed on May 13, 2010, now Pat. No. 8,367,055.

(60) Provisional application No. 61/216,167, filed on May 14, 2009.

(51) Int. Cl.
A61K 39/40 (2006.01)
A61K 39/04 (2006.01)
A01N 63/00 (2020.01)
A61K 48/00 (2006.01)
C12N 1/36 (2006.01)
C12N 15/74 (2006.01)
C07K 14/35 (2006.01)
A61K 35/74 (2015.01)
C12N 15/86 (2006.01)
A61K 39/00 (2006.01)

(52) U.S. Cl.
CPC ............... *A61K 39/04* (2013.01); *C12N 1/36* (2013.01); *C12N 15/74* (2013.01); *A61K 35/74* (2013.01); *A61K 2039/522* (2013.01); *C07K 14/35* (2013.01); *C12N 15/86* (2013.01)

(58) Field of Classification Search
CPC .... C12N 15/86; C07K 16/1289; C07K 14/35; A61K 35/74
See application file for complete search history.

(56) References Cited

U.S. PATENT DOCUMENTS 7,393,539 B2   7/2008  James et al.
8,367,055 B2   2/2013  Talaat et al.
9,220,764 B2 * 12/2015 Talaat .................... A61K 39/04
2002/0068068 A1   6/2002  Mahan et al.
2005/0214754 A1   9/2005  Tyagi et al.
2005/0220811 A1  10/2005  Cole et al.
2006/0127897 A1   6/2006  Cole et al.
2006/0182685 A1   8/2006  Bishai et al.
2007/0082009 A1   4/2007  Lawrence et al.
2008/0199869 A1   8/2008  Fox et al.

FOREIGN PATENT DOCUMENTS

KR    10200479070    9/2004

OTHER PUBLICATIONS

Abonnoelak et al. (ASM 108th General Meeting, Jun. 4, 2008; Abstract U-056) (Year: 2008).*
Talaat et al., Journal of Bacteriology, 2007; 189(11): 4265-4274 (Year: 2007).*
Bidaut, Methods Mol. Biol., 2007; 408: 1-18 (Year: 2007).*
Pichichero (Human Vaccines, 2008; 4(4): 262-270) (Year: 2008).*
Abomoelak et al. (ASM 108th General Meeting, Jun. 4, 2008; Abstract U-056).
Abomoelak et al., mosR, a novel transcriptional regulator of hypoxia and virulence in *Mycobacterium tuberculosis,* J Bacteriology 191(19) 5941-5952, 2009, 12 pages.
Agarwal et al., Effects of copper on mammalian cell components. Chem Biol Interact 69: 1-16, 1989, 16 pages.
Aly et al., Oxygen status of lung granulomas in *Mycobacterium tuberculosis*-infected mice. J Pathol 210: 298-305, 2006, 8 pages.
Arruda et al., Cloning of an *M. tuberculosis* DNA fragment associated with entry and survival inside cells. Science 261: 1454-1457, 1993, 5 pages.
Avery et al., Copper toxicity towards *Saccharomyces cerevisiae* : dependence on plasma membrane fatty acid composition. Appl Environ Microbiol 62: 3960-3966, 1996, 7 pages.
Bardarov et al., Specialized transduction: an efficient method for generating marked and unmarked targeted gene disruptions in *Mycobacterium tuberculosis,* M. bovis BCG and M. smegmatis. Microbiology 148: 3007-3017, 2002, 11 pages.
Beisel et al., The impact of infectious disease on trace-element metabolism of the host. In Trace Element Metabolism in Animals-2. Hoekstra, W.G., Suttie, J.W., Ganther, H.E. And Mertz, W. (eds). Baltimore University Park Press: 217, 1974, 26 pages.
Betts et al., Evaluation of a nutrient starvation model of *Mycobacterium tuberculosis* persistence by gene and protein expression profiling Mol. Microbiol. 43: 717-731, 2002, 15 pages.
Bidaut, Methods Mol. Biol., 2007; 4008: 1-18.

(Continued)

Primary Examiner — Gary B Nickol
Assistant Examiner — Lakia J Jackson-Tongue
(74) Attorney, Agent, or Firm — Quarles & Brady LLP

(57) ABSTRACT

Methods of preparing mutants of *Mycobacterium tuberculosis* with one or more disrupted genes are presented, where the disrupted genes include ctpV, rv0990c, rv0971c, and/or rv0348. Compositions containing mutants with attenuated virulence and pathogenesis, which are capable of stimulation of an immune response against tuberculosis, are described. Compositions and methods relating to immunogenic compositions, which include an attenuated M. tb strain in which the M. tb genome includes a disruption of at least one of the ctpV gene, the rv0990c gene, the rv0971c gene, and the rv0348 gene, are also provided.

12 Claims, 28 Drawing Sheets
Specification includes a Sequence Listing.

(56) References Cited

OTHER PUBLICATIONS

Camus et al., Re-annotation of the genome sequence of *Mycobacterium tuberculosis* H37Rv. Microbiology 148: 2967-2973, 2002, 7 pages.
Casali et al., Regulation of the *Mycobacterium tuberculosis* mcel operon. Journal of Bacteriology 188: 441-449, 2006, 9 pages.
Casanova et al., Genetic dissection of immunity to mycobacteria: the human model. Annu Rev Immunol 20: 581-620, 2002, 42 pages.
Chung et al., Copper-induced ferroportin-1 expression in J774 macrophages is associated with increased iron efflux. Proc natl Acad Sci U S A 101: 2700-2705, 2004, 6 pages.
Cole et al., Deciphering the biology of *Mycobacterium tuberculosis* from the complete genome sequence. Nature 393: 537-538, 1998, 27 pages.
Corbett et al., The growing burden of tuberculosis—Global trends and interactions with the HIV epidemic. Arch.Intern.Med. 163: 1009-1021, 2003, 13 pages.
Cruz-Vera et al., Conserved Residues Asp16 and Pro24 of TnaC-tRNAPro Participate in Tryptophan Induction of tna Operon Expression. The Journal of Bacteriology 190: 4791-4797, 2008, 7 pages.
De Voss et al., The salicylate-derived mycobactin siderophores of *Mycobacterium tuberculosis* are essential for growth in macrophages. Proc Natl Acad Sci U S A 97: 1252-1257, 2000, 6 pages.
Espariz et al., Dissecting the *Salmonella* response to copper. Microbiology 153: 2989-2997, 2007, 9 pages.
Fleming et al., Induction of ceruloplasmin gene expression in rat lung during inflammation and hyperoxia. Am J Physiol 260: L68-74, 1991, 7 pages.
Francis et al., Mutants in the CtpA copper transporting P-type ATPase reduce virulence of Listeria monocytogenes. Microb Pathog 22: 67-78, 1997, 12 pages.
Gill et al., A replication clock for *Mycobacterium tuberculosis*. Nat Med advanced online publication, 2009, 11 pages.
Gold et al., Identification of a copper-binding metallothionein in pathogenic mycobacteria. Nat Chem Biol 4: 609-616, 2008, 8 pages.
Graubner et al., DnaK plays a pivotal role in Tat targeting of CueO and functions beside SlyD as a general Tat signal binding chaperone. J Biol Chem 282: 7116-7124, 2007, 9 pages.
Hu et al., Detection of mRNA transcripts and active transcription in persistent *Mycobacterium tuberculosis* induced by exposure to rifampin or pyrazinamide. J. Bacteriol. 182: 6358-6365, 2000, 8 pages.
International Search Report and Written Opinion for International Application No. PCT/US2010/001419, dated Feb. 9, 2011, 11 pages.
Kana et al., The resuscitation-promoting factors of *Mycobacterium tuberculosis* are required for virulence and resuscitation from dormancy but are collectively dispensable for growth in vitro. Mol. Microbiol 67: 672-684, 2008, 13 pages.
Kendziorski et al., On the utility of pooling biological samples in microarray experiments. Proc.Nat.Acad.Sci U.S.A 102: 4252-4257, 2005, 6 pages.
Kershaw et al., The expression profile of *Escherichia coli* K-12 in response to minimal, optimal and excess copper concentrations. Microbiology 151: 1187-1198, 2005, 12 pages.
Kim et al., 2002, ASM 102nd General Meeting, Abstract-Session No. 152/K-70.
Lillebaek et al., Molecular evidence of endogenous reactivation of *Mycobacterium tuberculosis* after 33 years of latent infection. The Journal of Infectious Diseases 185: 401-404, 2002, 4 pages.
Liu et al., CsoR is a novel *Mycobacterium tuberculosis* copper-sensing transcriptional regulator. Nat Chem Biol 3: 60-68, 2007, 9 pages.
Macomber et al., The iron-sulfur clusters of dehydratases are primary intracellular targets of copper toxicity. Proc Natl Acad Sci U S A 106: 8344-8349, 2009, 6 pages.
Macpherson et al., Type-2 copper-containing enzymes. Cell Mol Life Sci 64: 2887-2899, 2007, 13 pages.
Marrichi et al., Genetic toggling of alkaline phosphatase folding reveals signal peptides from all major modes of transport across the inner membrane of bacteria. J Biol Chem 283: 35223-35235, 2008, 13 pages.
Mayuri et al., Molecular analysis of the dormancy response in *Mycobacterium smegmatis*: expression analysis of genes encoding the DevR-DevS two-component system, Rv313c and chaperone alpha-crystallin homologues. FEMS Microbiol.Lett. 211: 231-237, 2002, 7 pages.
Meharg, Integrated tolerance mechanisms: constitutive and adaptive plant responses to elevated metal concentrations in the environment. Plant, Cell and Environment 17: 989-993, 1994, 3 pages.
Mitrakul et al., Role of a *Streptococcus gordonii* copper-transport operon, copYAZ, in biofilm detachment. Oral Microbiol Immunol 19: 395-402, 2004, 8 pages.
Muttucumaru et al., Gene expression profile of *Mycobacterium tuberculosis* in a non-replicating state. Tuberculosis 84: 239-246, 2004, 8 pages.
Notice of Allowance for U.S. Appl. No. 12/800,374, dated Oct. 5, 2012, 8 pages.
Office Action for U.S. Appl. No. 12/800,374, dated Feb. 16, 2012, 12 pages.
Office Action for U.S. Appl. No. 12/800,374, dated Jun. 19, 2012, 9 pages.
Office Action for U.S. Appl. No. 12/800,374, dated May 11, 2011, 17 pages.
Ohno et al., the effects of reactive nitrogen intermediates on gene expression in *Mycobacterium tuberculosis*. Cell Microbiol. 5: 637-648, 2003, 12 pages.
Ohsumi et al., Changes induced in the permeability barrier of the yeast plasma membrane by cupric ion. J Baceriol 170: 2676-2682, 1988, 7 pages.
Park et al., Rv3133c/dosR is a transcription factor that mediates the hypoxic response of *Mycobacterium tuberculosis*, 2003, 11 pages. Mol.Microbiol. 48: 833-843.
Pelicic et al., Efficient allelic exchange and transposon mutagenesis in *Mycobacterium tuberculosis*. Proc Natl Acad Sci U S A 94: 10955-10960, 1997, 6 pages.
Percival, Copper and immunity. Am J Clin Nutr 67: 1064S-1068S, 1998, 5 pages.
Pichichero (Human Vaccines, 2008; 4(4): 262:270).
Pinto et al., Heavy-metal induced oxidative stress in algae. Journal of Phycology 39: 1008-1018, 2003, 11 pages.
Rensing et al., CopA: An *Escherichia coli* Cu(I)-translocating P-type ATPase. Proc Natl Acad Sci U S A 97: 652-6, 2000, 5 pages.
Roback et al., A predicted operon map for *Mycobacterium tuberculosis*. Nucelic Acids Res. 35: 5085-5095, 2007, 11 pages.
Rodrigue et al., Identification of Mycobacterial {sigma} Factor Binding Sites by Chromatin Immunoprecipitation Assays. J. Bacteriol. 189: 1505-1513, 2007, 9 pages.
Rook et al., New insights into the immunopathology of tuberculosis. Pathobiology 59: 148-152, 1991, 5 pages.
Russell-Goldman et al., A *Mycobacterium tuberculosis* Rpf Double-Knockout Strain Exhibits Profound Defects in Reactivation from Chronic Tuberculosis and Innate Immunity Phenotypes. InfectAlmmun. 76: 4269-4281, 2008, 13 pages.
Rustad et al., The Enduring Hypoxic Response of *Mycobacterium tuberculosis*. PLoS ONE 3:e1502, 2008, 8 pages.
Sambrook et al., Molecular Cloning, a Laboratory Manual, Cold Spring Harbor Laboratory Press, Cold Spring Harbor, N. Y., 1989, 30 pages.
Sassetti et al., Genes required for mycobacterial growth defined by high density mutagenesis. Mol.Microbiol. 48: 77-84, 2003, 8 pages.
Schaible et al., Iron and microbial infection. Nat Rev Microbiol 2: 946-953, 2004, 9 pages.
Schnappinger et al., Transcriptional Adaptation of *Mycobacterium tuberculosis* within Macrophages: Insights into the Phagosomal Environment. J Exp Med 198: 693-704, 2003, 12 pages.
Schwan et al., Mutations in the cueA gene encoding a copper homeostasis P-type ATPase reduce the pathogenicity of Pseudomonas aeroginosa in mice. Int J Med Microbiol 295: 237-242, 2005, 6 pages.

(56) References Cited

OTHER PUBLICATIONS

Sherman et al., Regulation of the *Mycobacterium tuberculosis* hypoxic response gene encoding alpha-crystallin. Proc.Natl.Acad. Sci U.S.A. 98:7534-7539, 2001, 8 pages.

Sirakova et al., Identification of a diacylglycerol acyltransferase gene involved in accumulation of triacylglycerol in *Mycobacterium tuberculosis* under stress. Microbiology-(UK) 152:2717-2725, 2006, 17 pages.

Smith, I. (2003) *Mycobacterium tuberculosis* pathogenesis and molecular determinants of virulence. Clin Microbiol Rev 16: 463-496, 34 pages.

Stover et al., New use of BCG for recombinant vaccines. Nature 351: 456-460, 1991, 5 pages.

Talaat et al., (2007) Mycobacterial bacilli are metabolically active during chronic tuberculosis in murine lungs: Insights from genome-wide transcriptional profiling, J Bacteriol 189: 4265-4274, 10 pages.

Talaat et al., Copper transport and virulence in Mycobacterium tuberculosis. CtpV. Department of Pathobiological Sciences, University of Wisconsin-Madison. Madison, Wisconsin, U.S.A., 2010, 32 pages.

Talaat et al., Genome-directed primers for selective labeling of bacterial transcripts of DNA microarray analysis. Nat.Biotechnol. 18: 679-682, 2000, 4 pages.

Talaat et al., Genomic DNA standards for gene expression profiling in *Mycobacterium tuberculosis*. Nucleic Acids Res 30: e104, 2002, 9 pages.

Talaat et al., MosR, a novel virulence factor in *M. tuberculosis*. Department of Pathobiological Sciences, University of Wisconsin-Madison. Madison, Wisconsin, U.S.A. J. Bacteriol: 5941-5952, 2009, 12 pages.

Talaat et al., Mycobacterial bacilli are metabolically active during chronic tuberculosis in murine lungs: Insights from genome-wide transcriptional profiling. J.Bacteriol. 189: 4265-4274, 2007, 10 pages.

Talaat et al., The temporal expression profile of *Mycobacterium tuberculosis* infection in mice. Proc.Natl.Acad.Sci U.S.A. 101: 4602-4607, 2004, 6 pages.

Talaat et al., Transformation and transposition of the genome of *Mycobacterium marinum*. Am.J.Vet.Res. 61: 125-128, 2000, 4 pages.

Talaat, PowerPoint Presentation: Characterization of a novel pathogenicity island in *M. tuberculosis*. Laboratory of Bacterial Genomics, University of Wisconsin-Madison. Madison, Wisconsin, U.S.A., 2008, 11 pages.

Teitzel et al., Survival and growth in the presence of elevated copper: transcriptional profiling of copper-stressed Pseudomonas aeruginosa. J Bacteriol 188: 7242-7256, 2006, 15 pages.

Teixeira et al., The copper resistance operon copAB from Xanthomonas axonopodis pathovar citri: gene inactivation results in copper sensitivity. Microbiology 154: 402-412, 2008, 11 pages.

Timm et al., Differential expression of iron-, carbon-, and oxygen-responsive mycobacterial genes in the lungs of chronically infected mice and tuberculosis patients. Proc.Natl.Acad.Sci U.S.A. 100: 14321-14326, 2003, 6 pages.

Tsai et al., Characterization of the tuberculous granuloma in murine and human lungs: cellular composition and relative tissue oxygen tension. 2006, 15 pages.

Uchida et al., Accelerated immunopathological response of mice infected with *Mycobacterium tuberculosis* disrupted in the mcel operon negative transcriptional regulator. Cell Microbiol. 9: 1275-1283, 2007, 10 pages.

Voskuil et al., Inhibition of respiration by nitric oxide induces a *Mycobacterium tuberculosis* dormancy program. J. Exp. Med. 198: 705-713, 2003, 9 pages.

Voskuil et al., *Mycobacterium tuberculosis* gene expression during adaptation to stationary phase and low-oxygen dormancy. Tuberculosis 84:218-227, 2004, 10 pages.

Wagner et al., Elemental analysis of *Mycobacterium avium-*, *Mycobacterium tuberculosis-*, and *Mycobacterium smegmatis-* containing phagosomes indicates pathogen-induced microenvironments within the host cell's endomosmal system. J immonol 174: 1491-1500, 2005, 10 pages.

Waidner et al., Identification by RNA profiling and mutational analysis of the novel copper resistance determinants CrdA (HP1326), CrdB (HP1327)< and CzcB (HP1328) in Helicobacter pylori. J Bacteriol 184: 6700-8, 2002, 9 pages.

Wang et al., Structural and functional characterization of *Mycobacterium tuberculosis* CmtR, a PbII/CdII-sensing SmtB/ArsR metalloregulatory repressor. Biochemistry 44: 8976-8988, 2005, 13 pages.

Ward et al., CtpV: a putative copper exporter required for full virulence of *Mycobacterium tuberculosis*. CtpV. Department of Pathobiological Sciences, University of Wisconsin-Madison. Madison, Wisconsin, U.S.A. Molecular Microbiology 77: 1096-1110, 2010, 15 pages.

Ward et al., The global responses of *Mycobacterium tuberculosis* to physiological levels of copper. J.Bacteriol. 190: 2939-2946, 2008, 8 pages.

Wards et al., Electroporation at elevated temperatures substantially improves transformation efficiency of slow-growing mycobaceria. FEMS Microbiol.Lett. 145: 101-105, 1996, 5 pages.

Wayne et al., An in vitro model for sequential study of shiftdown of *Mycobacterium tuberculosis* through two stages of nonreplicating persistence of Infect.Immun. 64: 2062-2069, 1996, 8 pages.

White et al., Copper transport into the secretory pathway is regulated by oxygen in macrophages. J Cell Sci 122: 1315-1321, 2009, 7 pages.

Wu et al., A novel cell wall lipopeptide is important for biofilm formation and pathogenicity of *Mycobacterium avium* subspecies paratuberculosis. Microbial Pathogenesis 46: 222-230, 2009, 9 pages.

Wu et al., Defining the stressome of *Mycobacterium avium* subspecies paratuberculosis in vitro and in naturally infected cows. J. Bacteriol. 189: 7877-7886, 2007, 10 pages.

Yuan et al., The 16-kda alpha-crystallin (acr) protein of *Mycobacterium tuberculosis* is required for growth in macrophages. Proc Natl Acad Sci USA 95: 9578-9583, 1998, 6 pages.

Zhang et al., The Role of a P1-Type ATPase from Pseudomonas fluorescense SBW25 in copper homeostasis and plant colonization. Molecular plant-microbe interactions 20: 581-588, 2007, 8 pages.

Zhengwei et al., Hygromycin resistance gene cassettes for vector construction and selection of transformed rice protoplasts, 832-835, 1991, 4 pages.

\* cited by examiner

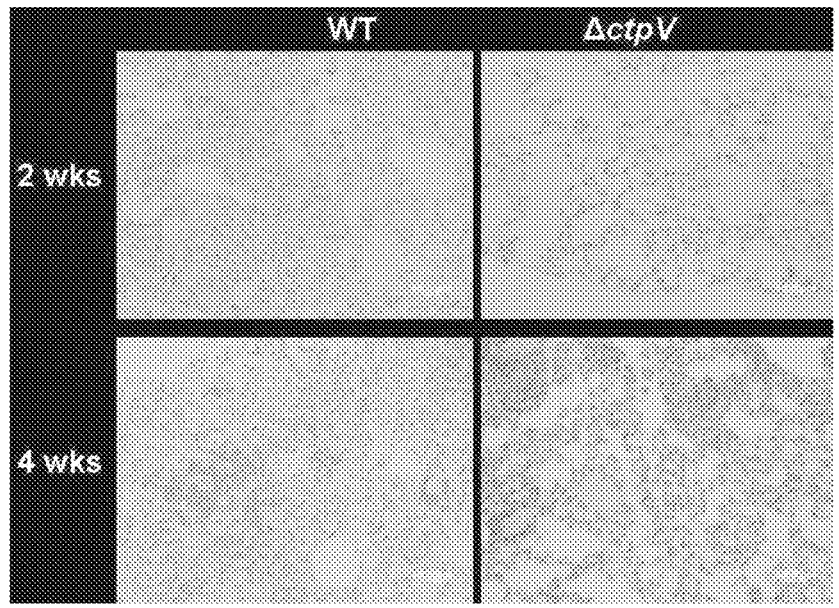
FIG. 11A  FIG. 11B
FIG. 11C  FIG. 11D
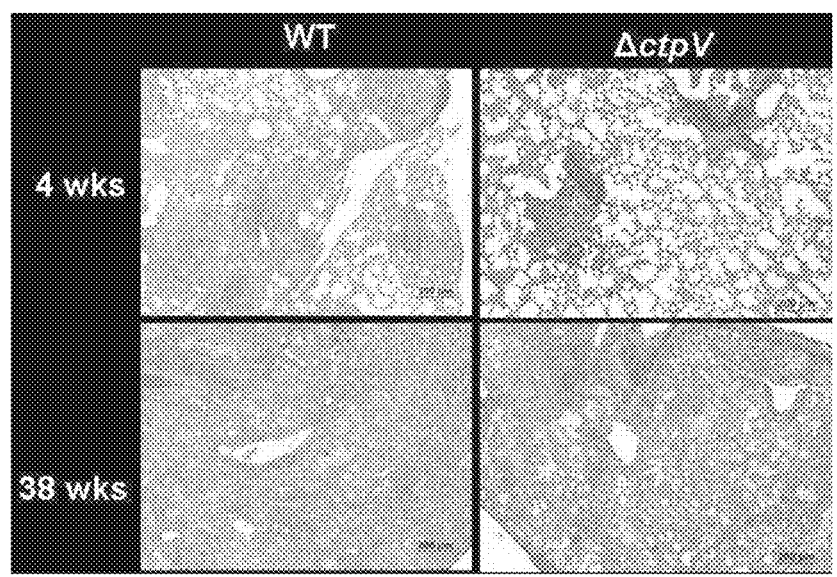
FIG. 12A  FIG. 12B
FIG. 12C  FIG. 12D

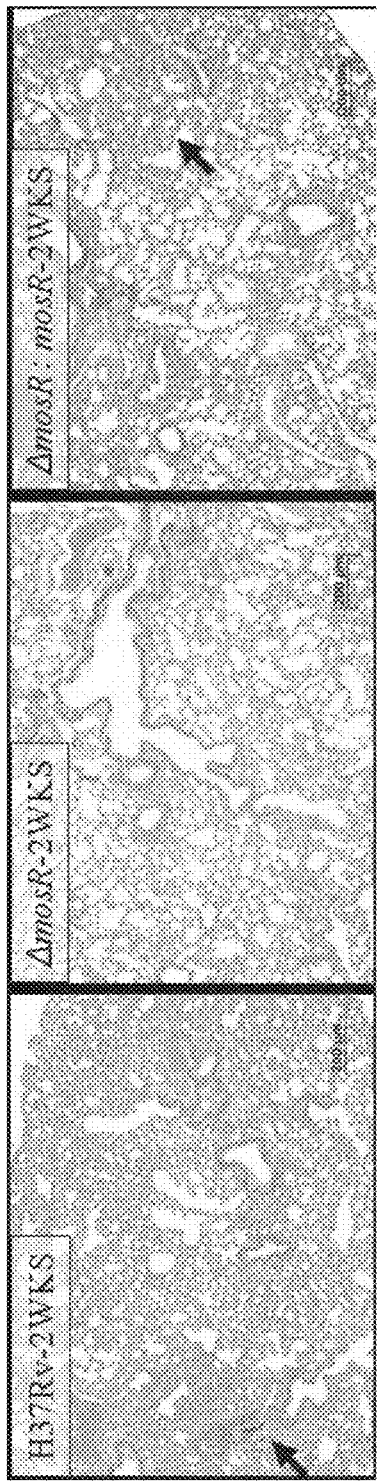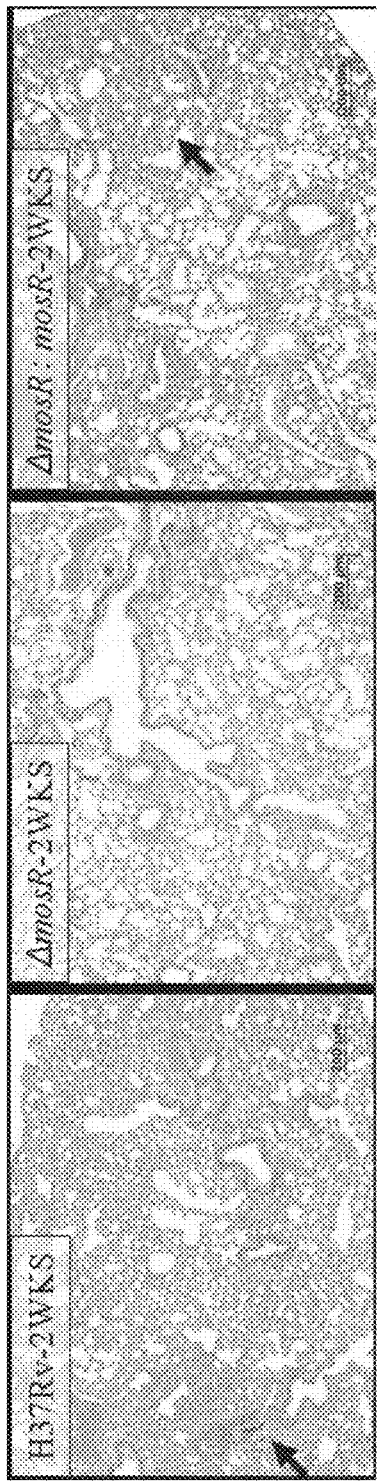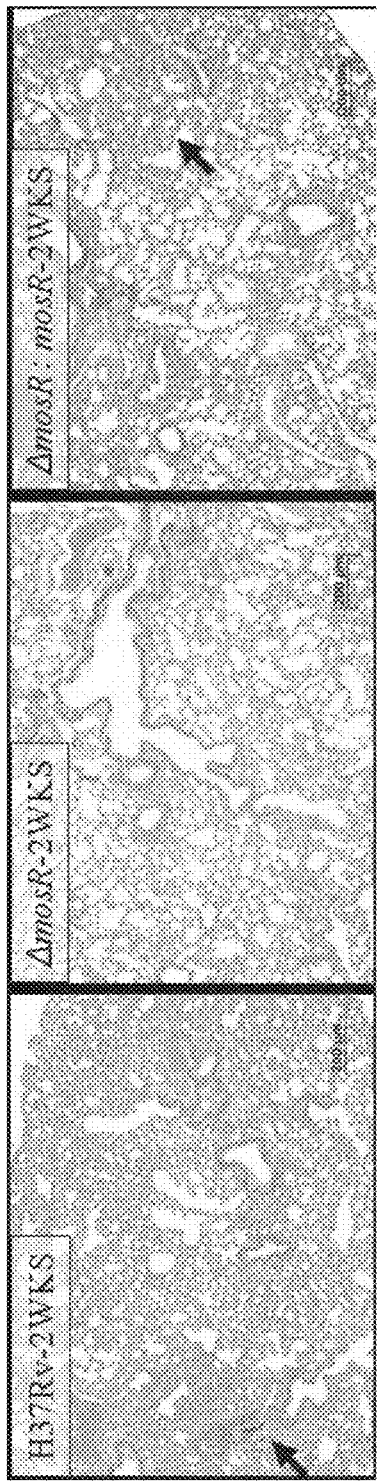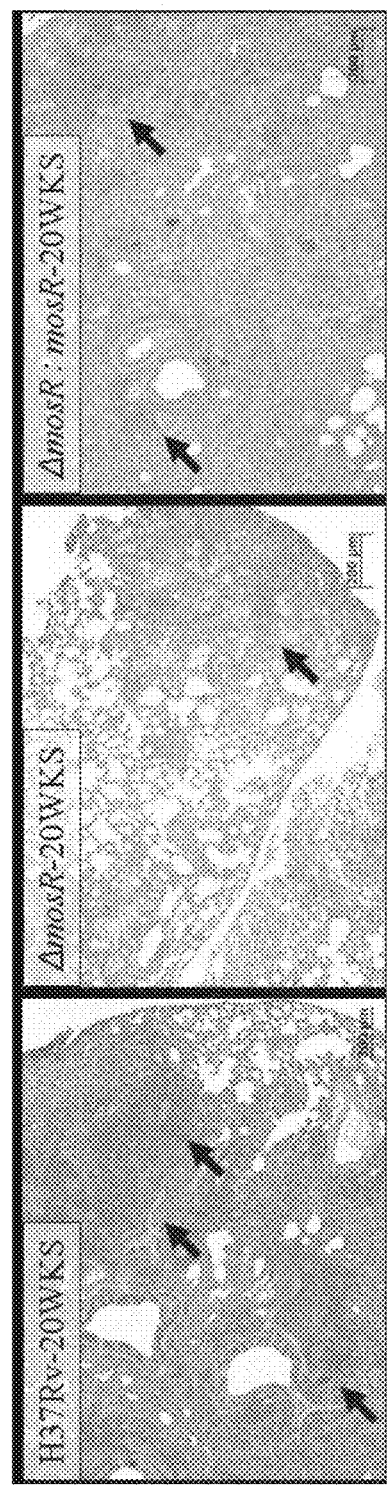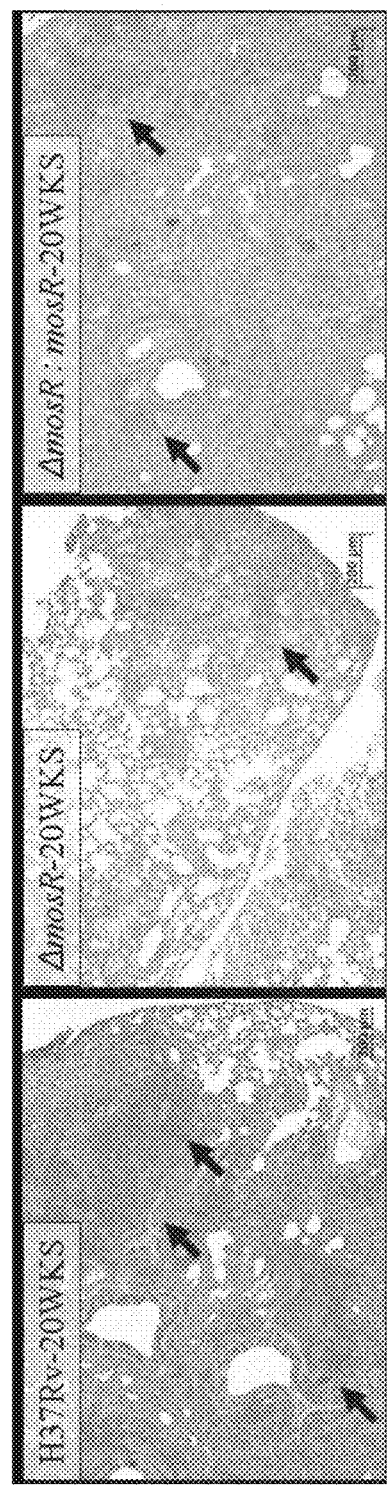
FIG. 20A  FIG. 20B  FIG. 20C  FIG. 20D  FIG. 20E  FIG. 20F

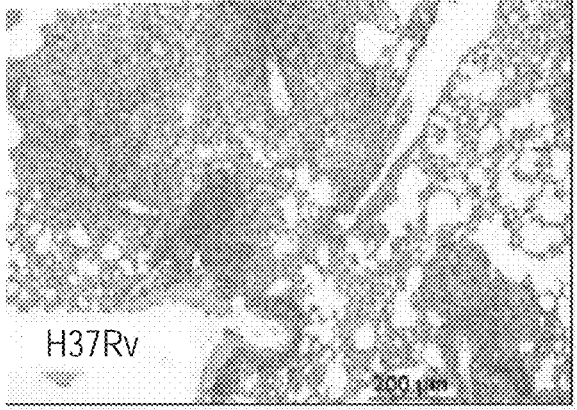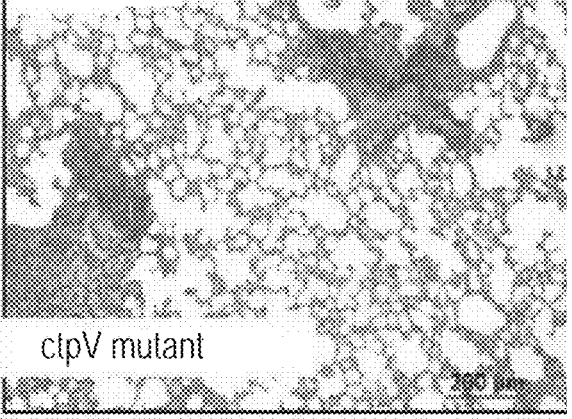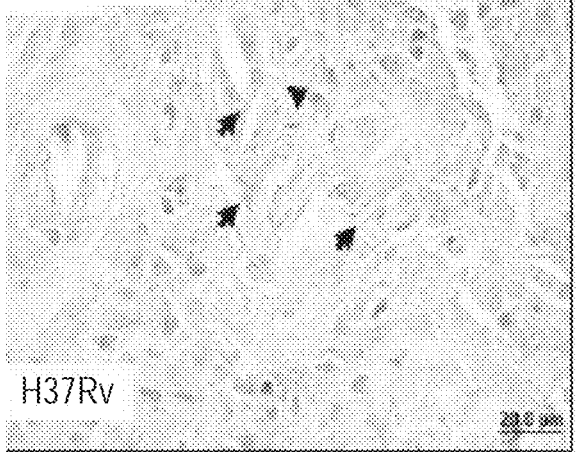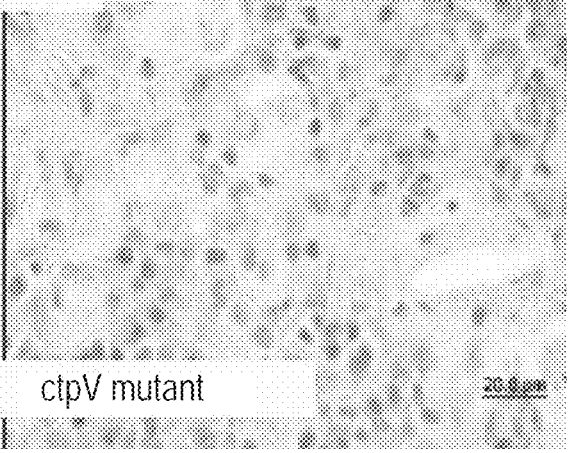

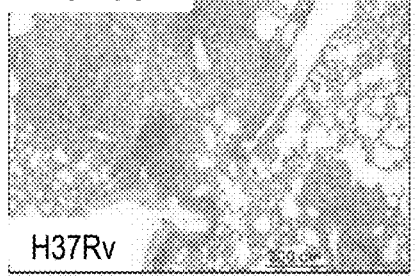
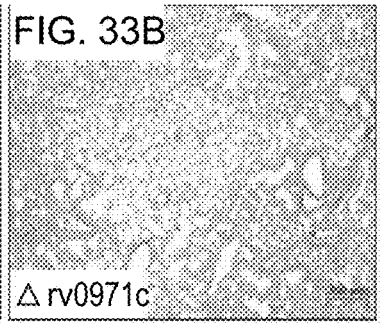
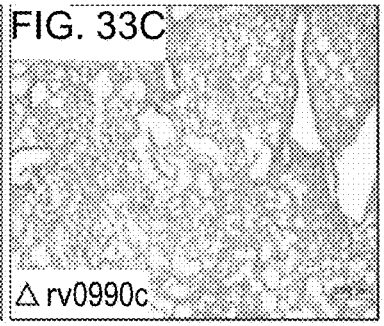
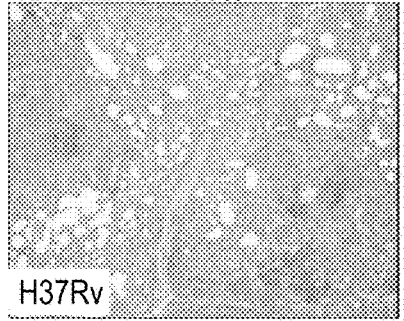
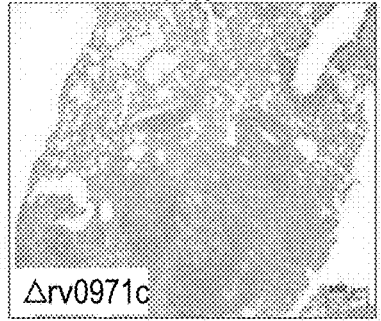
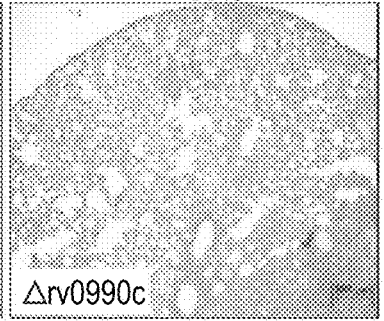
FIG. 33A  FIG. 33B  FIG. 33C
FIG. 33D  FIG. 33E  FIG. 33F
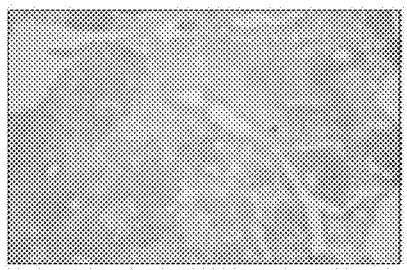
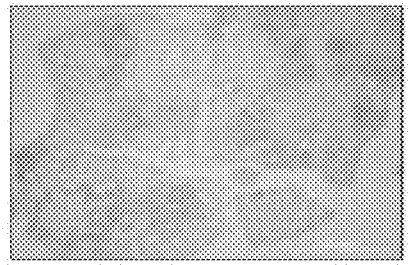
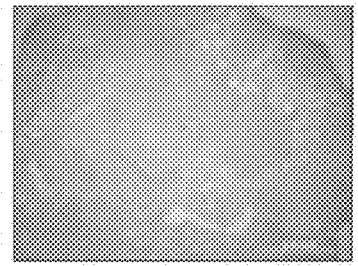
FIG. 34A  FIG. 34B  FIG. 34C

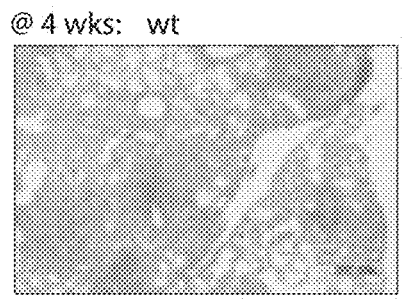 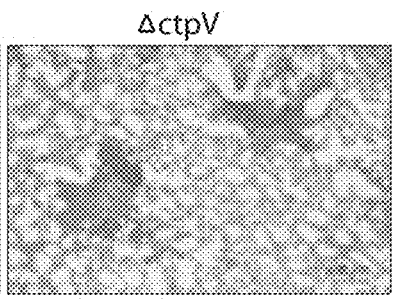 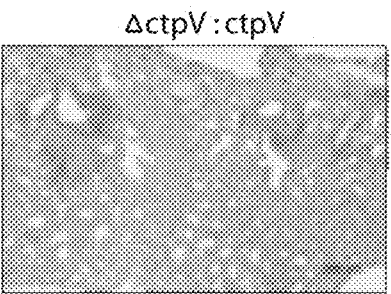
FIG. 36A @ 4 wks: wt
FIG. 36B ΔctpV
FIG. 36C ΔctpV:ctpV FIG. 39G H37Rv  FIG. 39H ΔctpV  FIG. 39I ΔctpV:ctpV

8 WKS

38 WKS

SEQUENCE LISTING

<160> NUMBER OF SEQ ID NOS: 110

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
atcactacta gttgaagacg gttcggggcc at                                   32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
atcactaagc ttataggcgt gcacggcgtg ca                32

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
atcacttcta gagggttctc ctcggtcagc gtg                33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
atcactggta cccagaaacg tccgccccgc tg                32

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gcgggtgtgg ttggccttgc cgtt                24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gcggcaacga tcgccgcacc gatg                24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tggtggacct cgacgacctg cagg                24

<210> SEQ ID NO 8

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acgaagcgcg cgaagggatg ctgg                                          24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggaactggcg cagttcctct gggg                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgaccgcaa agaagcgcgc ggcg                                          24

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acctcgaaca tggacac                                                  17

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
accggcaaac aactgatac                                                19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caatccaggg aaatgtca                                                 18

<210> SEQ ID NO 14
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agcttggtca gggact                                                       16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcgttgggca agtcat                                                       16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcttccgctt tgttct                                                       16

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aacccggtgg caaacaac                                                     18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgcagtggcc cacgaatg                                                     18

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccgtcctgga agcagtgaat g                                                 21

<210> SEQ ID NO 20
<211> LENGTH: 18
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 20
aaacgcacgg caccgaaa                                                    18

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gccgcacagt tcaacgaaac                                                  20

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgcaccagga ggcccaat                                                    18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agcacgatgc cgaagacctg                                                  20

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgcccggctg gtaattctg                                                   19

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtcgaggaac gaaaccatgc aat                                              23

<210> SEQ ID NO 26
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 26
accgtgtcta cgccgggaat                                                      20

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgcggcgatg aacgacat                                                        18

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acggcggcag aatcaccat                                                       19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gggtttctca aggcagaaga                                                      20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggatcgtcca cccatttg                                                        18

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aatccgccac catctatcag                                                      20

<210> SEQ ID NO 32
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 32
atctcaacgg acaggtgctc                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggacagaaga tccgcatcag                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cccgcgagtc cttgtactta                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
attctttcgc atgtgtgtgc                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaagatcaac agcaccgtca                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agcttgccga tctcaaactc                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cttctgccgg aggttctttc                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgatagatca accggaccac                                              20

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cattctgctc ctccgcagt                                               19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caacaaacga acctcggaat                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tactcaaatg cccacccttc                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcaagaatcc aaggcagagg                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgactcgttc acgctcaatc                                          20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gacttggtgg agtcgcagtt                                          20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccaatgaact gtgcggtatg                                          20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gggctcaaag cttctgtcac                                          20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tggtggccta gtggtttttc                                          20

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
actagtctac ccgggctggg aggagtttcg                               30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 50
aagcttgcaa agccgtagtc cgcgagctgc                                    30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tctagatggc gggacatcgc acgcgttgtc                                    30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggtaccaacg ggccaacggt gctgtcggag                                    30

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tcgcggacta cggctttg                                                 18

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccttgcgcca tttggtgatt g                                             21

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
atcctctaga atgaccattt cgttct                                        26

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
```

```
gcgcaagctt accgcttggg tcttat                                        26
```

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
aagaattcgt gcccggcgcg cgcgagttga cg                                 32
```

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
caccccgctc aagcttgcct cgac                                          24
```

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

```
ggggaattca tgaccatttc gttctctagc                                    30
```

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

```
tggaagcttt taccgcttgg gtcttatcga                                    30
```

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

```
cggtctagaa ttgagctccc tgggatggtg                                    30
```

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cggaagcttg gccgtcacaa cattcatgat aa        32

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cggaagcttg taaccgctgc ccgaac        26

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgcggatccc acaccacagc tgaggatca        29

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cggtctagac gggaagctcg caggtgg        27

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cggaagcttc tcccgcgagt ccttgtac        28

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cggtctagac gaagacctag gtgagttcct g        31

<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cggaagcttg agcgtgaaga tcaacagca        29

```
<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cgctctagac gggtcttgtt gtcgttggcg g                                          31

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cggaagcttc attgcgaagt gattcctccg g                                          31

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ttgtcgtgcc gaccgtcgcg gg                                                    22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ggagtccatc gcgccagctc ct                                                    22

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tcaacggcag caccacgtgg                                                       20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tgacccgatc gccgaaaccg                                                       20
```

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
acacagcgcc cggaatgcga                                           20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggaagcccgt acgggcaaga                                           20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtgtaggcaa ggtcgcggcg                                           20

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggctgcacgt ccttgtgtct acacc                                     25

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cagctcgaac gcgagttggc                                           20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aagccatgcc tagcgccgac                                           20

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
gaagacgagg agcaccggcg ct                 22

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
gtgcgcttgg gcgaccaggt ac                 22

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
tgcccaggct gccgggcaac g                  21

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
gcgcagtgat cggttcagcg ga                 22

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
gtctcttcgt tggccgagac gctgt              25

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
acccgccgac gacaccaaca cc                 22

<210> SEQ ID NO 87

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccacttgcac accgtccgac cg                                            22

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gaagcgtcag actaccggcc cg                                            22

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gtaaccgctg cccgaac                                                  17

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cacaccacag ctgaggatca                                               20

<210> SEQ ID NO 91
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cgggaagctc gcaggt                                                   16

<210> SEQ ID NO 92
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ctcccgcgag tccttgt                                                  17

<210> SEQ ID NO 93
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cgaagaccta ggtgagttcc tg                                              22

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gagcgtgaag atcaacagca                                                 20

<210> SEQ ID NO 95
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
atcactacta gtgatagcgt agcggagtca cc                                   32

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
atcactaagc ttagtgaccg ggtcgttttg gt                                   32

<210> SEQ ID NO 97
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
atcacttcta gaggtccagt ccgggcgcaa aa                                   32

<210> SEQ ID NO 98
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
atcactggta ccgaaccttg gctgccggaa gc                                   32

<210> SEQ ID NO 99
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 99
tggtggacct cgacgacctg cagg                                           24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gtggacagct tggccaaggt cggc                                           24

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gcacgctggg gactgctcga ac                                             22

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ggaactggcg cagttcctct gggg                                           24

<210> SEQ ID NO 103
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
atcactacta gtcaactcac tgcggttacg cc                                  32

<210> SEQ ID NO 104
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
atcactaagc ttatgctggc cttcctgcag aa                                  32

<210> SEQ ID NO 105
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 105
atcacttcta gagcggttgt gcggagagtt ca                                     32

<210> SEQ ID NO 106
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
atcactggta ccgactggat catcaagggc ca                                     32

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ggaactggcg cagttcctct gggg                                              24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gttctcctcg gtcagcgtgg tgac                                              24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tggtggacct cgacgacctg cagg                                              24

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
aagatcacca ccaccgcgcg tc                                                22
```

IMMUNOGENIC COMPOSITIONS AGAINST TUBERCULOSIS

CROSS-REFERENCE TO RELATED PATENT APPLICATIONS

This application is a continuation of U.S. patent application Ser. No. 14/950,197, filed Nov. 24, 2015; which is a continuation of U.S. patent application Ser. No. 13/733,777, filed Jan. 3, 2013, now U.S. Pat. No. 9,220,764, issued Dec. 29, 2015; which is a continuation of U.S. patent application Ser. No. 12/800,374, filed May 13, 2010, now U.S. Pat. No. 8,367,055, issued Feb. 5, 2013; which claims priority to U.S. Provisional Patent Application No. 61/216,167, filed May 14, 2009; each of the disclosures of which are expressly incorporated herein by reference in their entirety.

STATEMENT AS TO RIGHTS TO INVENTIONS MADE UNDER FEDERALLY SPONSORED RESEARCH OR DEVELOPMENT

This invention was made with government support under A1066235 awarded by the National Institutes of Health. The government has certain rights in the invention.

SEQUENCE LISTING

This application contains a Sequence Listing, which has been submitted via EFS-Web and is hereby incorporated by reference in its entirety. Said ASCII copy, created on Aug. 12, 2010, is named "99943825.txt" and is 25,188 bytes in size.

BACKGROUND

The *Mycobacterium tuberculosis* ("M. tb") genome is one of the largest bacterial genomes known, including more than 4 million base pairs and nearly four thousand predicted protein coding sequences. Approximately one-third of the world's population is infected with M. tb, the causative agent of the disease tuberculosis ("TB") in humans. Infection with M. tb is commonly the result of an uninfected person inhaling M. tb bacilli that have become airborne as a result of some action of an infected person, e.g., coughing, sneezing, spitting, or talking. Clinically, infection with M. tb in humans can be divided into three stages.

In the first stage of infection, which typically lasts from three to eight weeks, M. tb bacilli are taken up by alveolar macrophages in the lungs, where they multiply. In the second stage of the infection, which typically lasts from two to five months, M. tb multiplies within inactivated macrophages until they burst, whereupon M. tb circulates via the bloodstream to all body organs including the brain, bone marrow, and other parts of the lung. In the third stage of the infection, which typically lasts from six months to two years, the host commonly develops a cell-mediated immune response to M. tb and may experience pleurisy accompanied by severe chest pain. In the fourth stage of infection, there is either resolution of the primary complex or persistence of the infection until reactivation, which may occur many years after initial exposure to M. tb. While only 5-10% of non-immunocompromised persons exposed to TB develop active TB during their lives, it is estimated that each person with active TB infects about 10-15 others annually. Ultimately, TB causes nearly two million deaths every year and is a leading killer of HIV-infected persons.

A vaccine for tuberculosis, Bacille Calmette Guérin ("BCG"), prepared with an attenuated strain of the bovine pathogen *Mycobacterium bovis*, is routinely used worldwide. However, the vaccine utilizes bacteria that do not normally cause disease in humans and provides little to no protection against tuberculosis in adults. Drugs are also available to treat TB, but bacterial resistance has developed against every available drug. Moreover, multi-drug resistant ("MDR") and extensively drug-resistant ("XDR") strains of TB pose a serious threat to human health.

SUMMARY

The present application relates to M. tb mutants, which may exhibit reduced virulence in test subjects as compared to the counterpart wild-type M. tb. As a result of this reduced virulence, the mutants described herein may be useful for eliciting an immune response in a subject that has been exposed to the mutant. For example, in some embodiments, a pharmaceutically acceptable immunogenic composition comprising the M. tb mutants may be administered to a subject. The M. tb mutants described herein are commonly characterized by disruptions in the ctpV, rv0990c, rv0971c, and/or rv0348 (also known as "mosR") genes of M. tb.

For example, in some embodiments, engineered *Mycobacterium tuberculosis* ("M. tb") strains are provided in which the M. tb genome includes a disruption of at least one of the ctpV gene, the rv0990c gene, the rv0971c gene, and the rv0348 gene. In some embodiments, the disruption results in a knock-out of the disrupted gene; in other embodiments, the disrupted gene exhibits decreased expression of the corresponding gene product (i.e., RNA, protein). In further embodiments, the disruption prohibits the transcription of a full-length, wild-type mRNA and/or the production of a functional wild-type protein from the disrupted gene.

Gene disruptions may be generated by methods known in the art. For example, in some embodiments, the disruption includes an insertion of a heterologous sequence, such as a gene cassette, into the gene. In other embodiments, the disruption includes the replacement of at least a portion of the wild-type gene sequence with a heterologous sequence, such as a gene cassette. In some embodiments the heterologous sequence encodes a selectable marker, such as a hygromycin resistance gene.

In some embodiments, the engineered M. tb strains exhibit attenuated virulence. For example, in some embodiments, mice infected with the engineered M. tb strain have an increased average post-infection lifespan compared to mice infected with the corresponding wild-type strain. For example, in some embodiments, the post infection life span of mice infected with an engineered attenuated M. tb strain is at least about 125% compared to mice infected with the corresponding wild-type M. tb strain. In other embodiments, the post infection life span of mice infected with an engineered attenuated M. tb strain is at least about 125% to about 200% of that of mice infected with the corresponding wild-type M. tb strain. In other embodiments, the post infection life span of mice infected with an engineered attenuated M. tb strain is at least about 130% to about 190%; at least about 140% to about 180%; is at least about 150% to about 170%; is at least about 160% to about 165%; is at least about 162%; or at least about 138% of the post infection life span of mice infected with the wild-type strain. In some embodiments, the engineered attenuated M. tb strain is ΔctpV, Δrv0348, Δ0990c, or Δ0971c.

In some embodiments, the engineered M. tb strains exhibit a different response to stress as compared to the wild-type counterparts. For example, in some embodiments, the average lifespan of an engineered M. tb strain in 500 μM $CuCl_2$, is decreased by at least about 10% to about 50% as compared to a corresponding wild-type M. tb strain. In other embodiments, the lifespan of an engineered M. tb strain in 500 μM $CuCl_2$, is decreased by at least about 15% to about 40%; by at least about 20% to about 30%; or by at least about 25% as compared to a corresponding wild-type M. tb strain. In further embodiments, the engineered M. tb strains exhibit enhanced expression of hypoxia-related genes under low oxygen conditions as compared to the corresponding wild-type strains. In some embodiments, the engineered M. tb strain is Δrv0348.

In some embodiments, the engineered M. tb strains exhibit a different response to stress as compared to the wild-type counterparts. For example, in some embodiments, the engineered M. tb strains exhibit enhanced expression of hypoxia-related genes under low oxygen conditions as compared to the corresponding wild-type strains. In some embodiments, the expression of hypoxia-responsive genes under low-oxygen conditions is not repressed by an rv0348 protein. In some embodiments, the engineered M. tb strain is Δrv0348.

In further embodiments, the engineered M. tb strains exhibit enhanced expression of one or more of the following genes: Rv0823c-Rv0824c; Rv1622c; Rv1623c; Rv2031c; Rv2629-Rv2630; Rv3048c; and Rv3139-Rv3140. In other embodiments, the engineered M. tb strains exhibit decreased expression of one or more of the following genes: Rv0167-0177; Rv0684-0685; Rv0700-0710; Rv0718-0723; Rv1613-1614; Rv2391, 2392; Rv2948c; Rv3148-Rv3154; Rv3460c; Rv3824c-Rv3825c; Rv3921c-Rv3924c. In some embodiments, the engineered M. tb strain is Δrv0348.

The present disclosure also relates to immunogenic compositions including engineered M. tb strains. For example, in some embodiments, immunogenic compositions include an attenuated M. tb strain in which the M. tb genome includes a disruption of at least one of the ctpV gene, the rv0990c gene, the rv0971c gene, and the rv0348 gene. Some embodiments of immunogenic compositions also include a pharmaceutically acceptable carrier and/or a pharmaceutically acceptable adjuvant.

Also disclosed herein are methods of eliciting or stimulating an immune response in a subject against tuberculosis (e.g., vaccinating a subject against tuberculosis). In some embodiments, an immunogenic composition including an attenuated M. tb strain in which the M. tb genome includes a disruption of at least one of the ctpV gene, the rv0990c gene, the rv0971c gene, and the rv0348 gene is administered to the subject. In some embodiments, the subject is a mammal and the immunogenic composition is administered orally, nasally, subcutaneously, intravenously or by inhalation.

BRIEF DESCRIPTION OF THE DRAWINGS

FIG. 11A-D shows acid-fast staining of sectioned mouse lung tissue of mice infected with wild-type ("WT") and ΔctpV at two weeks (top A, B) and four weeks (bottom C, D) post infection.

FIG. 12A-D shows histological analysis of lung sections of mice lungs at 4 weeks (top A, B) and 38 weeks (bottom C, D) of infection with wild-type ("WT") and ΔctpV.

FIG. 20A-F shows histological analysis of lung sections of mice lungs at 2 weeks (A-C) and 20 weeks (D-F) after infection with H37Rv, Δrv0348 and Δrv0348::rv0348.

FIG. 32A-D shows histopathology of mouse tissue at 4 weeks post infection with ΔctpV (B, D) and the corresponding wild-type H37Rv M. tb strain (A, C).

FIG. 33A-F shows histopathology at early, chronic stages of mouse tissue at 4 weeks post infection with Δrv0971c, Δrv0990c (B, C, E, F) and the corresponding wild-type H37Rv M. tb strain (A, D).

FIG. 34A-C shows mouse lung tissue stained with IFN-γ antibody at 8 weeks post infection with wild-type and M. tb mutant strains. The left panel (A) shows mouse lung infected with wild-type M. tb, the middle panel (B) shows mouse lung infected with ΔctpV mutant, and the right panel (C) shows mouse lung infected with the ΔctpV:ctpV mutant.

FIG. 36A-C shows histological analysis of lung sections of mice lungs at 4 weeks post infection with wild-type ("WT") M. tb (A) and ΔctpV (B) and ΔctpV::ctpV (C).

FIG. 39A-L shows histological (A-F) and immunohistochemisty (G-L) analysis of lung sections of mice lungs at 8 (A-C and G-I) or 38 (D-F and J-L) weeks post infection with wild-type ("WT") M. tb and ΔctpV and ΔctpV::ctpV.

DETAILED DESCRIPTION

Figure 1:
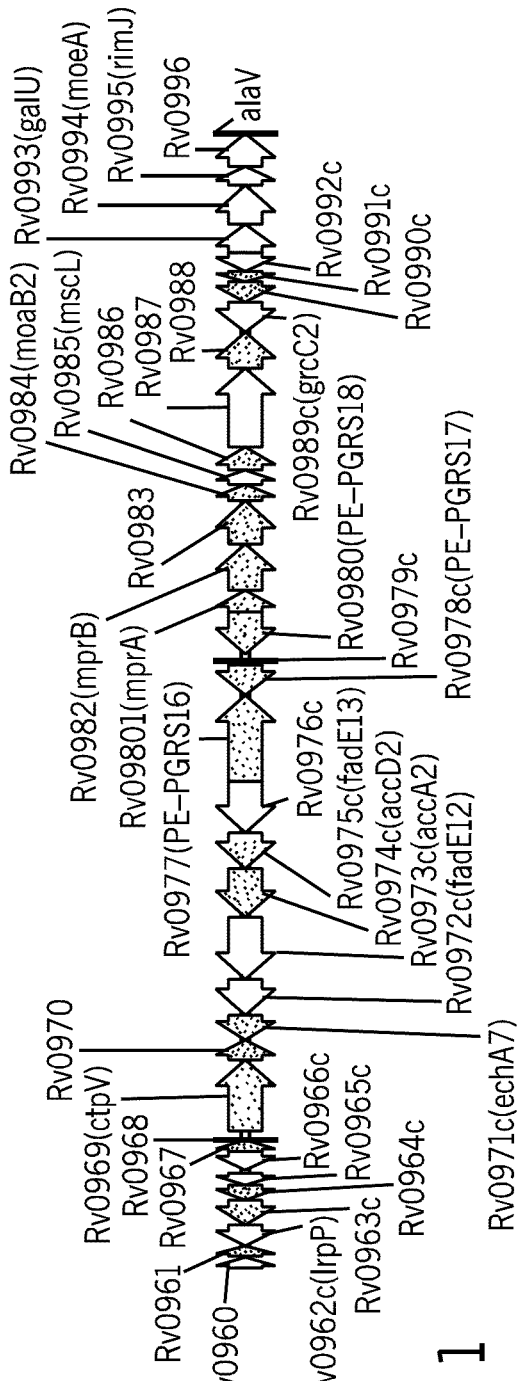
FIG. 1 shows a diagram of an in vivo expressed genomic island ("iVEGI") of M. tb preferentially expressed in murine host during tuberculosis.

The present application relates to novel M. tb mutants which exhibit reduced virulence in test subjects as compared to the wild-type M. tb counterpart. Due to the reduced virulence, the mutants described herein are useful for eliciting an immune response in a subject that has been exposed to the mutant. For example, in some embodiments, the mutants are provided as a pharmaceutically acceptable immunogenic compound, such as a vaccine.

The novel M. tb mutants described herein are characterized by disruptions in the ctpV, rv0990c, rv0971c, and/or rv0348 (also known as "mosR") genes of M. tb.

The present invention is described herein using several definitions, as set forth below and throughout the specification.

As used herein, the term "subject" refers to an animal, preferably a mammal, more preferably a human. The term "subject" and "patient" may be used interchangeably.

The term "pharmaceutically acceptable carrier" refers to any carrier that has substantially no long term or permanent detrimental effect when administered to an individual. Pharmaceutically acceptable carriers include diluents, fillers, salts, dispersion media, coatings, emulsifying agents, wetting agents, sweetening or flavoring agents, tonicity adjusters, absorption delaying agents, preservatives, antibacterial and antifungal agents, buffers, anti-oxidants, stabilizers, solubilizers, bulking agents, cryoprotectant agents, aggregation inhibiting agents, or formulation auxiliary of any type. Suitable carriers are described in Remington's Pharmaceutical Sciences (Remington's Pharmaceutical Sciences, 2000, 20th Ed., Lippincott, Williams & Wilkins), incorporated herein by reference. Preferred examples of such carriers or diluents include, but are not limited to, water, sodium chloride, mannitol, trehalose dihydrate, polysorbate 80, various pharmaceutically acceptable buffers for adjusting pH (e.g. phosphate buffers, citrate buffers, acetate buffers, and borate buffers).

The term "immunogenic composition" is used herein to refer to a composition that will elicit an immune response in a mammal that has been exposed to the composition. In some embodiments, an immunogenic composition includes at least one of four M. tb mutants ΔctpV, Δrv0990c, Δrv0971c, and/or Δrv0348. In some embodiments, the immunogenic composition includes at least two, at least three or at least four of the mutants ΔctpV, Δrv0990c, Δrv0971c, and/or Δrv0348.

In some embodiments, the immunogenic compositions described herein may be formulated for administration (i.e., formulated for "exposure" to the mammal) in a number of forms. For example, in some embodiments, the immunogenic compositions are prepared for oral, pulmonary, intravenous, intramuscular, subcutaneous, parenteral, nasal, or topical administration. Compositions may also be formulated for specific dosage forms. For example, in some embodiments, the immunogenic composition may be formulated as a liquid, gel, aerosol, ointment, cream, lyophilized formulation, powder, cake, tablet, or capsule. In other embodiments, the immunogenic composition is formulated as a controlled release formulation, delayed release formulation, extended release formulation, pulsatile release formulation, and mixed immediate release formulation. In some embodiments, the immunogenic composition is provided as a liquid. In other embodiments, the immunogenic composition is provided in lyophilized form.

The terms "mutation" and "disruption" are used interchangeably herein to refer to a detectable and heritable change in the genetic material. Mutations may include insertions, deletions, substitutions (e.g., transitions, transversion), transpositions, inversions and combinations thereof. Mutations may involve only a single nucleotide (e.g., a point mutation or a single nucleotide polymorphism) or multiple nucleotides. In some embodiments, mutations are silent, that is, no phenotypic effect of the mutation is detected. In other embodiments, the mutation causes a phenotypic change, for example, the expression level of the encoded product is altered, or the encoded product itself is altered. In some embodiments, a mutation may result in a disrupted gene with decreased levels of expression of a gene product (e.g., protein or RNA) as compared to the wild-type strain (e.g., M. tb). In other embodiments, a mutation may result in an expressed protein with activity that is lower as compared to the activity of the expressed protein from the wild-type strain (e.g., M. tb).

The term "knockout mutant" is used herein to refer to an organism in which a null mutation has been introduced in a gene. In a knockout mutant, the product encoded by the wild-type gene is not expressed, expressed at levels so low as to have no effect, or is non-functional. In some embodiment, the knockout mutant is caused by a mutation in the knocked out gene. In some embodiments, the knockout mutation is introduced by inserting heterologous sequences into the gene of interest. In other embodiments, the knockout mutation is introduced by replacing a portion of the wild-type gene or allele, or a majority of the wild-type gene or allele, with a heterologous sequence, or an engineered (e.g., manually altered, disrupted, or changed), non-functional, copy of the wild-type sequence.

A "knocked out gene" refers to a gene including a null mutation (e.g., the wild-type product encoded by the gene is not expressed, expressed at levels so low as to have no effect, or is non-functional). In some embodiments, the knocked out gene includes heterologous sequences or genetically engineered non-functional sequences of the gene itself, which renders the gene non-functional. In other embodiments, the knocked out gene is lacking a portion of the wild-type gene. For example, in some embodiments, at least about 10%, at least about 20%, at least about 30%, at least about 40% or at least about 60% of the wild-type gene sequence is deleted. In other embodiments, the knocked out gene is lacking at least about 70%, at least about 75%, at least about 80%, at least about 90%, at least about 95% or at least about 100% of the wild-type gene sequence. In other embodiments, the knocked out gene may include up to 100% of the wild-type gene sequence (e.g., some portion of the wild-type gene sequence may be deleted) but also include one or more heterologous and/or non-functional nucleic acid sequences inserted therein.

Generally, a heterologous sequence may be any sequence which does not affect the expression of other genes in the organism (e.g., does not encode a regulatory protein). Additionally, in some embodiments, a heterologous sequence includes a marker sequence (e.g., a gene that the organism does not have, and that confers resistance to a drug or other harmful agent, or that produces a visible change such as color or fluorescence). For example, in some embodiments, the heterologous sequence is the hygromycin resistance gene, as described in Bardarov, et al., 2002, *Microbiol.*, 148:3007-3017, herein incorporated by reference in its entirety. By way of example, but not by way of limitation, other suitable heterologous sequences include selectable markers such as a kanamycin resistance marker or other antibiotic resistance marker, β-galactosidase, or various other detectable markers known to those of skill in the art.

In a knockout mutant, the heterologous sequence may be expressed (e.g., may be transcribed and/or translated) or it may be silent (e.g., not transcribed and/or translated). For example, in the case of M. tb knockout mutants ΔctpV, Δrv0990c, Δrv0971c, and Δrv0348, the heterologous sequence includes the hygromycin resistance gene. The hygromycin resistance gene is expressed in the knockout mutants, and mutant knockouts are selected, inter alia, by virtue of their ability to grow in the presence of hygromycin.

Mutants, such as knockout mutants may be constructed using methods well known in the art, although methods involving homologous recombination are frequently used. In some embodiments, such methods include techniques such as electroporation or transduction. In other embodiments, transposons may be used to disrupt the gene of interests and insert heterologous sequence. By way of example, but not by way of limitation, other methods of constructing mutants in M. tb include, for example, the use of a suicide vector and chemical mutagenesis.

A knockout mutant may include a single knocked out gene or multiple knocked out genes. For example, in some embodiments, an M. tb knockout mutant includes a knock-out of one or more of the following genes: ctpV, rv0990c, rv0971c, and rv0348.

The term "M. tb ΔctpV," "ΔctpV mutant," "ΔctpV knockout," or "ΔctpV" is used herein to refer to an M. tb knockout, in which the ctpV gene is not expressed, expressed at levels so low as to have no effect or the expressed protein is non-functional (e.g., is a null-mutation). In some embodiments, the ΔctpV mutant includes a heterologous sequence in place of all or a majority of the ctpV gene sequence. In some embodiments, the heterologous sequence includes the hygromycin resistance gene.

The term "M. tb Δrv0990c," "Δrv0990c mutant," "Δrv0990c knockout" or "Δrv0990c" is used herein to refer to an M. tb knockout, in which the rv0990c gene is not expressed, expressed at levels so low as to have no effect or the expressed protein is non-functional (e.g., is a null-mutation). In some embodiments, the Δrv0990c mutant includes a heterologous sequence in place of all or a majority of the rv0990c gene sequence. In some embodiments, the heterologous sequence includes the hygromycin resistance gene.

The term "M. tb Δrv0971c," "Δrv0971c mutant," "Δrv0971c knockout," or "Δrv0971c" is used herein to refer to an M. tb knockout, in which the rv0971c gene is not expressed, expressed at levels so low as to have no effect or the expressed protein is non-functional (e.g., is a null-mutation). In some embodiments, the Δrv0971c mutant includes a heterologous sequence in place of all or a majority of the rv0971c gene sequence. In some embodiments, the heterologous sequence includes the hygromycin resistance gene.

The term "M. tb Δrv0348," "Δrv0348c mutant," "Δrv0348 knockout," "Δrv0384*," "M. tb* ΔmosR" "ΔmosR mutant," "ΔmosR knockout," or "ΔmosR" is used herein to refer to an M. tb knockout, in which the rv0348 gene is not expressed, expressed at levels so low as to have no effect or the expressed protein is non-functional (e.g., is a null-mutation). In some embodiments, the Δrv0348 mutant includes a heterologous sequence in place of all or a majority of the rv0348 gene sequence. In some embodiments, the heterologous sequence includes the hygromycin resistance gene. As used herein, the term rv0348 and mosR are used interchangeably.

The term "vaccine" is used herein to refer to a composition that is administered to a subject to produce or increase immunity to a particular disease. In some embodiments, vaccines include a pharmaceutically acceptable adjuvant and/or a pharmaceutically acceptable carrier.

The term "live attenuated vaccine" is used herein to refer to a vaccine prepared from live bacteria or viruses, which have been weakened so they produce immunity when exposed to a subject, but do not cause disease, or cause a less severe form, duration, onset or later onset of the disease.

In some embodiments, a live attenuated vaccine includes at least one of the four M. tb knockout mutants ΔctpV, Δrv0990c, Δrv0971c, and Δrv0348. In other live attenuated vaccine embodiments, at least two, at least three or at least four of the M. tb knockout mutants are provided. In still other embodiments, a live attenuated vaccine includes an M. tb knockout that includes multiple "knocked out" genes. For example, in some embodiments, the live attenuated vaccine includes M. tb with a knockout of one or more of the ctpV, rv0990c, rv0971c, and rv0348 genes.

In other embodiments, the "live attenuated vaccine" is a pharmaceutical composition that includes a pharmaceutically acceptable adjuvant and/or a pharmaceutically acceptable carrier.

The term "gene cassette" is used herein to refer to a DNA sequence encoding and capable of expressing one or more genes of interest (e.g., a selectable marker) that can be inserted between one or more selected restriction sites of a DNA sequence. In some embodiments, insertion of a gene cassette results in a disrupted gene. In some embodiments, disruption of the gene involves replacement of at least a portion of the gene with a gene cassette, which includes a nucleotide sequence encoding a selectable marker. In some embodiments, a gene cassette may be an antibiotic resistance gene cassette. In some embodiments, the antibiotic resistance gene cassette may be a hygromycin resistance cassette. By way of example, but not by way of limitation, Bardarov, et al., 2002, *Microbiol.*, 148:3007-3017 describes one embodiment of a hygromycin resistance gene cassette.

The term "engineered" is used herein to refer to an organism that has been deliberately genetically altered, modified, or changed, e.g. by disruption of the genome. For example, an "engineered M. tb strain" refers to an M. tb strain that has been deliberately genetically altered, modified, or changed.

The term "corresponding wild-type strain" or "parent wild-type strain" is used herein to refer to the wild-type M. tb strain from which the engineered M. tb strain was derived. As used herein, a wild-type M. tb strain is a strain that has not been engineered to knock out one or more of the ctpV, rv0990c, rv0971c, or rv0348 genes. The engineered M. tb strain may have been modified to knock out more than one of the ctpV, rv0990c, rv0971c, or rv0348 genes.

The term "pathogen" or "infectious agent" is used herein to refer to a specific causative agent of disease or illness in a host, such as, for example, a bacterium or virus.

The term "strain" is used herein to refer to a genetic variant of a organism, such as bacteria or virus. Thus, a wild-type M. tb strain is genetically different from a mutant M. tb strain.

The term "attenuated strain" is used herein to refer to a strain with weakened or reduced virulence in comparison to the corresponding wild-type strain.

The term "post-infection lifespan" ("PILS") is used herein to refer to the length of time an organism survives (i.e., lives) after infection with an infectious agent (e.g., an M. tb strain). As used herein, the PILS of an organism infected with a "standard" or "reference" infectious agent (e.g., a wild-type M. tb strain) is 100% when compared to the PILS of an organism infected with a "test" infectious agent (e.g., an engineered mutant strain of the "standard" or "reference" infectious agent). A PILS of greater than 100% indicates the organism infected with the test infectious agent lives longer than the organism infected with the reference infectious agent. A PILS of less than 100% indicates that the organism infected with the test infectious agent lives less long (i.e., dies sooner) than the organism infected with the reference infectious agent. In some embodiments, the "infected organism" is a mouse, and the infectious agent is an M. tb strain. In some embodiments, the "reference" M. tb strain is a wild-type M. tb strain and the "test" infectious agent is an engineered mutant of the wild-type M. tb strain.

The term "average post-infection lifespan" refers to the average time a group of organisms survives post-infection.

In some embodiments, the post-infection lifespan of organisms infected with different infectious agents (e.g., different strains of M. tb) are compared. For example, in some embodiments, the PILS of an organism (e.g., a mouse) infected with an engineered M. tb strain (i.e., "test" strain) is compared to the PILS of an organism (e.g., a mouse) infected with the corresponding wild-type strain of M. tb (i.e., the "reference" strain). In some embodiments, the average post-infection lifespan of organisms infected with different infectious agents (e.g., different strains of M. tb) are compared. For example, in some embodiments, the average PILS of mice infected with an engineered M. tb strain is compared to the average PILS of mice infected with the corresponding wild-type strain of M. tb. In some embodiments, the median post-infection lifespan of organisms infected with different infectious agents (e.g., different strains of M. tb) are compared. For example, in some embodiments, the median PILS of mice infected with an engineered M. tb strain is compared to the median PILS of mice infected with the corresponding wild-type strain of M. tb.

By way of example, but not by way of limitation, the median PILS of mice infected with a wild-type M. tb reference strain is 29 weeks. In comparison, mice infected with a mutant M. tb strain, (e.g., ΔctpV) have a median PILS of 47 weeks. In this example, the PILS of mice infected with the mutant M. tb is at least 62% greater than the PILS of mice infected with the wild-type M. tb reference strain. Thus, the PILS of the mice infected with the mutant M. tb is 162% of the PILS of mice infected with the wild type M. tb. As another non-limiting example, mice infected with mutant M. tb strain Δrv0348 live for at least 40 weeks, while mice infected with the corresponding wild-type M. tb strain have a median survival time of 29 weeks. Accordingly, the PILS of mice infected with the mutant M. tb strain is at least 138% of mice infected with the wild-type strain.

The term "virulence" is used herein to refer to the relative ability of a pathogen to cause disease.

The term "attenuated virulence" or "reduced virulence" is used herein to refer to a reduced relative ability of a pathogen to cause disease. For example, attenuated virulence or reduced virulence can describe bacteria or viruses that have been weakened so they produce immunity when exposed to a subject, but do not cause disease, or cause a less severe form, duration, onset or later onset of the disease.

The term "pathogenesis" is used herein to refer to the series of events leading up to a disease and the step-by-step development of the disease due to structural and/or functional changes to a cell, tissue, or organ caused by a pathogenic agent (e.g., bacterium, virus, chemical compound etc.).

The term "attenuated pathogenesis" is used herein to refer to a reduction in the number or severity of events leading up to a disease or a slowing of the development of a disease.

The term "adjuvant" is used herein to refer to a substance that enhances the pharmacological effect of a drug or increases the immune response to an antigen. By way of example, but not by way of limitation, adjuvants include mineral salts, e.g., aluminium hydroxide and aluminum or calcium phosphate gels; oil emulsions and surfactant based formulations, e.g., MF59 (microfluidised detergent stabilized oil-in-water emulsion), QS21 (purified saponin), AS02 [SBAS2] (oil-in-water emulsion+MPL+QS-21), Montanide ISA-51 and ISA-720 (stabilised water-in-oil emulsion); particulate adjuvants, e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), endogenous human immunomodulators, e.g., hGM-CSF or hIL-12 (cytokines that can be administered either as protein or plasmid encoded), Immudaptin (C3d tandem array); inert vehicles, such as gold particles.

As described above, the present application provides novel knockout mutants of *Mycobacterium tuberculosis* ("M. tb") useful in eliciting an immune response in a mammal against M. tb. The following examples are presented to illustrate 1) methods of producing knockout mutants, 2) methods of testing virulence of a knockout, and 3) methods of eliciting an immune response with the mutants. The examples are provided to assist one of ordinary skill in making and using the same. The examples are not intended in any way to otherwise limit the scope of the invention. The section is divided into eight main Examples: Example I provides information regarding the ΔctpV knockout mutant; Example II provides information regarding the Δrv0384 knockout mutant; Examples III provides information regarding a Δrv0990c knockout mutant; Example IV provides information regarding a Δrv0971c knockout mutant; Example V provides information regarding M. tb. infected mice; Example VI provides information regarding mice infected with a Δrv0990c mutant; Example VII provides information regarding mice infected with a Δrv0971c mutant; and Example VIII provides information regarding the use of M. tb mutants to generate an immune response and as vaccines.

Example I: ΔctpV Knockout Mutant

A. Overview

Many enzymes require a metal cofactor for activity. The metals that serve as cofactors in enzymes required for life are considered biologically active metals. These metals, including iron, copper, zinc, and magnesium, serve as required micronutrients for many diverse cellular organisms, from humans to bacteria. For bacteria that colonize the human body, this can serve as a form of environmental stress, as microbes and host cells struggle for the possession of the same micronutrients.

The most commonly used metal cofactor, iron, has frequently been studied in the context of this struggle. Required by both host cells and bacteria for a number of enzymatic activities, including respiration and detoxification, iron is kept bound by host proteins such as transferrin and lactoferrin. Successful human pathogens have developed compounds termed "siderophores" to compete with host proteins for bound iron. These microbes also use iron-specific uptake mechanisms and regulators which contribute to iron scavenging and survival within a host.

Another biologically active metal, copper, is also required by both host and bacterial enzymes, including oxidases and superoxide dismutase. The potential role of copper in host/microbe interactions has not yet been elucidated. Interestingly, studies of copper homeostasis mechanisms in pathogenic organisms have shown that copper export, as opposed to acquisition, seems to be most important for virulence. For example, copper export is required for full virulence of the human pathogens *Psuedomonas aeruginosa* and *Listeria monocytogenes* as well as the plant pathogen *Pseudomonas fluorescens*. Conversely, no copper importers or uptake mechanisms have been identified as required for virulence in any pathogen.

Studies of biometals indicate that although pathogenic bacteria must obtain sufficient amounts of micronutrients, they are also sensitive to metal toxicity. Therefore, an equal balance of metal import and export (homeostasis) must be obtained at levels appropriate for each metal. Presumably, the ability to sense metals in the environment and regulate the expression of homeostasis mechanisms is key to maintaining intracellular metals at appropriate concentrations.

The first copper-binding transcriptional regulator in *Mycobacterium tuberculosis* ("M. tb") was identified, and it has been demonstrated that this important human pathogen has the ability to respond to copper in its intracellular environment. As shown in FIG. 1, this copper-binding regulator, CsoR, is encoded within a region of the M. tb genome previously associated with in vivo survival, an in vivo expressed genomic island ("iVEGI") of M. tb preferentially expressed in murine host during tuberculosis. CsoR has been shown to upregulate the expression of its own operon, the cso operon, in response to increasing amounts of copper. The cso operon includes the ctpV gene, which encodes a putative metal transporter previously associated with copper response in M. tb.

Previously, the expression of the ctpV gene was determined to be induced by copper ions via the copper-binding transcriptional regulator CsoR. ctpV was identified as a member of the M. tb whole-genome transcriptional response to copper at both growth-permissive and toxic physiological levels, with highest induction occurring at toxic copper levels. Sequence analysis showed that ctpV has ~70% protein-level similarity to previously characterized copper transporters involved in copper export and import in *Escherichia coli* and *Enterococcus hirae*, respectively. Thus, due to its particularly high induction during exposure to toxic levels of copper, ctpV may encode a copper exporter required for detoxification in the presence of elevated copper.

In the following example, the role of ctpV in mycobacterial copper response and its relevance to the development of tuberculosis is shown. CtpV is a copper exporter required for copper homeostasis in M. tb. The CtpV copper exporter is also required for the full virulence of the bacteria in a mouse model of infection.

B. Construction of the ctpV Knockout Mutant

Figure 2:
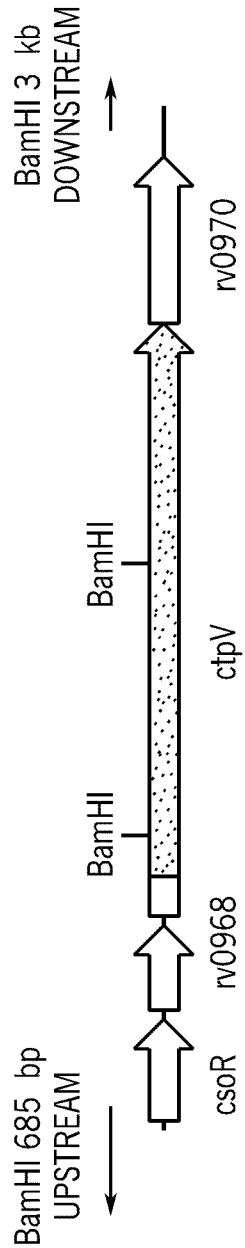
FIG. 2 is a representation of the ctpV coding region from which 2.1 kB are deleted (shown in black) to produce the ΔctpV mutant.
Figure 3:
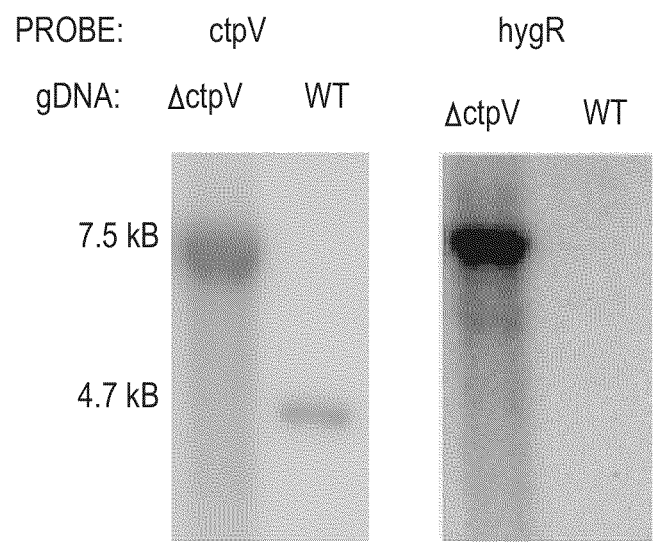
FIG. 3 shows Southern blot confirmation of the ΔctpV mutant.
Figure 4:
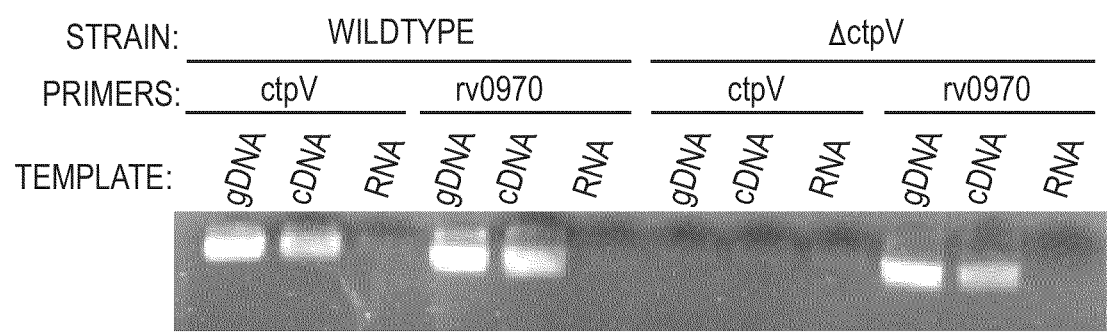
FIG. 4 shows the results of RT-PCR verifying transcription of ctpV and the downstream gene rv0970 in the wild-type strain but only transcription of the rv0970 gene in the isogenic mutant ΔctpV.
Figure 5:
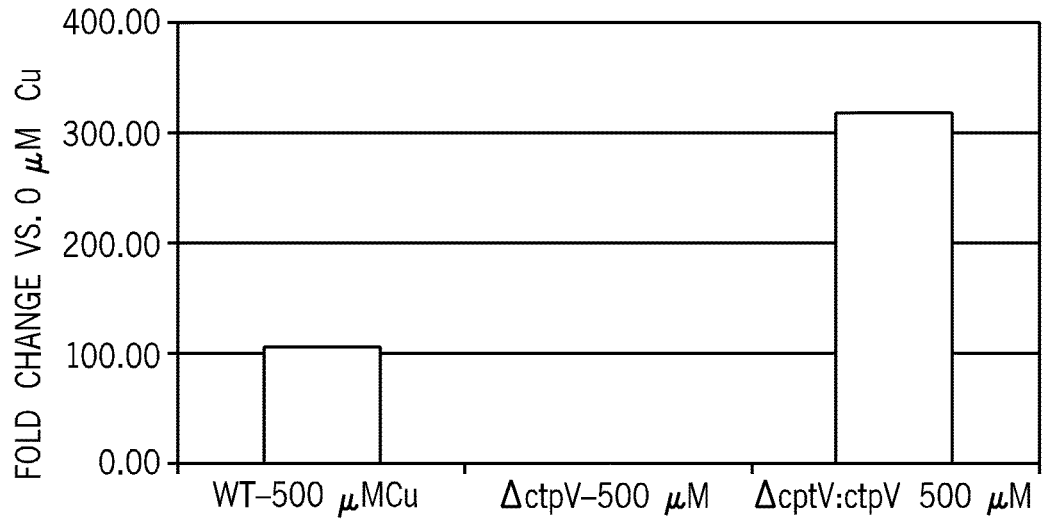
FIG. 5 shows the fold changes in expression of ctpV in H37Rv and isogenic mutants after exposure to 500 μM copper relative to cultures kept copper-free.
Figure 6:
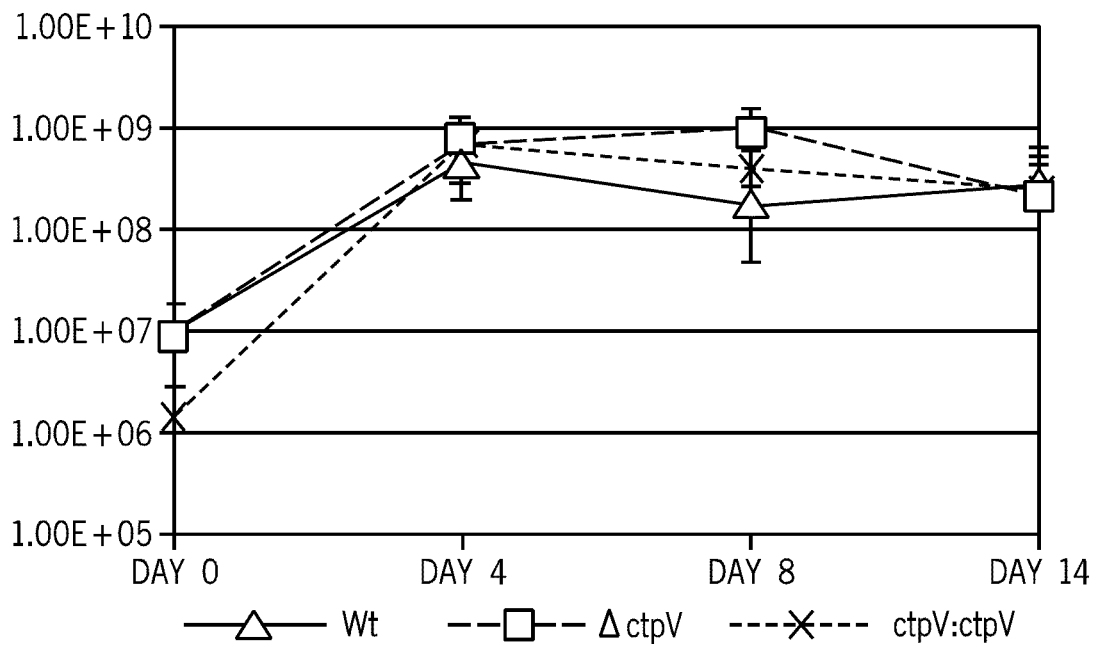
FIG. 6 shows growth curves of wild-type M. tb, its isogenic mutant ΔctpV, and the complemented strain ΔctpV:ctpV.

A knockout mutant of ctpV, ΔctpV, was created in the virulent M. tb strain H37Rv by replacing the coding region of ctpV with a hygromycin resistance cassette using homologous recombination. Referring to FIG. 2, the ΔctpV mutant was created with homologous recombination via pML21, a derivative of pPR27, which resulted in the deletion of 2.1 kB of the ctpV coding region (represented in black) and the insertion of a 3.5 kB region encoding a hygromycin resistance cassette. The ctpV gene is 2313 base pairs long. About 2.1 kB of the coding sequence of ctpV (base 102 to 2239) were deleted from the genome of M. tb and replaced by the hygromycin cassette.

Briefly, to construct ΔctpV, 800 basepair fragments of both the upstream and downstream portion of the gene were amplified by PCR (primers AMT567, AMT568, AMT371, and AMT372 are listed in Table 3). The amplified fragments were cloned into the pGEM-T Easy vector (Promega, Madison, Wis.). The fragments were digested with the flanking restriction enzyme sites (AflII/XbaI and HindIII/SpeI for upstream and downstream portions, respectively) and ligated into pYUB854. After digestion by NotI and SpeI (Promega), the linearized vector was ligated into pML19, a derivative of pPR27 where a kanamycin resistance cassette has been inserted into the PstI site. The resulting vector was named "pML20".

This vector was electroporated into electrocompetent M. tb using a Gene Pulser II machine (BioRad, Herculese, Calif.), and cells were plated onto Middlebrook 7H10 supplemented with 10% albumin-dextrose-catalase (ADC) and 50 ug/mL hygromycin (Invitrogen, Carlsbad, Calif.). After one month of growth at 32° C., transformants were grown for two weeks with shaking at 32° C. in Middlebrook 7H9 supplemented with 10% ADC and 50 ug/mL hygromycin. These cultures were plated onto Middlebrook 7H10 supplemented with 10% ADC, 2% sucrose, and 50 ug/mL hygromycin and incubated at 39° C. for three weeks. The genomic incorporation of the plasmid was confirmed via the inability of colonies to grow on Middlebrook 7H10 supplemented with 25 ug/mL kanamycin.

The transformant used for experiments, ΔctpV, was confirmed via negative PCR for the ctpV coding region and positive PCR for the hygromycin resistance cassette with primers listed in Table 3, AMT885, AMT886, AMT887, and AMT926.

Additionally, Southern blot analysis was performed on ΔctpV and wild type genomic DNA (5 μg) digested with BamHI (Promega), using probes for the remaining coding region of ctpV or the hygromycin resistance cassette. Referring to FIG. 3, the mutant was confirmed with Southern blots using a membrane constructed from BamHI-digested genomic DNA for WT or ΔctpV. Incubation with a P-32 labeled probe for the remaining ctpV region (FIG. 3, left) revealed the increased size of the band in ΔctpV resulting from the loss of two BamHI restriction enzyme sites within the ctpV coding region, as shown in FIG. 2, when it was replaced with HygR, which contains no BamHI sites. Additionally, a probe for the hygromycin resistance cassette (FIG. 3, right) hybridized only to the mutant gDNA.

Because ctpV is the third gene in the 4-gene cso operon, ΔctpV was tested for possible polar effects on the downstream gene of unknown function, rv0970. Using reverse-transcriptase PCR, the transcription of rv0970 in the mutant strain was confirmed. Referring to FIG. 4, the polarity of the ctpV knockout mutant was addressed using RT-PCR to check for transcription of its downstream gene. In the wild-type strain (left), positive bands show that ctpV and the downstream gene rv0970 are both encoded in the genome and transcribed (able to be amplified from cDNA), with negative amplification from RNA shown as a negative control. In the isogenic mutant ΔctpV (right), the ctpV coding region is not present in the genome nor is it transcribed, but the downstream gene rv0970 is unaffected.

C. Construction and Evaluation of a ctpV Complement

A complemented strain was created by cloning the ctpV coding region into an integrative vector (pMV361) containing the constitutive hsp60 promoter and transforming into the ΔctpV mutant strain. Integration of ctpV into the ΔctpV genome to create the complemented strain ΔctpV:ctpV was confirmed with PCR, and restored gene expression was confirmed with qRT-PCR.

Briefly, for complementation of ΔctpV, the ctpV coding region was amplified and cloned into the pGEM-T easy vector for sequencing. The pGEM vector was then digested with EcoRI and HindIII (Promega), and the fragment was ligated into pMV361. The vector was sequenced, and then electroporated into electrocompetent ΔctpV cells and plated on 7H10 supplemented with 10% ADC with 50 ug/mL hygromycin and 25 ug/mL kanamycin. The complemented strain was confirmed using a forward primer within the pMV361 vector (hsp60) and a reverse primer within the ctpV coding region.

D. Evaluation of ΔctpV, Complement ΔctpV:ctpV and Wild-Type M. tb Strain H37Rv

Referring to FIG. 5, expression of ctpV was measured using qRT-PCR, with cDNA created from 30 mL cultures exposed to 500 μM Cu. Data is expressed as fold-change relative to cultures kept copper-free, a condition in which expression from the cso operon is minimal. qRT-PCR did not detect expression of ctpV in the knockout mutant (middle), but expression was restored in the complemented strain (right). The higher level of induction in the complemented strain relative to WT H37Rv (left) is indicative of the increased strength of the hsp60 promoter used for complementation relative to the native cso promoter.

A growth curve in 7H9 media revealed that ΔctpV and its complement ΔctpV:ctpV have no generalized growth defects relative to WT. Referring to FIG. 6, growth curves of WT, its isogenic mutant ΔctpV, and the complemented strain ΔctpV:ctpV were performed in 7H9+ADC. 7H9 media was prepared using Remel brand 7H9 Middlebrook powder, prepared as described by manufacturer. 10% ADC supplementation consisted of adding 100 mL containing 2 grams glucose, 5 grams BSA fraction V, and 0.85 grams NaCl to 900 mL 7H9 media. Cultures were seeded from stock to OD 0.10 and allowed to grow for 14 days at 37° with shaking, with CFUs taken at 0, 4, 8, and 14 days via plating on 7H10+ADC. The data show an identical growth rate among the three strains. Two biological replicates were performed.

CsoR is induced proportionally to intracellular copper concentration. The ΔctpV mutant shows increased expression of csoR at 500 μM copper as compared to wild-type, while the ΔctpV:ctpV mutant shows decreased expression of csoR at 500 μM copper. (See FIG. 35).

The ΔctpV mutant and the complemented strain ΔctpV:ctpV were then used to experimentally characterize the role of ctpV in copper response.

E. ctpV Expression is Required for Optimal Survival in High Copper

To test the role of ctpV in copper transport, copper sensitivity between ΔctpV and wild-type H37Rv M. tb ("WT") were compared. The knockout of a copper exporter would be expected to result in increased sensitivity to copper-based toxicity, and this phenotype has been observed in knockouts of previously characterized copper exporters in other organisms. To test the copper sensitivity phenotype of ΔctpV, growth curves of WT and ΔctpV in liquid broth cultures supplemented with defined amounts of copper were performed using a range of copper concentrations previously determined to be physiologically relevant.

Growth curves were performed in 30 mL Cu-free Sauton's minimal media+0.05% Tween, prepared using water treated with Chelex (Sigma-Aldrich, St Louis, Mo.), with defined amounts of $CuCl_2$ added. Glassware was acid-washed (1N nitric acid) to maintain metal-free conditions.

Cultures were seeded to OD 0.1 with bacterial stock washed 2× in Sauton's, and allowed to grow for 14 days at 37° C. with shaking. Colony forming units ("CFUs") were determined at 0, 4, 8, and 14 days post-exposure by plating on Middlebrook 7H10+10% ADC, with 50 ug/mL hygromycin added in the case of the mutant and complemented strains.

Figure 7:
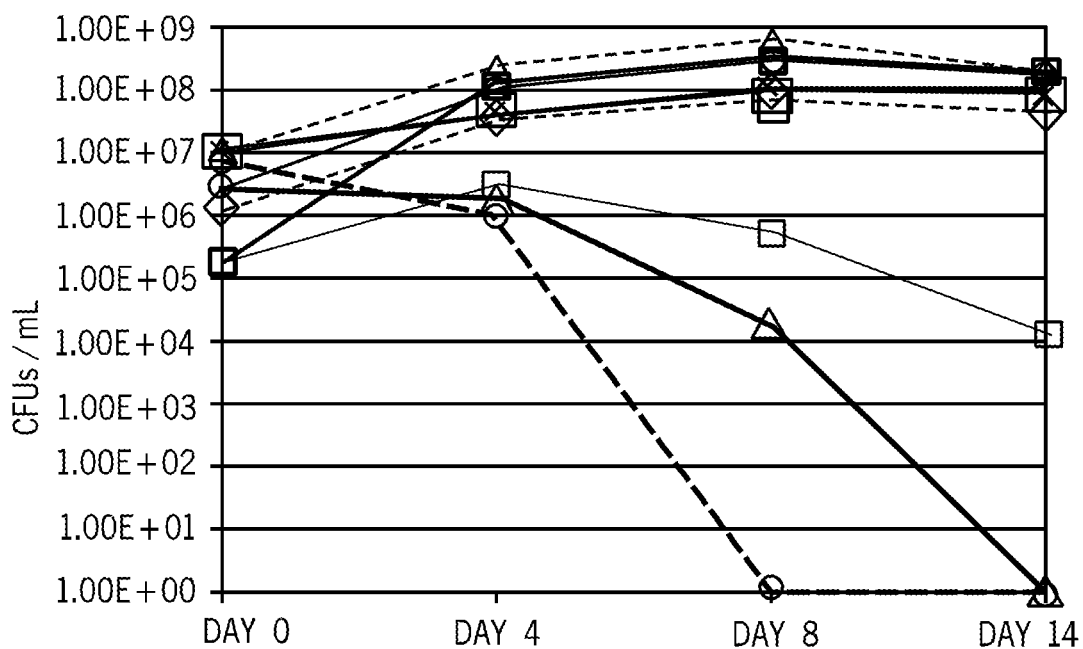
FIG. 7 shows growth curves of wild-type M. tb (H37Rv), its isogenic mutant ΔctpV, and the complemented strain ΔctpV:ctpV in the presence of 0 μM and 50 μM and 500 μM $CuCl_2$.
Figure 8:
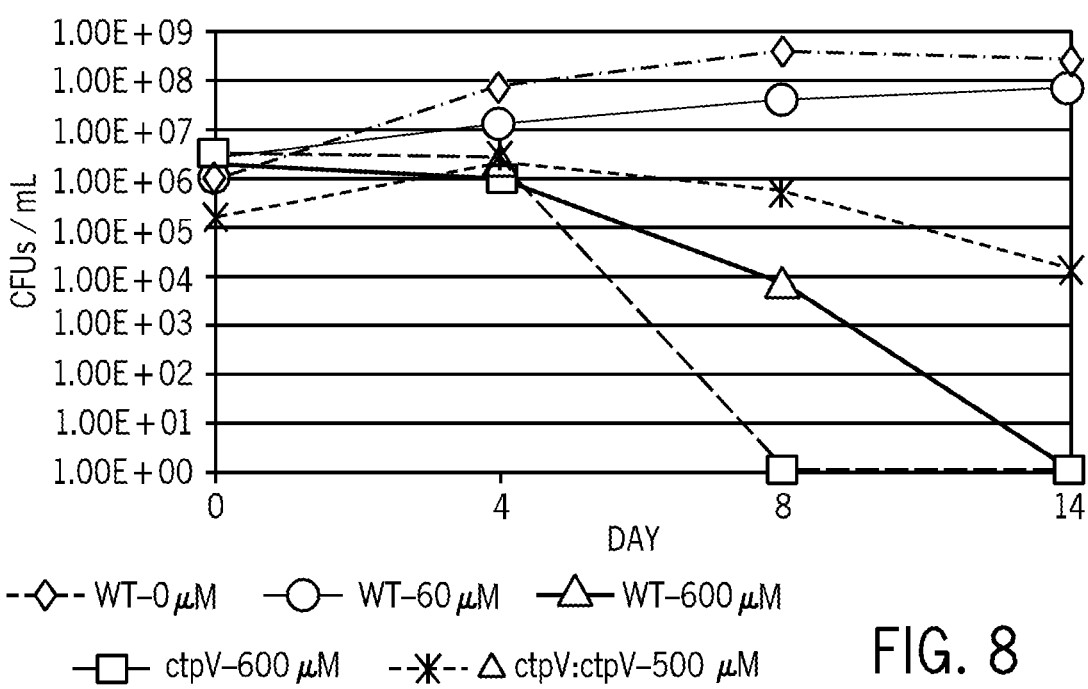
FIG. 8 shows growth curves of the wild-type M. tb in the presence 0 μM and 50 μM and 500 μM $CuCl_2$ and growth curves of the M. tb isogenic mutant ΔctpV and the complemented strain ΔctpV:ctpV in the presence of 500 μM $CuCl_2$.
Figure 9:
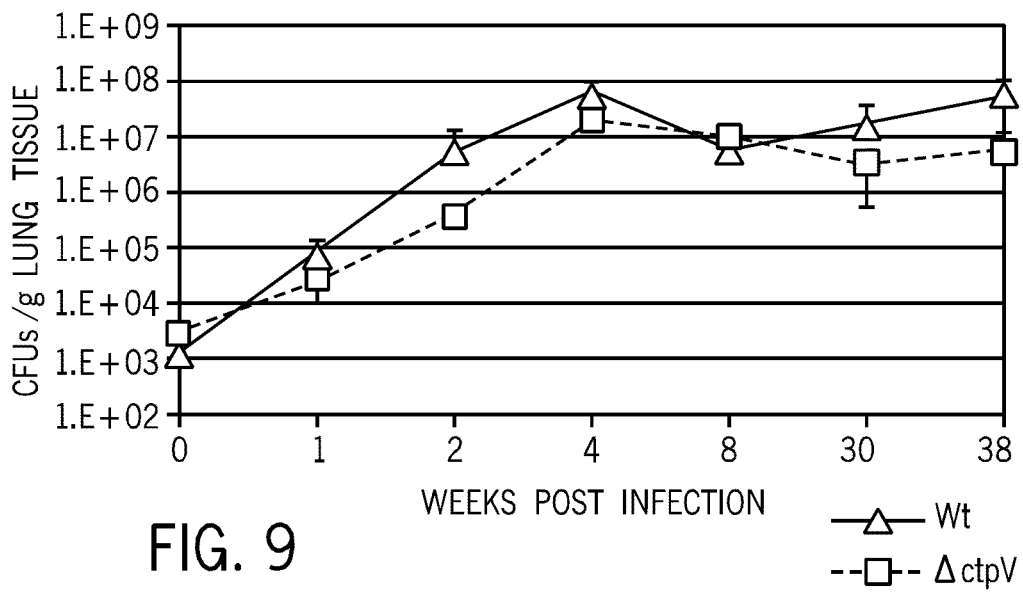
FIG. 9 shows the bacterial load of mouse lungs at various times after infection with either wild-type M. tb (H37Rv) or its isogenic mutant ΔctpV.
Figure 10:
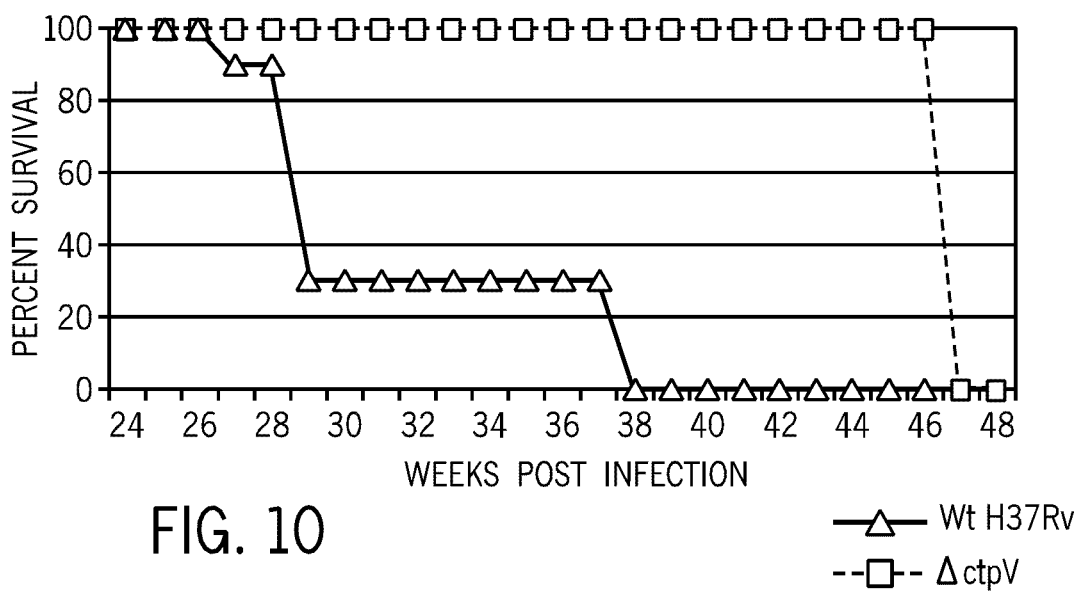
FIG. 10 shows survival of mouse groups (N=10) at various times after infection with either wild-type M. tb (H37Rv) or its isogenic mutant ΔctpV.

Growth at 0 μM and 50 μM $CuCl_2$ were identical among the three strains, as shown in FIG. 7, thus only data for WT at 0 μM and 50 μM $CuCl_2$ are shown in FIG. 8. Referring to FIG. 8, at 500 μM copper, ΔctpV displayed an increased copper sensitivity relative to WT, while the complemented strain showed a decreased copper sensitivity. Comparisons of CFUs of ΔctpV and WT strains revealed that at toxic levels of copper (500 μM $CuCl_2$), the ΔctpV strain, lacking ctpV, survived for 8 days, while the WT strain survived for 14 days.

F. ctpV Expression is Required for Virulence of M. tb

The ctpV gene is part of a 29-gene genomic island called the in-vivo expressed genomic island ("iVEGI") previously shown to be preferentially induced in mice relative to in vitro culture. The ctpV gene may play a role in the survival of M. tb within a host, as experiments have shown that ctpV is a copper exporter, and data indicate that copper homeostasis in bacteria may play a role in pathogenesis, though this had not previously been tested in M. tb.

BALB/c mice were infected with either ΔctpV or wild-type M. tb using a low-dose aerosolization protocol. Bacterial survival and mouse lung pathology were measured at short-term as well as long-term time points via the homogenization and plating of infected lung tissue as well as organ histology. Additionally, mice infected with the two strains were monitored over the long-term course of the infection and the survival of the infected mice was recorded.

Briefly, BALB/c mice (Harlan, Indianapolis, Ind.) were infected in a Glas-Col chamber (Glas-Col, LLC, Terra Haute, Ind.) loaded with 10 mL of either ΔctpV or wildt-type at OD 0.30. Infectious dose of approximately 300 CFU/animal was confirmed via a 1-day time point. CFUs were determined by homogenizing lung tissue in PBS buffer and plating on Middlebrook 7H10+10% ADC, followed by incubation at 37° C. for one month. Final CFUs were normalized to the weight of the lung tissue used. Sections of lung, liver, and spleen tissue were taken and incubated in formalin prior to sectioning and staining with H&E and AFS. Histopathology slides were examined and scored by a pathologist not associated with the study.

As shown in FIG. 9, a decrease in lung CFUs of ΔctpV relative to WT was observed at both short-term and long-term time points. Referring to FIG. 9, the bacterial load of mouse lungs after infection with either wild type (H37Rv) or its isogenic mutant ΔctpV was determined via homogenization of lungs from infected mice (N=3-5 per time point) in PBS and plating on 7H10+ADC (numbers normalized to grams of lung tissue homogenized) with approximately one-log difference seen between ΔctpV and WT at 2 weeks and 38 weeks. Mice infected with ΔctpV lived longer than mice infected with WT, with a 18-week increase in time to death, as shown in FIG. 10. Referring to FIG. 10, the survival of mouse groups (N=10) after infection with WT or ΔctpV is shown. The median survival time for mice infected with WT was 29 weeks, versus 47 weeks for mice infected with ΔctpV.

As shown in FIG. 11, acid-fast stains of histology sections confirm the lower bacterial load of mice infected with ΔctpV compared to infection with the wild-type strain at two weeks post infection. As shown in FIG. 12 and FIG. 36 (4 weeks post infection comparison of mouse lung tissue infected with wild-type, Δctpv and the ΔctpV::ctpv M. tb complement), histopathology revealed lower levels of tissue destruction along the course of infection with ΔctpV relative to WT, even at time points where bacterial load was not significantly different between ΔctpV and WT. At 8 weeks post infection, lung tissue from mice infected with ΔctpV displayed granulomatous inflammation, whereas mice infected with H37Rv displayed massive granulomatous inflammation with more lymphocytic infiltration. And by 38 WPI, granuloma formation occupied almost the whole lungs of mice infected with the wild-type strain, compared to only 50% of tissues of mice infected with the ΔctpV mutant. However, whether wild type or the ΔctpV were used for infection, granulomatous lesions included sheets of lymphocytes and aggregates of activated macrophages. Leisons observed in the complemented strain were very similar to those observed in mice infected with the H37Rv strain.

Immunohistochemstry using IFN-γ antibodies was performed on lung tissue sections from mice infected with WT, ΔctpV or ΔctpV::ctpV M. tb strains. At eight weeks post infection, mice infected with the ΔctpV mutant showed decreased IFN-γ expression relative to mice infected with the corresponding wild-type M. tb strain. The IFN-γ antibody appears brown in FIG. 34.

Taken together, mouse infection data indicates a role for ctpV in M. tb survival in lungs as well as overall virulence and host mortality.

G. Other Genes are Expressed under High Copper Conditions in the ctpV Knockout

In M. tb, ctpV is very highly expressed at toxic concentrations of copper (500 μM), and it has been shown that ctpV is required for normal survival at this level of copper. Interestingly, the genome of M. tb encodes a number of genes with high sequence similarity to ctpV. Specifically, ctpV is a metal translocation P-type ATPase, and there are ten other predicted metal-translocating P-type ATPases in the H37Rv genome with significant sequence similarity to ctpV as shown in Table 1. With the exception of ctpV, potential cation prediction is based solely on sequence data. Percent similarity was determined at the protein level using MATCHER. Sequences were obtained from Tuberculist.

TABLE 1

Predicted Metal-Translocating P-type ATPases in the H37Rv Genome with Significant Sequence Similarity to ctpV

| Gene name | Product name | Potential Cation | % similarity to CtpV |
|---|---|---|---|
| rv0092 | CtpA | Copper | 65.3 |
| rv0103c | CtpB | Copper | 61.4 |
| rv3270 | CtpC | Unknown | 54.7 |
| rv1469 | CtpD | Cadmium | 50.4 |
| rv0908 | CtpE | Unknown | 44.5 |
| rv1997 | CtpF | Unknown | 44.7 |
| rv1992c | CtpG | Unknown | 55.5 |
| rv0425c | CtpH | Unknown | 44.1 |
| rv0107c | CtpI | Magnesium | 44 |
| rv3743c | CtpJ | Cadmium | 49.8 |
| rv0969 | CtpV | Unknown | — |

The presence of redundant proteins is indicated by the delayed copper sensitivity phenotype as shown in FIG. 10. The eight-day delay in a phenotypic difference between WT and ΔctpV implies that, initially, other mechanisms may be able to compensate for the lack of ctpV, although any such functional complementation is only partial after eight days.

Cultures of ΔctpV were exposed to 500 μM $CuCl_2$ for 24 hours and transcript levels of the cells were compared to those of wildtype cultures that had been exposed to the same conditions, as published previously (see e.g., Ward, et al., J Bacteriol 2008 April; 190(8): 2939-46).

Briefly, cultures of ΔctpV were inoculated to OD 0.1 in Sauton's media and allowed to grow shaking at 37° C. to OD 0.6. The cultures were then supplemented with 500 μM $CuCl_2$ and incubated for three more hours prior to spinning down the cultures and freezing immediately at −80° C.

Briefly, RNA was extracted using a Trizol-based method (Invitrogen, Carlsbad, Calif.), and treated with DNAse I (Ambion, Austin, Tex.) to remove contaminating DNA. cDNA was synthesized from 1 μg total RNA using an Invitrogen SuperScript ds-cDNA synthesis kit in the presence of 250 ng genome-directed primers. cDNA clean up, Cy3 labeling, hybridizations, and washing steps were performed using the NimbleGen gene expression analysis protocol (NimbleGen Systems, Inc., Madison, Wis.). Microarray chips were purchased from NimbleGen Systems, Inc., and they contained nineteen 60-mer probes for each of the 3,989 open reading frames identified in the genome of M. tb H37Rv, with five replicates of the genome printed on each slide (total of 95 probes/gene). Slides were scanned using an Axon GenePix 4000B scanner (Molecular Devices Corporation, Sunnyvale, Calif.), and fluorescence intensity levels normalized to 1000. Significantly changed genes between WT and ΔctpV were determined using the EBArrays package in R (R is an open source platform used by Bioconductor, an open source and open development software project). A cutoff value of 0.50 for the probability of differential expression, determined using an LNN model, was used to determine statistically differentially expressed genes.

Ninety-eight genes with significantly different expression levels between ΔctpV and WT after exposure to 500 μM $CuCl_2$ were identified and are listed in Table 2.

TABLE 2

Genes with Significantly Different Expression Levels between ΔctpV and WT after Exposure to 500 μM $CuCl_2$

| rv name | ΔctpV500/ wt500 | Gene name | Description |
|---|---|---|---|
| Gene Regulation | | | |
| rv1221 | 1.86 | sigE | ECF subfamily sigma subunit |
| rv1379 | 1.57 | pyrR | regulatory protein - pyrimidine biosynthesis |
| rv1398c | 2.14 | | conserved hypothetical protein |
| rv1909c | 4.46 | furA | ferric uptake regulatory protein |
| rv1994c | 2.98 | | transcriptional regulator (MerR family) |
| rv3260c | 1.81 | whiB2 | WhiB transcriptional activator homologue |
| Transporters | | | |
| rv0969 | −2.45 | ctpV | cation transport ATPase |
| rv2398c | −2.14 | cysW | sulphate transport system permease protein |
| Membrane/secreted proteins | | | |
| rv0451c | −2.83 | mmpS4 | conserved small membrane protein |
| rv0970 | −3.07 | | hypothetical protein |
| rv1566c | 1.54 | | putative exported p60 protein homologue |
| rv1799 | 1.52 | lppT | probable lipoprotein |
| rv1980c | −2.47 | mpt64 | secreted immunogenic protein Mpb64/Mpt64 |
| rv1987 | 1.90 | | probable secreted protein |
| rv2080 | 2.75 | lppJ | lipoprotein |
| rv3763 | 1.86 | lpqH | 19 kDKD |
| Enzymes | | | |
| rv0247c | −1.72 | | probable iron-sulphur protein *(succinate dehydrogenase) |
| rv0462 | −1.73 | | probable dihydrolipoamide dehydrogenase |
| rv1182 | −2.21 | papA3 | PKS-associated protein, unknown function |
| rv1185c | −1.78 | fadD21 | acyl-CoA synthase |
| rv1471 | 1.89 | trxB | thioredoxin reductase |
| rv1520 | 1.58 | | glycosyltransferase |
| rv1908c | −1.68 | katG | catalase-peroxidase |
| rv2196 | −1.82 | qcrB | cytochrome b component of ubiQ-cytB reductase |
| rv2200c | −1.58 | ctaC | cytochrome c oxidase chain II |
| rv2244 | 2.00 | acpM | acyl carrier protein (meromycolate extension)*(polyketide/fatty acid biosynthesis) |
| rv2445c | −1.58 | ndkA | nucleoside diphosphate kinase |
| rv2930 | −1.75 | fadD26 | acyl-CoA synthase |
| rv3116 | −1.55 | moeB | molybdopterin biosynthesis |
| rv3117 | −1.61 | cysA3 | thiosulfate sulfurtransferase |
| rv3146 | −1.62 | nuoB | NADH dehydrogenase chain B |
| rv3359 | 1.59 | | probable oxidoreductase |
| rv3377c | −1.68 | | similar to many cyclases involved in steroid biosynthesis |
| rv3824c | −1.80 | papA1 | PKS-associated protein, unknown function |
| Mce proteins | | | |
| rv0169 | −1.58 | mce1 | cell invasion protein |
| rv0170 | −1.87 | | part of mce1 operon |

TABLE 2-continued

Genes with Significantly Different Expression Levels between
ΔctpV and WT after Exposure to 500 µM CuCl₂

| rv name | ΔctpV500/wt500 | Gene name | Description |
|---|---|---|---|
| rv0171 | −1.59 | | part of mce1 operon |
| rv0174 | −1.57 | | part of mce1 operon |
| Ribosomal proteins | | | |
| rv0055 | 3.29 | rpsR | 30S ribosomal protein S18 |
| rv0056 | 1.75 | rplI | 50S ribosomal protein L9 |
| rv0710 | 1.52 | rpsQ | 30S ribosomal protein S17 |
| rv0719 | −1.65 | rplF | 50S ribosomal protein L6 |
| rv1298 | 2.11 | rpmE | 50S ribosomal protein L31 |
| rv2882c | −1.65 | frr | ribosome recycling factor |
| Protein fate | | | |
| rv2109c | −2.13 | prcA | proteasome [alpha]-type subunit 1 |
| rv2457c | −1.77 | clpX | ATP-dependent Clp protease ATP-binding subunit ClpX |
| rv2903c | 1.83 | lepB | signal peptidase I |
| rv2094c | 3.74 | tatA | tatA subunit tatAB secretion system |
| rv3875 | 2.09 | esat6 | early secretory antigen target |
| Other | | | |
| rv3841 | 1.75 | bfrB | bacterioferritin |
| rv0001 | −1.61 | dnaA | chromosomal replication initiator protein |
| rv1080c | −1.80 | greA | transcription elongation factor G |
| Hypothetical proteins | | | |
| rv0021c | 1.83 | | conserved hypothetical protein |
| rv0140 | 1.54 | | conserved hypothetical protein |
| rv0236A | −1.53 | | |
| rv0500B | 1.81 | | |
| rv0508 | 1.55 | | hypothetical protein |
| rv0664 | −1.52 | | hypothetical protein |
| rv0686 | −1.72 | | potential membrane protein |
| rv0730 | 1.60 | | conserved hypothetical protein |
| rv0740 | −1.52 | | conserved hypothetical protein |
| rv0755A | 1.90 | | |
| rv0759c | 1.62 | | conserved hypothetical protein |
| rv0991c | 1.60 | | hypothetical protein |
| rv1087A | 1.51 | | |
| rv1134 | 1.61 | | hypothetical protein |
| rv1334 | 1.58 | | conserved hypothetical protein |
| rv1501 | 1.97 | | conserved hypothetical protein |
| rv1532c | 1.51 | | conserved hypothetical protein |
| rv1765A | 2.35 | | |
| rv1783 | −2.18 | | conserved hypothetical protein |
| rv1794 | −2.07 | | conserved hypothetical protein |
| rv1810 | 2.26 | | conserved hypothetical protein |
| rv1982c | 1.69 | | conserved hypothetical protein |
| rv2269c | 1.57 | | hypothetical protein |
| rv2401 | 1.56 | | hypothetical protein |
| rv2623 | −1.58 | | conserved hypothetical protein |
| rv2632c | 1.55 | | conserved hypothetical protein |
| rv2706c | 1.77 | | hypothetical protein |
| rv2708c | 1.51 | | conserved hypothetical protein |
| rv2804c | 1.74 | | hypothetical protein |
| rv2970A | 1.69 | | |
| rv3022A | −2.33 | | |
| rv3131 | −1.73 | | conserved hypothetical protein |
| rv3142c | 2.34 | | hypothetical protein |
| rv3221A | 1.99 | | |
| rv3222c | 1.74 | | conserved hypothetical protein |
| rv3288c | −1.90 | | conserved hypothetical protein |
| rv3395A | 2.24 | | |
| rv3412 | 1.87 | | conserved hypothetical protein |
| rv3492c | −1.57 | | conserved hypothetical protein |
| rv3528c | 1.90 | | hypothetical protein |
| rv3614c | −1.65 | | conserved hypothetical protein |
| rv3616c | 2.53 | | conserved hypothetical protein |
| rv3633 | −1.94 | | conserved hypothetical protein |
| rv3658c | 1.63 | | probable transmembrane protein |
| rv3686c | 2.01 | | conserved hypothetical protein |
| rv3822 | −1.52 | | conserved hypothetical protein |

To confirm the validity of the microarray data, expression levels of nine of the genes identified in the microarray dataset were tested with qRT-PCR.

Briefly, qRT-PCR was performed using a SYBR green-based protocol. cDNA was synthesized from DNAse-treated RNA, obtained as described above, using SuperScript III (Invitrogen) as directed by the manufacturer, in the presence of 250 ng mycobacterial genome-directed primers. 100 ng cDNA was used as template in a reaction with iTaq SYBR green Supermix with ROX (Bio-Rad Laboratories, Hercules, Calif.) in the presence of gene-specific primers (see Table 3) at a concentration of 200 nM. Cycle conditions were 50° C. for 2 min, 95° C. for 3 min, and 40 cycles of 95° C. for 15 seconds and 60° C. for 30 seconds. Reactions were performed in triplicate on an AB7300 machine (Applied Biosystems, Foster City, Calif.) with fluorescence read at the 60° C. step. Threshold cycle values were normalized to 16S rRNA expression.

TABLE 3

Gene-Specific Primers (SEQ ID NOs: 1-28, respectively, in order of appearance)

| Primer | Sequence | Purpose |
| --- | --- | --- |
| AMT371 | ATCACTACTAGTTGAAGACGGTTCGGGGCCAT | ctpV flank cloning |
| AMT372 | ATCACTAAGCTTATAGGCGTGCACGGCGTGCA | ctpV flank cloning |
| AMT567 | ATCACTTCTAGAGGGTTCTCCTCGGTCAGCGTG | ctpV flank cloning |
| AMT568 | ATCACTGGTACCCAGAAACGTCCGCCCCGCTG | ctpV flank cloning |
| AMT874 | GCGGGTGTGGTTGGCCTTGCCGTT | Internal primer for mutant screening |
| AMT875 | GCGGCAACGATCGCCGCACCGATG | Internal primer for mutant screening |
| AMT926 | TGGTGGACCTCGACGACCTGCAGG | ctpV mutant screening |
| AMT887 | ACGAAGCGCGCGAAGGGATGCTGG | ctpV mutant screening |
| AMT885 | GGAACTGGCGCAGTTCCTCTGGGG | ctpV mutant screening |
| AMT886 | TTGACCGCAAAGAAGCGCGCGGCG | ctpV mutant screening |
| AMT1335 | ACCTCGAACATGGACAC | ctpV Forward |
| AMT1336 | ACCGGCAAACAACTGATAC | ctpV Reverse |
| AMT1114 | CAATCCAGGGAAATGTCA | esxA Forward |
| AMT1115 | AGCTTGGTCAGGGACT | esxA Reverse |
| AMT1116 | TCGTTGGGCAAGTCAT | tatA Forward |
| AMT1117 | GCTTCCGCTTTGTTCT | tatA Reverse |
| AMT1132 | AACCCGGTGGCAAACAAC | ctaC Forward |
| AMT1133 | CGCAGTGGCCCACGAATG | ctaC Reverse |
| AMT1168 | CCGTCCTGGAAGCAGTGAATG | furA Forward |
| AMT1169 | AAACGCACGGCACCGAAA | furA Reverse |
| AMT1178 | GCCGCACAGTTCAACGAAAC | rv1471 Forward |
| AMT1179 | CGCACCAGGAGGCCCAAT | rv1471 Reverse |
| AMT1194 | AGCACGATGCCGAAGACCTG | sigE Forward |
| AMT1195 | TGCCCGGCTGGTAATTCTG | sigE Reverse |
| AMT1196 | GTCGAGGAACGAAACCATGCAAT | bfrB Forward |
| AMT1197 | ACCGTGTCTACGCCGGGAAT | bfrB Reverse |
| AMT1198 | CGCGGCGATGAACGACAT | qcrB Forward |
| AMT1199 | ACGGCGGCAGAATCACCAT | qcrB Reverse |

Figure 13:
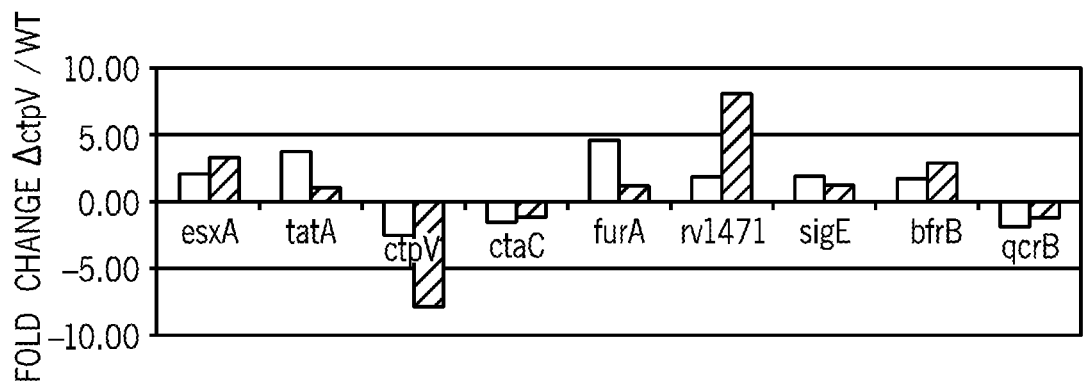
FIG. 13 shows qRT-PCR and microarray data for fold change of expression of selected genes in ΔctpV relative to wild-type.

The microarray fold-change direction was confirmed by qRT-PCR for all nine genes, as shown in FIG. 13. Referring to FIG. 13, from left to right are: esxA, tatA, ctpV, ctaC, furA, rv1471, sigE, bfrB, and qcrB. qRT-PCR was used to confirm selected genes from the microarray data set, using RNA from the original microarray experiment as the source for cDNA. Direction of induction was reproduced in qRT-PCR data 100% of the time with data shown as fold change of expression in ΔctpV relative to WT and normalized to 16S expression. Additionally, qRT-PCR of cDNA from ΔctpV: ctpV cells treated with the same 3-hour exposure to 500 μM copper showed that complementation restored WT-levels of induction for selected genes from the microarray data set.

Because the removal of a copper exporter increases intracellular copper concentration, it was expected that the ΔctpV response to toxic copper levels relative to the response of WT would show a transcriptional response of many of the 15 genes previously associated with copper stress in M. tb. In fact, 11/15 of the genes previously associated with toxic copper response were identified as having significantly changed transcript levels between ΔctpV and WT during copper stress. A number of these genes (N=7) showed a change in the direction of induction (e.g., genes upregulated in general copper response were downregulated after deletion of CtpV).

In addition to the overlap with the copper stress dataset, eighty-seven other genes were identified, including functional categories not previously associated with copper response, such as mammalian cell entry ("mce") family proteins, ribosomal proteins, and a number of membrane/secreted proteins. While these studies have shown that deletion of ctpV invokes a unique response to environmental copper via increased intracellular copper levels, it is apparent that deletion of ctpV also has other affects on the intracellular environment of the bacterium that cannot easily be attributed to copper concentration alone. Though not wishing to be bound by any particular theory, it is possible that the lack of a membrane protein affecting membrane stability or signaling, or deletion causes indirect affects on other proteins such as regulators responsive to generalized cellular stress.

The whole-genome microarray of ΔctpV relative to WT at high copper did not reveal induction of any of the genes with high sequence similarity to CtpV (see Table 1). The more sensitive technique of qRT-PCR was then used to more precisely investigate the transcriptional induction of all of the other P-type ATPases in the M. tb genome.

Figure 14:
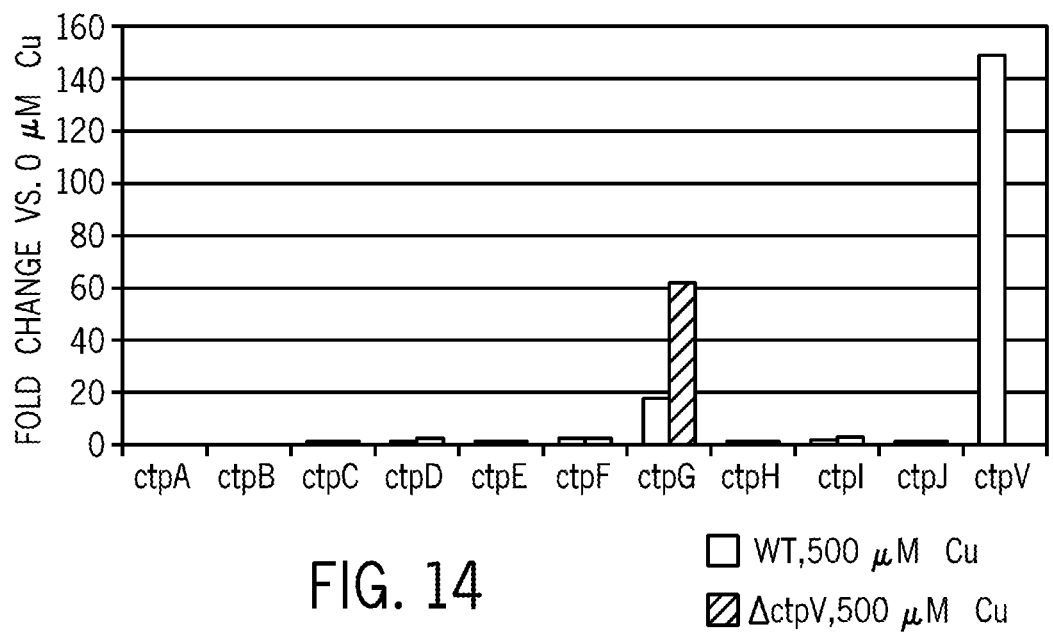
FIG. 14 shows a qRT-PCR survey of the response to copper of all predicated metal-transporting P-type ATPases within the M. tb (H37Rv) genome.
Figure 15:
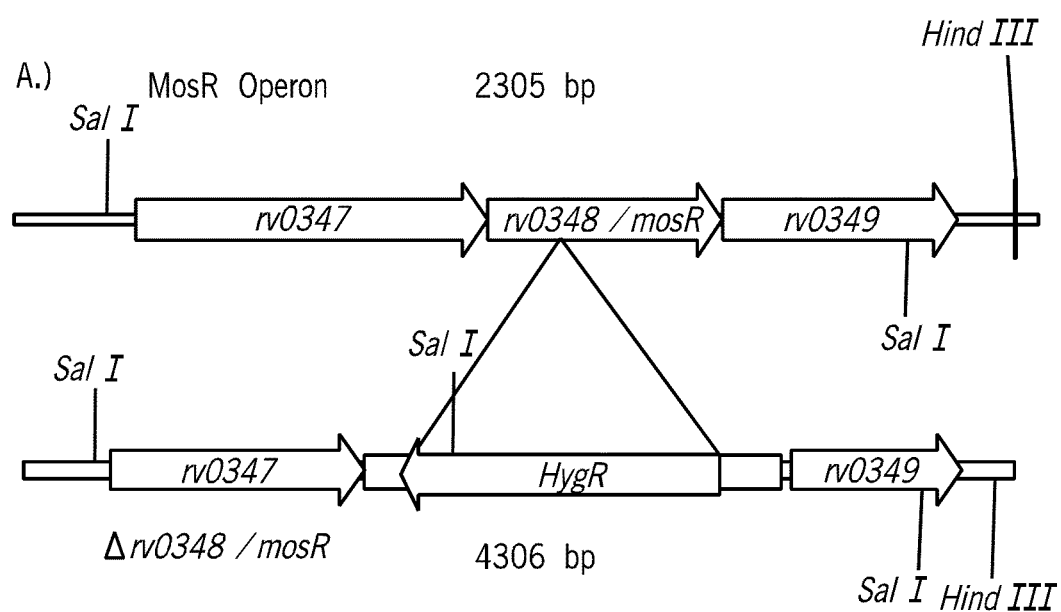
FIG. 15 shows the organization of the rv0348 operon and the strategy for gene disruption.
Figure 16:
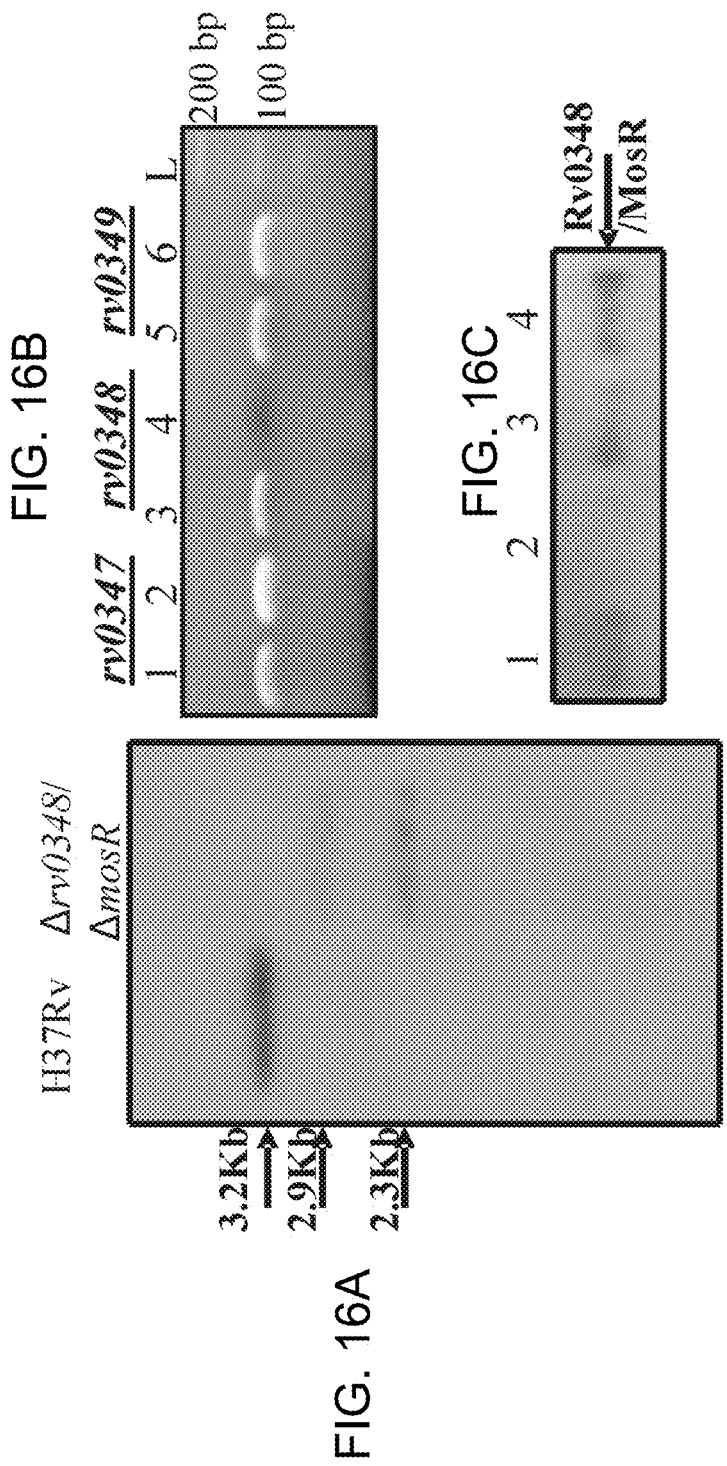
FIG. 16A-C shows Southern blot analysis of SalI-digested genomic DNA of the H37Rv WT and Δrv0348 mutant (A); PCR analysis of cDNA synthesized from RNA samples purified from H37Rv (lanes 1, 3, 5) or Δrv0348 mutant (lanes 2, 4, 6) (B); and Western blot analysis for different M. tb strains using polyclonal antibodies raised in rabbits against MBP-rv0348 protein (C).
Figure 17:
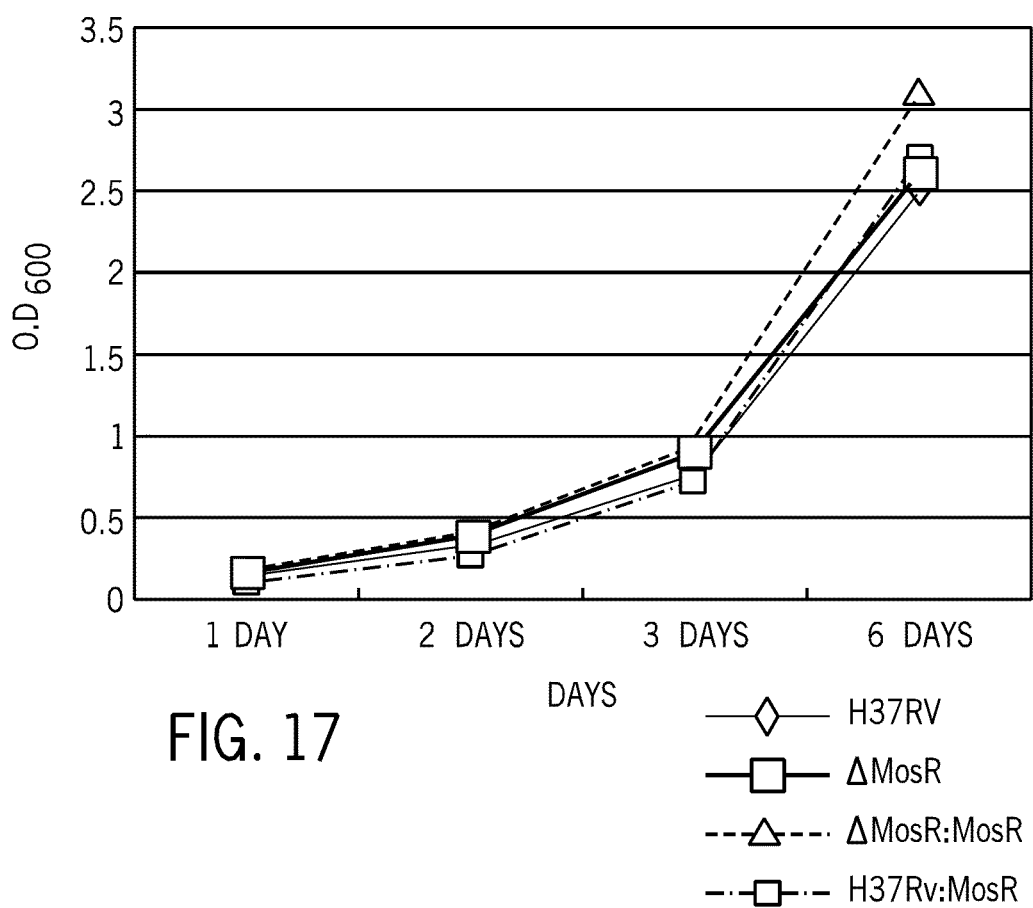
FIG. 17 shows growth curves of four different M. tb strains in Middlebrook 7H9 broth.

These data revealed that only one other P-type ATPase, ctpG, is induced in the presence of copper, and is particularly induced in the absence of ctpV, as shown in FIG. 14. Referring to FIG. 14, a qRT-PCR survey of the response of all predicated metal-transporting P-type ATPases within the M. tb H37Rv genome to copper was conducted. The transcriptional profile at 500 μM copper in the wildtype strain (gray bars) shows induction of only ctpG and ctpV. In the absence of ctpV (black bars), the induction of ctpG is increased. Data are displayed as fold-change relative to expression at 0 μM Cu, and are normalized to expression of 16S.

A predicted metalloregulatory protein, rv1994c, lies upstream of ctpG, and was identified via microarrays as responsive to general copper stress as well as the absence of ctpV.

Example II: rv0348 Knockout Mutant

A. Overview

Earlier analysis of the chronic stage of tuberculosis in mice identified several unique genes induced during chronic infection, including a novel transcriptional regulator encoded by the rv0348 gene (also known as the "mosR" gene). Transcripts for rv0348 were upregulated ~200 fold after 60 and 140 days of M. tb infection in mice, and the Rv0348 protein was shown to bind to its own promoter. In this Example, an M. tb mutant is generated with an inactivated rv0348 gene to examine the role of this gene in M. tb survival in the murine model following aerosol infection.

B. The Δrv0348 Knockout Mutant Shows Attenuated Activity Compared to its Wild-Type Counterpart In BALB/c mice, the bacilli load of the Δrv0348 mutant strain was significantly lower compared to the H37Rv and rv0348-complemented strains, indicating a role for rv0348 in controlling mycobacterial virulence.

1. Strains, Media, Plasmids and Statistical Methods

Escherichia coli DH5α and HB101 were used as host cells for cloning purposes in all experiments of this Example. M. tb H37Rv and *M. smegmatis* mc[2]155 strains were grown in 7H9 Middlebrook liquid medium (BD Biosciences, Rockville, Md.) and on 7H10 Middlebrook plates supplemented with albumin dextrose catalase ("ADC") and antibiotics, when needed (25 μg/ml kanamycin or 50 μg/ml hygromycin). Protocols for DNA manipulations employed throughout this Example, including PCR, cloning, DNA ligations, and electroporation were performed as described in "Molecular cloning, a laboratory manual," Sambrook, et al., Cold Spring Harbor Laboratory Press, Cold Spring Harbor, N.Y. (1989) or according to manufacturer's recommendations. A list of plasmids and constructs used in this Example is presented in Table 4. Student's T-test implemented in Microsoft Excel was used to assess significance difference among samples at p<0.05 level for the reporter assays and bacterial load counts.

TABLE 4

Plasmids and Constructs used in Experiments of Example 2

| Plasmid | Characteristics |
|---|---|
| pYUB854 | Cosmid for disruption construct |
| pMV361 | Integrative mycobacterial shuttle vector. $Kan^R$ |
| *M. smeg*:: pML21 | Recombinant *M. smegmatis* harboring the whole Rv0348 operon under the control of its own promoter in addition to hsp60. $Kan^R$ |
| pML23 | pMV361 harboring Rv0348 gene. $Kan^R$ |
| pCV77 | Replicative shuttle vector with promoterless LacZ transcriptional fusion. $Kan^R$ |
| pML24 | pCV77 with hygromycin cassette in opposite direction to LacZ. $Kan^R$, $Hyg^R$ |
| pML25 | pML24 harboring the promoter region of Rv0347 operon. $Kan^R$, $Hyg^R$ |
| pML26 | pML24 harboring the promoter region of Rv0167 (mce1 operon). $Kan^R$, $Hyg^R$ |
| pML27 | pML24 harboring the promoter region of Rv0700 (rpsJ). $Kan^R$, $Hyg^R$ |
| pML28 | pML24 harboring the promoter region of Rv3130c (tgs1). $Kan^R$, $Hyg^R$ |
| pML29 | pML24 harboring the promoter region of hsp60. $Kan^R$, $Hyg^R$ |

The procedures for cloning, overexpression, and purification of M. tb Rv0348 in *E. coli* are described in Talaat et al., 2007, *J. Bacteriol.,* 189:4265-4274. Total RNA samples were extracted from mycobacterial cultures grown to $OD_{600}$=0.5 or 1.5 using Trizol (Invitrogen, Carlsbad, Calif.) as described in Talaat et al., *Proc. Natl. Acad. Sci U.S.A,* 2004, 101:4602-4607 and Talaat et al., 2007, *J. Bacteriol.,*

189:4265-4274. Extracted mycobacterial total RNA samples were treated with DNAse I (Ambion, Austin, Tex.) until no DNA was detected using PCR primers for the 16S rRNA gene. Primers used in Example 2 are listed in Table 5.

TABLE 5

Primers used in Experiments of Example 2 (SEQ ID NOs: 29-94, respectively, in order of appearance)

| Gene ID | sequence | purpose |
| --- | --- | --- |
| Rv3130c F1 | 5'-gggtttctcaaggcagaaga-3' | qRT-PCR |
| Rv3130c R1 | 5'-ggatcgtccacccatttg-3' | qRT-PCR |
| Rv2628 F | 5'-aatccgccaccatctatcag-3' | qRT-PCR |
| Rv2628 R | 5'-atctcaacggacaggtgctc-3' | qRT-PCR |
| Rv0700 F1 | 5'-ggacagaagatccgcatcag-3' | qRT-PCR |
| Rv0700 R1 | 5'-cccgcgagtccttgtactta-3' | qRT-PCR |
| Rv0167 F1 | 5'-attctttcgcatgtgtgtgc-3' | qRT-PCR |
| Rv0167 R1 | 5'-gaagatcaacagcaccgtca-3' | qRT-PCR |
| Rv0347 F1 | 5'-agcttgccgatctcaaactc-3' | qRT-PCR |
| Rv0347 R1 | 5'-cttctgccggaggttctttc-3 | qRT-PCR |
| Rv0569 F | 5'-cgatagatcaaccggaccac-3' | qRT-PCR |
| Rv0569 R | 5'-cattctgctcctccgcagt-3' | qRT-PCR |
| Rv1996 F | 5'-caacaaacgaacctcggaat-3' | qRT-PCR |
| Rv1996 R | 5'-tactcaaatgcccacccttc-3' | qRT-PCR |
| Rv1997 F | 5'-tcaagaatccaaggcagagg-3' | qRT-PCR |
| Rv1997 R | 5'-tgactcgttcacgctcaatc-3' | qRT-PCR |
| Rv2032 F | 5'-gacttggtggagtcgcagtt-3' | qRT-PCR |
| Rv2032 R | 5'-ccaatgaactgtgcggtatg-3' | qRT-PCR |
| Rv3128c F | 5'-gggctcaaagcttctgtcac-3' | qRT-PCR |
| Rv3128c R | 5-tggtggcctagtggtttttc-3' | qRT-PCR |
| Rv0348A | 5'-actagtctacccgggctgggaggagtttcg-3' | Knockout of Rv0348 |
| Rv0348B | 5'-aagcttgcaaagccgtagtccgcgagctgc-3' | Knockout of Rv0348 |
| Rv0348C | 5'-tctagatggcgggacatcgcacgcgttgtc-3' | Knockout of Rv0348 |
| Rv0348D | 5'-ggtaccaacgggccaacggtgctgtcggag-3' | Knockout of Rv0348 |
| Rv0348 F1 | 5'-TCGCGGACTACGGCTTTG-3' | qRT-PCR in stress conditions |
| Rv0348 R1 | 5'-CCTTGCGCCATTTGGTGATTG-3' | qRT-PCR in stress conditions |
| Rv0348 F2 | 5'-atcctctagaatgaccatttcgttct-3' | Cloning of Rv0348 gene in pMAL-c2 |
| Rv0348 R2 | 5'-gcgcaagcttaccgcttgggtcttat-3 | Cloning of Rv0348 gene in pMAL-c3 |
| Rv0348 F3 | 5'-AAGAATTCGTGCCCGGCGCGCGCGAGTTGACG-3' | Cloning of Rv0348 operon into pMV361 |
| Rv0348 R3 | 5'-CACCCCGCTCAAGCTTGCCTCGAC-3' | Cloning of Rv0348 operon into pMV361 |
| Rv0348 F4 | 5'-ggggaattcatgaccatttcgttctctagc-3' | Cloning of Rv0348 gene into pMV361 |
| Rv0348 R4 | 5'-TGGAAGCTTTTACCGCTTGGGTCTTATCGA-3' | Cloning of Rv0348 gene into pMV361 |

TABLE 5-continued

Primers used in Experiments of Example 2 (SEQ ID NOs: 29-94, respectively, in order of appearance)

| Gene ID | sequence | purpose |
| --- | --- | --- |
| Rv0347 F2 | 5'-cggtctagaAttgagctccctgggatggtg-3' | Cloning into pML24 |
| Rv0347 R2 | 5'-cggaagcttggccgtcacaacattcatgataa-3' | Cloning into pML24 |
| Rv3130c F2 | 5'-cggaagcttGTAACCGCTGCCCGAAC-3' | Cloning into pML24 |
| Rv3130c R2 | 5'-cgcggatccCACACCACAGCTGAGGATCA-3' | Cloning into pML24 |
| Rv0700 F2 | 5'-cggtctagaCGGGAAGCTCGCAGGTgg-3' | Cloning into pML24 |
| Rv0700 R2 | 5'-cggaagcttCTCCCGCGAGTCCTTGTac-3' | Cloning into pML24 |
| Rv0167 F2 | 5'-cggtctagaCGAAGACCTAGGTGAGTTCCTG-3' | Cloning into pML24 |
| Rv0167 R2 | 5'-cggaagcttGAGCGTGAAGATCAACAGCA-3' | Cloning into pML24 |
| hsp60 | 5'-cgctctagacgggtcttgttgtcgttggcgg-3' | Cloning into pML24 |
| hsp60 | 5'-cggaagcttcattgcgaagtgattcctccgg-3' | Cloning into pML24 |
| Rv0347 F3 | 5'-ttgtcgtgccgaccgtcgcggg-3' | EMSA |
| Rv0347 R3 | 5'-ggagtccatcgcgccagctcct-3' | EMSA |
| Rv0165c F | 5'-tcaacggcagcaccacgtgg-3' | EMSA |
| Rv0165c R | 5'-tgacccgatcgccgaaaccg-3' | EMSA |
| Rv0823c F | 5'-acacagcgcccggaatgcga-3' | EMSA |
| Rv0823c R | 5'-ggaagcccgtacgggcaaga-3' | EMSA |
| Rv1846c F | 5'-gtgtaggcaaggtcgcggcg-3' | EMSA |
| Rv1846c R | 5'-ggctgcacgtccttgtgtctacacc-3' | EMSA |
| Rv2160c F | 5'-cagctcgaacgcgagttggc-3' | EMSA |
| Rv2160c R | 5'-aagccatgcctagcgccgac-3' | EMSA |
| Rv1996 F | 5'-gaagacgaggagcaccggcgct-3' | EMSA |
| Rv1996 R | 5'-gtgcgcttgggcgaccaggtac-3' | EMSA |
| Rv3139 F | 5'-TGCCCAGGCTGCCGGGCAACG-3' | EMSA |
| Rv3139 R | 5'-gcgcagtgatcggttcagcgga-3' | EMSA |
| Rv0145 F | 5'-GTCTCTTCGTTGGCCGAGACGCTGT-3' | EMSA |
| Rv0145 R | acccgccgacgacaccaacacc | EMSA |
| Rv3825c F | 5'-ccacttgcacaccgtccgaccg-3 | EMSA |
| Rv3825C R | 5'-gaagcgtcagactaccggcccg-3' | EMSA |
| Rv3130c_F3 | 5'-GTAACCGCTGCCCGAAC-3' | EMSA |
| Rv3130c_R3 | 5'-CACACCACAGCTGAGGATCA-3' | EMSA |
| Rv0700_F3 | 5'-CGGGAAGCTCGCAGGT-3' | EMSA |
| Rv0700_R3 | 5'-CTCCCGCGAGTCCTTGT-3' | EMSA |
| Rv0167_F3 | 5'-CGAAGACCTAGGTGAGTTCCTG-3' | EMSA |
| Rv0167_R3 | 5'-GAGCGTGAAGATCAACAGCA-3' | EMSA |

2. Construction of the rv0348 Knockout Mutant

The strategy to construct the rv0348 mutant included the insertion of a hygromycin cassette within the coding sequence of the rv0348 gene using a specialized transduction-based protocol. Attempts to delete the whole gene with the 200 bp flanking sequences failed to yield any mutants. Earlier transposon mutagenesis indicated the rv0347 gene flanking the rv0348 sequence was essential, explaining the failure to delete the whole rv0348 gene where flanking sequences were disrupted. However, following specialized transduction of the insertion constructs (introducing the hyg$^r$ sequence at 269 bp after the start of rv0348) to the M. tb H37Rv strain, several transductants were obtained. The coding sequence of rv0348 could not be replaced by hygR sequence so the generated mutant had all the sequence of rv0348 but with hygR inserted at 269 bp after the translation start of rv0348.

Figure 18:
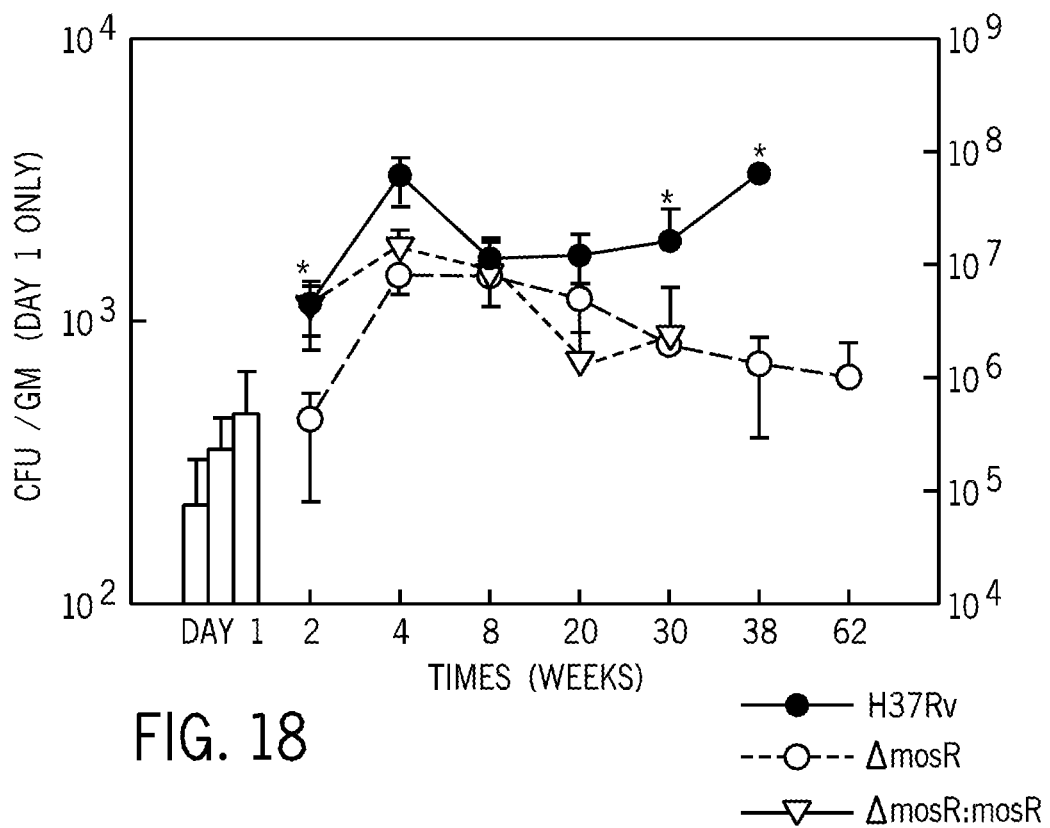
FIG. 18 shows lung CFU/GM in murine lungs following aerosol infection with H37Rv, Δrv0348, and Δrv0348::rv0348.
Figure 19:
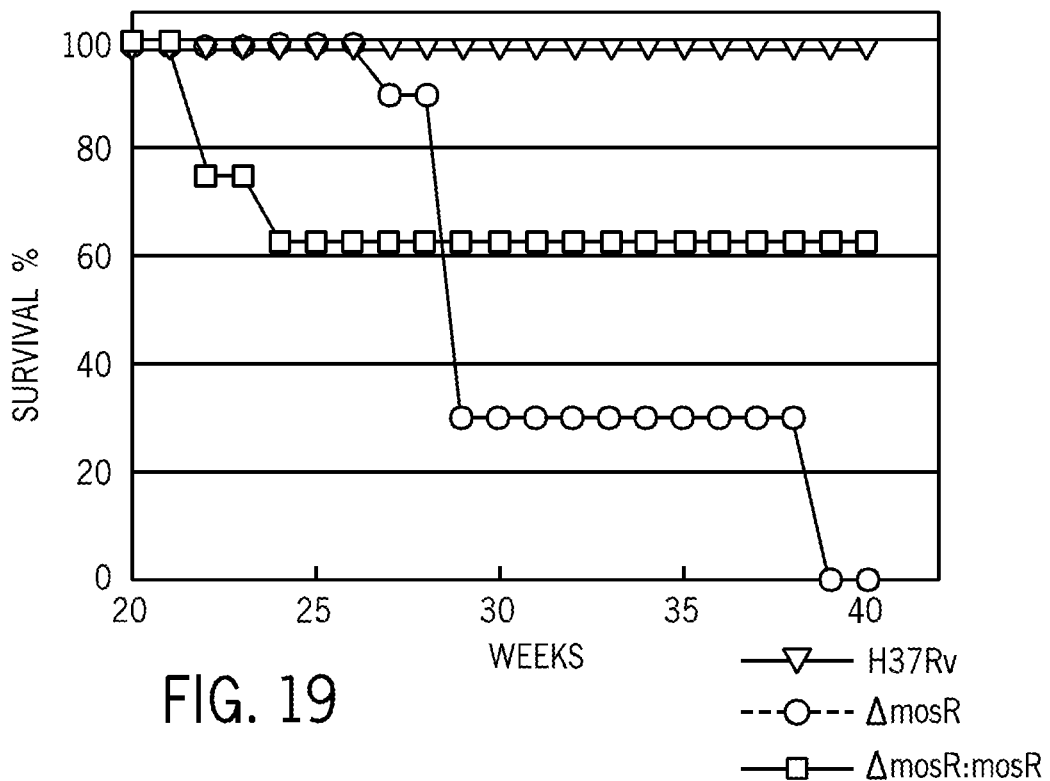
FIG. 19 shows survival curves of three mice groups (N=10) infected with H37Rv, Δrv0348, and Δrv0348::rv0348.

A specialized transduction protocol was adopted with a few modifications to inactivate the rv0348 gene using the virulent strain of M. tb H37Rv. Approximately 800 bp-fragments flanking the rv0348 ORF (specifically, flanking the 269 bp) were amplified using standard PCR protocols. Amplicons were cloned into pGEM-T vector (Promega, Madison, Wis.) and sequence verified before ligation into the pYUB845 vector using SpeI and HindIII for left arm and XbaI and Acc65I for right arm to form the Allelic Exchange Substrate ("AES"). Construction of specialized transducing mycobacteriophages and transduction protocols were performed as described in Bardarov et. al., 2002, *Microbiol.,* 148:3007-3017. Following 6 weeks of incubation at 37° C., hygromycin-resistant colonies were selected for further analysis. PCR and Southern blot analyses were used to verify the mutant genotypes as described before (see, Talaat, et al., 2000, *Am. J. Vet. Res.,* 61:125-128 and Wu et al., 2007, *J. Bacteriol.,* 189:7877-7886). PCR, sequencing and Southern blot analyses of several transductants, shown in FIG. 16, verified the desired genotype (Δrv0348) in all transductants, and one of them was chosen for the rest of the analyses.

FIG. 15 shows the organization of the rv0348 operon and the strategy for gene disruption. Data in FIG. 16A show a Southern blot analysis of Sail-digested genomic DNA of the H37Rv WT and Δrv0348/Δrv0348 mutant. Data in FIG. 16B show PCR analysis of cDNA synthesized from RNA samples purified from H37Rv (lanes 1, 3, 5) or Δrv0348/Δrv0348 mutant (lanes 2, 4, 6). Presence of transcripts of the upstream and downstream genes of the rv0348 gene indicate that the Δrv0348 mutant is non-polar.

To generate antibodies against purified Rv0348, two adult male New-Zealand White rabbits were inoculated with 125 μg of the recombinant fusion protein in Fruend's incomplete adjuvant (Sigma, St. Louis, Mo.) using an approved protocol by the Institutional Animal Care and Use Committee. Rabbits were housed individually in cages at 15 to 18° C. and given antibiotic-free food and water ad libdium. Each immunization was administered subcutaneously (12.5 μg), intradermally (37.5 μg), intramuscularly (50 μg), and intraperitoneally (25 μg) in accordance with the manufacturer's suggestions. Injections of the antigen-adjuvant mixture were administered every 3 weeks for a total of three immunizations. Antibody titers for seroconverted rabbits were measured by ELISA and immunoblot using recombinant purification tag-specific antibodies.

For immunoblotting, mycobacterial cultures were harvested and lysed by boiling in PBS buffer. Total crude extracts were centrifuged and soluble lysates and insoluble pellets were separated on 12% SDS-PAGE and transferred onto PVDF membrane (Hybond-P, Amersham Biosciences). Membranes were saturated by 5% dried milk and rabbit polyclonal antibody was used as primary antibody at a dilution of 1/5000 for 2 hrs. Horse raddish peroxidase conjugated to goat anti-rabbit IgG (Pierce Thermo Scientific, Rockford, Ill.) was used as secondary antibody at 1/30000. Membranes were developed by Chemiluminescent kit according to the manufacturer's protocol (Pierce).

Data in FIG. 16C show a Western blot analysis for different M. tb strains using polyclonal antibodies raised in rabbits against MBP-Rv0348 protein. Pellets from (1) M. tb H37Rv, (2) Δrv0348 mutant, (3) Δrv0348::rv0348 complemented strain, and (4) H37Rv::rv0348 overexpression strain, were subjected to immunoblotting. The level of expression of Rv0348 protein in M. tb H37Rv compared to other constructs was examined in order to determine its expression (or lack of expression) in M. tb bacilli with variable rv0348 constructs. Rv0348 was detectable, but at low levels, when mycobacterial pellets not culture filtrate samples were analyzed using Western blot, indicating intracellular expression of the Rv0348 protein. The blot for soluble fractions was negative (data not shown).

3. Construction and Evaluation of an rv0348 Complement

The selected Δrv0348 mutant was further used to construct the complementation strain where the coding sequence of rv0348 is expressed in-trans using pMV361-rv0348 to yield the Δrv0348::rv0348 construct. Attempts to introduce the whole operon into M. tb were unsuccessful due to several genomic rearrangements (data not shown). As can be seen in FIG. 17, growth curves for all strains—wild type H37Rv, its isogenic mutant Δrv0348, complemented strain Δrv0348::rv0348, and M. tb H37Rv: rv0348—showed no measurable difference during in vitro growth in Middlebrook 7H9 broth. The four M. tb strains were inoculated into Middlebrook 7H9 broth at O.D600 0.02 and cultures were shaken at 37° C. in an incubator for six days. OD was monitored during the incubation time.

For complementation experiments, the coding sequence of the entire rv0348 operon (2.3 kb) or the coding sequence of the rv0348 gene alone (~654 bp) were amplified by PCR. Amplicons were cloned into pGEM-T vector and subsequently verified by DNA sequencing. Vectors were double digested by EcoRI and HindIII restriction enzymes followed by ligating gel-purified inserts into pMV361 to give rise to pML21 (Oprv0348) and pML23 (rv0348) shuttle vectors for the expression of the whole operon or rv0348 gene, respectively. Both plasmids (pML21 and pML23) were independently electroporated into electrocompetent *M. smegmatis* and M. tb H37Rv cells. Transformants were selected and subsequently analyzed by PCR to verify integration of the delivered sequences into the M. tb genome. Expression of the Rv0348 protein was further examined using immunoblotting as described above.

4. Evaluation of Δrv0348, Complement Δrv0348:rv0348 and Wild-Type M. tb strain H37Rv Three groups (N=40) of 5-week old BALB/c mice were infected with H37Rv, Δrv0348 or Δrv0348::rv0348 strains and housed in BSL3 environment using an approved protocol from the University of Wisconsin, Institutional Animal Care and Use Committee ("IACUC"). Cultures of M. tb H37Rv, Δrv0348 and Δrv0348::rv0348 strains were grown to mid-log phase ($OD_{600}$=1). A total of 10 ml cultures adjusted to $OD_{600}$=0.3 were suspended in sterile PBS buffer and used for aerosolization using the Glass-Col aerosol chamber (Terra-Haute, Ind.) to generate an infectious dose of 200-400 cfu per mouse. Two mice were sacrificed at 4-6 hours post infection to enumerate the infectious dose by plating on 7H10 Middlebrook plates in the presence of hygromycin and/or kanamycin for the mutant and complemented strains, respectively. Mice (N=5) were sacrificed at different times post infection to remove lungs for plating on Middlebrook 7H10 agar for colony counting. Portions of livers, spleens and lungs were fixed in 10% neutral buffered formalin for at least 2 hrs before sectioning and staining with hematoxylin and eosin ("H&E") stain and Ziehl-Neelsen stain.

Culturing lung tissues at day 1 post infection confirmed that all groups of mice received a comparable infectious dose of each strain (220 CFU/mouse for H37Rv, 350 CFU/mouse for the Δrv0348 and, 460 CFU/mouse for the Δrv0348::rv0348). Murine survival and lung colonization following aerosol infection M. tb with different copies of rv0348 is shown in FIGS. 18-20. FIG. 19 shows survival curves of 3 mice groups (N=10) infected with H37Rv, Δrv0348 and Δrv0348::rv0348. FIG. 18 shows lung CFU/GM murine lungs following aerosol infection with H37Rv, Δrv0348 and Δrv0348::rv0348. The "*" denotes significant difference at these times (Student's t-Test). FIG. 20 shows histological analysis of lung sections of mice lungs at 2 weeks and at 20 weeks after infection with H37Rv, Δrv0348, and Δrv0348::rv0348. Note the level of accumulation of inflammatory cells (arrow heads) in H&E stained sections of mice groups.

Figure 21:
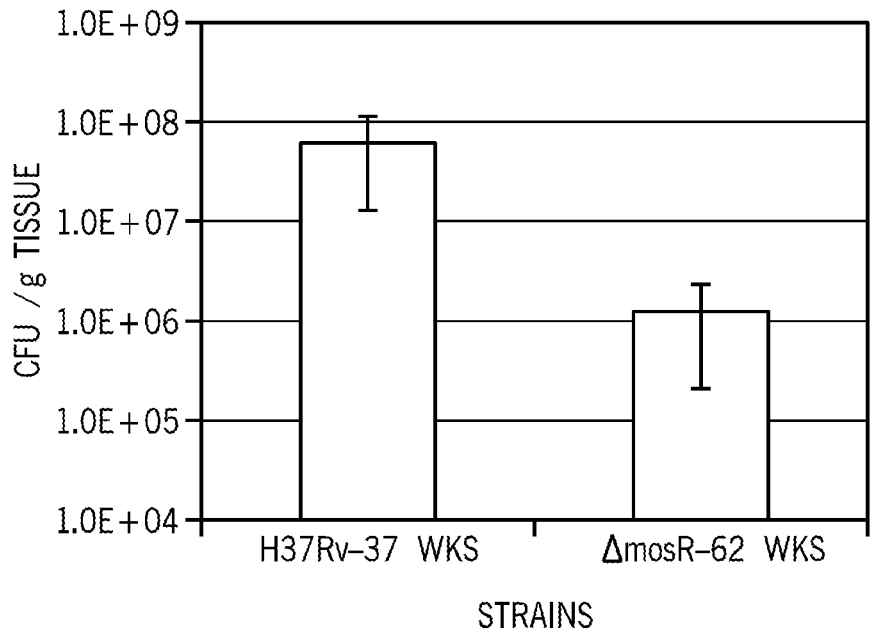
FIG. 21 shows CFU/g tissue in murine lungs at time of death for H37Rv wild-type strain (37 weeks) and for Δrv0348 strain (62 weeks).

As shown in FIG. 19, all mice infected with the Δrv0348 mutant survived the infection up to 40 weeks post infection ("WPI"; end of experiment) with a median survival time ("MST") >40 weeks, while mice infected with the wild type strain, H37Rv began to die at 27 WPI with MST=29 weeks. As shown in FIG. 18, the mycobacterial count for the Δrv0348-infected group was significantly different from other groups, especially at 2, 30, 38 WPI, as at these WPI, the bacterial loads of the mutant strain were significantly lower than the wild type strain. This lower bacterial load of the mutant strain is further demonstrated by data shown in FIG. 21, which shows CFU/g tissue in murine lungs at time of death for H37Rv wild-type strain, which occurred at 37 weeks, and for Δrv0348 strain, which occurred at 62 weeks.

The difference in CFU counts was mostly observed following 30 WPI and later, indicating a critical role for rv0348 in the chronic rather than the early phase of tuberculosis, where the difference was observable in only one data point. Initial colony counts of the complemented strain, Δrv0348::rv0348 at 2 WPI were similar to those of the wild type H37Rv strain indicating successful complementation of Rv0348. Nonetheless, colonization levels at subsequent times, in addition to its survival curve, indicated only a partial complementation of Rv0348 activity. PCR analysis of the retrieved colonies from mice lungs infected with the Δrv0348::rv0348 strain at all times indicted the stability of the complementation construct, even after 30 WPI in mice (data not shown). Failure of complementation after 8 weeks of infection could be explained by the strength of rv0348 operon promoter in comparison to hsp60 promoter used in the complementation construct. LacZ assays in *M. smegmatis* showed that hsp60 promoter is at least 4 times weaker than the promoter of rv0348 operon (data not shown). Deficiency of in vivo complementation was encountered for several other genes using similar complementation vectors and strategy.

As shown in FIG. 20, histopathological analysis of infected mice tissues showed typical, progressive granulomatous lesions in lungs of mice infected with the wild type or complemented strains where aggregates of foamy macrophages were observed by 20 WPI. Granulomas were more visible as the disease progressed where they occupied almost the whole lungs by the time of death (~29 WPI). Conversely, a lower level of macrophage and lymphocyte aggregates were observed in mice infected with the zfrv0348 mutant. Notably, inflammatory lesions were visible in 100% of lung sections of mice infected with H37Rv starting at 20 WPI and later, while lesions were observed in only 50% of lung sections of mice infected with the Δrv0348 mutant. This level of inflammatory response did not change significantly by the end of the experiment (40 WPI) when Δrv0348-infected mice were sacrificed. Overall, bacterial loads and survival curves in addition to histopathological analyses indicated the attenuation of the Δrv0348 mutant, especially during chronic tuberculosis.

C. rv0348 Function under Variable Stress Conditions

The transcriptional profiles of the isogenic mutant relative to its parental strain, H37Rv, indicated the regulation of several gene groups organized into operons and regulons including those involved in mammalian cell entry (mce1), hypoxia (dosR) and starvation.

The ability of the Rv0348 protein to affect transcription of these genes was further analyzed using a LacZ reporter assay and quantitative, real-time PCR (qRT-PCR).

1. Expression of rv0348 under Variable Stress Conditions

Transcripts constituting the rv0348 operon are known to be activated during starvation and extended anaerobic conditions. To examine the role of rv0348 gene in other mycobacterial defenses, cultures of the wild type strain H37Rv and its isogenic mutant, Δrv0348, were exposed to stress conditions that are thought to be activated during intracellular survival of M. tb. Following exposure to variable stressors, both colony counts and transcriptional profiles of rv0348 transcripts were assayed (for the H37Rv strain only).

Cultures for M. tb H37Rv, H37RvΔrv0348, complemented strain, Δrv0348::rv0348, or H37Rv M. tb:rv0348 were grown to early log phase ($OD_{600}$=0.5) and their colony counts were determined by plating on Middlebrook 7H10 agar plates in order to calculate the viable cells at the beginning of the experiment. Aliquots (10 ml) were subjected to 0.05% SDS treatment (Sodium Dodecyl Sulfate, Sigma) for 4 hrs at 37° C. or to heat shock at 45° C. for 24 hrs in a slow-shaking incubator. To test static growth conditions, 50 ml-aliquots of M. tb constructs were allowed to grow for 2 and 6 months without shaking in closed Falcon tubes. At the designated times, culture aliquots were plated and counted on Middlebrook 7H10 agar. Other aliquots were used for RNA isolation to assess the expression of rv0348 under the examined stress conditions using quantitative, real-time PCR ("qRT-PCR").

For qRT-PCR, cDNA was synthesized from 1 µg of total RNA using SuperScript III (Invitrogen) as directed by the manufacturer, in the presence of SYBR green and 250 ng of mycobacterial genome-directed primers. SYBR green qRT-PCR was done using gene specific primers (Table 5) at a concentration of 200 nm. The thermocycle conditions were: 95° C. for 3 min, and 40 cycles of 95° C. for 15 S and 60° C. for 30 S. qRT-PCR reactions were performed in triplicates and the threshold cycle values were normalized to levels of 16SrRNA transcripts and fold changes were calculated by $\Delta\Delta C_T$ method.

Transcriptional Analysis was performed as follows. Before DNA microarray hybridizations, double-stranded cDNA (ds-cDNA) was synthesized from 10 ug of total RNA using the SuperScript Double-Stranded cDNA Synthesis Kit (Invitrogen) as directed by the manufacturer, in the presence of 250 ng genome-directed primers. The ds-cDNA was cleaned up and labeled following the NimbleGen gene expression analysis protocol (NimbleGen Systems, Inc., Madison, Wis.) and hybridized to NimbelGen-manufactured microarrays following a protocol we established earlier. In this microarray, each of the 3989 open reading frames ("ORFs") encoded in the genome of M. tb H37Rv strain, was represented by nineteen of 60 mer oligonucleotide probes. Further, the whole genome was represented five times on each chip (i.e. 5 technical replicates/chip) for a total of 95 probes/gene. All hybridizations (3 µg of double-stranded cDNA/Chip) were performed using NimblGen hybridization buffer and commercial hybridization chambers (TeleChem International, Inc., Sunnyvale, Calif.) overnight at 42° C. Following hybridization, washing steps were performed using Nimblegen washes I, II, and III as recommended by the manufacturer. Slides were scanned using an Axon GenePix 4000B scanner (Molecular Devices Corporation, Sunnyvale, Calif.) and fluorescent intensity levels extracted using NimbleScan (NimbleGen) and normalized to a mean value of 1,000. Determination of significantly changed genes was performed using a flexible empirical Bayes model; specifically, the LNN model in the EBArrays package employing an R language (R is an open source platform used by Bioconductor, an open source and open development software project). A cutoff of 0.50 for the probability of differential expression (PDE>0.5) was used to determine significantly changed genes. Statistical enrichment of gene groups within the microarray genes vs. other transcriptoms were calculated using a standard hypergeometric distribution function in Microsoft Excel.

Figure 22:
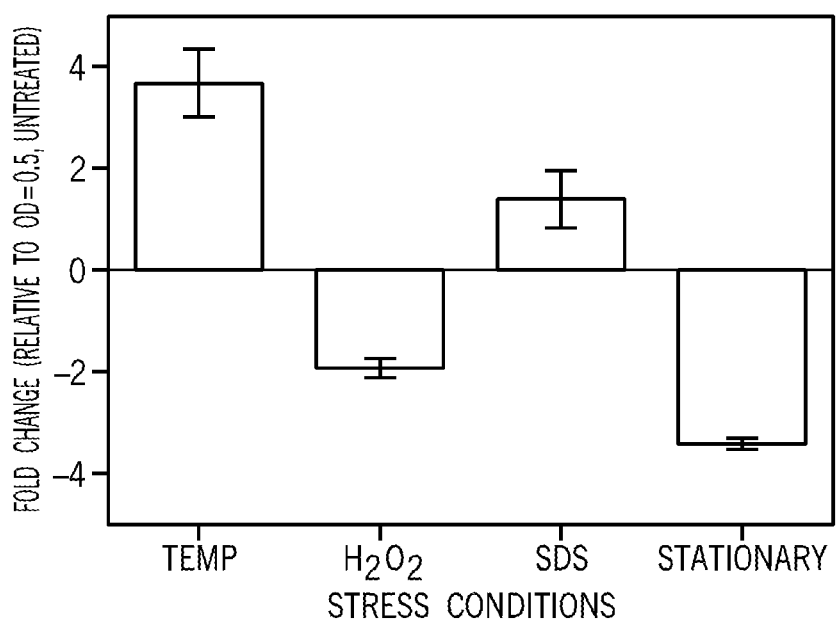
FIG. 22 shows a transcriptional profile of rv0348 in M. tb (H37Rv) under variable stressors.

FIG. 22 shows the transcriptional profile of rv0348 in M. tb H37Rv by qRT-PCR of rv0348 transcripts under variable stress conditions, such as high temperature (45° C.), $H_2O_2$ (10 mM) and SDS (0.05%) treatments, as well as transition to stationary phase ($OD_{600}$=1.5). Fold change was calculated relative to transcripts in untreated cultures of M. tb H37Rv strain ($OD_{600}$=0.5). Error bars represent ±standard deviations from the means (bars). qRT-PCR showed that the transcripts of rv0348 remained unchanged when M. tb cultures were exposed to SDS (0.05%).

Figure 23:
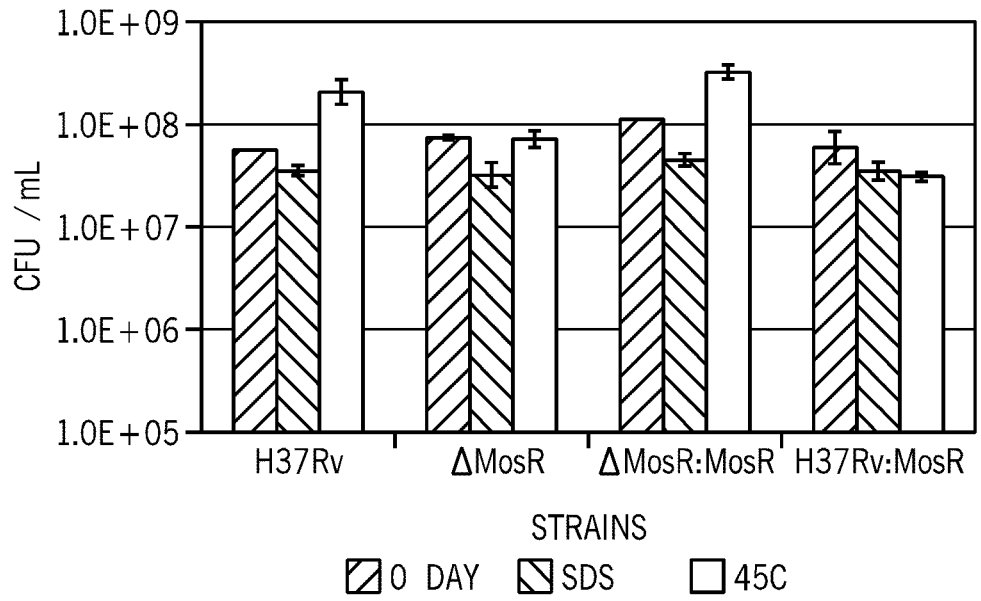
FIG. 23 shows colony counts of four different M. tb strains subjected to different stressors.

The transcriptional profile of rv0348 indicated induction at 45° C. and repression following exposure to high levels of $H_2O_2$ or during the stationary phase of growth. On the other hand, no difference in colony counts was found when mycobacterial cultures (H37Rv and Δrv0348) were exposed to any of the examined stressors including culturing under static conditions for 2-6 months at 37° C. As shown in FIG. 23, different M. tb strains were grown in Middlebrook 7H9 liquid medium to early log phase (OD600=0.5) and their counts were determined. Aliquots of each strains (10 ml) were subjected to different stressor (SDS 0.05%, for 4 hrs) or to heat shock at 45° C. for 24 hours and the CFUs were determined for all strains by plating on Middlebrook 7H10 plates at 37° C.

2. Global Changes in M. tb Transcriptome Triggered by rv0348

It has been suggested that rv0348 plays a role in the transcriptional regulation of M. tb during the transition to the chronic stage in murine lungs. To identify genes under control of rv0348, cultures of both H37Rv and its isogenic mutant, Δrv0348, were grown in vitro for DNA microarray analysis using a high-sensitivity oligonucleotide microarray platform.

Replicate microarray hybridizations were performed for at least two biological samples of both the wild type and mutant strains and showed a high correlation level (r=0.9). Using a standard protocol for Bayesian statistics, significantly regulated genes with a probability of differential expression (PDE) >0.5 and >±2 fold change between H37Rv and Δrv0348 mutant were identified. Using these criteria, a significant change in a set of 163 genes (Table 11) was identified between the transcriptomes for H37Rv and the Δrv0348 (rv0348-regulon).

Table 11 shows a list of the 163 genes whose expression differs in Δrv0348 as compared to the wild-type M. tb counterpart H37Rv. Functional category code for Table 11: 0 virulence, detoxification, adaptation; 1 lipid metabolism; 2 information pathways; 3 cell wall and cell; processes; 4 stable RNAs; 5 insertion seqs and phages; 6 PE/PPE; 7 intermediary metabolism and respiration; 8 unknown; 9 regulatory proteins; 10 conserved hypotheticals; 16 conserved hypotheticals with an orthologue in M. bovis. A partial list of significantly changed genes organized into operons, as determined by an operon prediction algorithm, is listed in Table 6.

TABLE 6

A List of Mycobacterial Operons under Positive and Negative Control of Rv0348

| No. | Gene-ID | Operon Name* | Putative Function |
|---|---|---|---|
| Positive Regulation | | | |
| 1 | Rv0167-0177 | mce1 | Mammalian cell entry operon |
| 2 | Rv0684-0685 | fusA-tuf | Elongation factor |
| 3 | Rv0700-0710 | rpsJ-rpsQ | 30S ribosomal protein S10 |
| 4 | Rv0718-0723 | rpsH-rplO | 30S ribosomal protein S10 |
| 5 | Rv1184c-1185c | Rv1184c-1185c | Conserved hypothetical protein, acyl-CoA synthase |
| 6 | Rv1613-1614 | trpA-ltg | Tryptophan synthase α chain, prolipoprotein diacylglyceryl transferase |
| 7 | Rv2391, 2392 | nirA-cysH | Probable nitrite reductase/sulphite reductase |
| 8 | Rv2948c-Rv2950c | fadD22-fadD29 | acyl-CoA synthase |
| 9 | Rv3148-Rv3154 | nuoD-nuoJ | NADH dehydrogenase chain D-J |
| 10 | Rv3460c** | rpsM-J | 30S ribosomal protein S13-L36 |
| 11 | Rv3824c-Rv3825c | papA1-pks2 | PKS-associated protein, unknown function, polyketide synthase |
| 12 | Rv3921c-Rv3924c | rnpA, rpmH | Unknown membrane protein |
| Negative Regulation | | | |
| 13 | Rv0823c-Rv0824c | desA1 | Transcriptional regulator, ntrB (NifR3/Smm1 family) |
| 14 | Rv1622c, Rv1623c | cydB, appC | Cytochrome d ubiquinol oxidase subunit II |
| 16 | Rv2031c** | hspX | 14 kD antigen, heat shock protein Hsp20 family |

TABLE 6-continued

A List of Mycobacterial Operons under Positive and Negative Control of Rv0348

| No. | Gene-ID | Operon Name* | Putative Function |
|---|---|---|---|
| 17 | Rv2629-Rv2630 | Rv2629-Rv2630 | Hypothetical protein |
| 18 | Rv3048c** | nrdG | Ribonucleoside-diphosphate small subunit |
| 19 | Rv3053c** | nrdH | Glutaredoxin electron transport component of NrdEF |
| 20 | Rv3139-Rv3140 | fadE24, fadE23 | acyl-CoA dehydrogenase |

*Operon predications are based on earlier analysis.
**Single genes of a larger operon or regulon.

Induced genes in the H37Rv transcriptome compared to the Δrv0348 mutant (N=98 genes) are suggested to be under the positive control of the rv0348 while repressed genes (N=65) are suggested to be under its negative control. A representative sample of genes that showed transcriptional changes by DNA microarray analysis was verified by qRT-PCR. In all of the examined genes (N=10), there was an agreement of the transcriptional change (either induction or repression) between DNA microarray and qRT-PCR analyses, as shown in Table 7 and FIG. 24.

TABLE 7

Confirmation of Microarrays Data with Real-Time qRT-PCR

| Genes | qRT-PCR Δrv0348/WT | SD | Microarrays Δrv0348/WT | PDE | qRT-PCR Δrv0348::rv0348/WT | SD |
|---|---|---|---|---|---|---|
| Rv0167 | −7.69 | 0.7 | −8.9 | 1.00 | −1.38 | 0.4 |
| Rv0347 | 54.19 | 0.9 | 4.6 | 1.00 | 2.02 | 0.3 |
| Rv0569 | 42.99 | 0.3 | 6.4 | 1.00 | 1.22 | 1.7 |
| Rv0700 | −2.13 | 0.7 | −3.5 | 1.00 | −1.03 | 0.3 |
| Rv1996 | 32.60 | 0.4 | 12.7 | 1.00 | 2.89 | 0.3 |
| Rv1997 | 565.48 | 0.3 | 3.4 | 1.00 | 3.23 | 0.4 |
| Rv2032 | 169.29 | 1.2 | 3.8 | 0.99 | 3.23 | 0.5 |
| Rv2628 | 448.82 | 0.2 | 15.0 | 1.00 | 4.05 | 0.4 |
| Rv3128 | 853.16 | 0.9 | 0.0 | 0.00 | 4.05 | 0.4 |
| Rv3130c | 8.34 | 0.8 | 4.4 | 0.99 | −1.61 | 0.6 |

Figure 24:
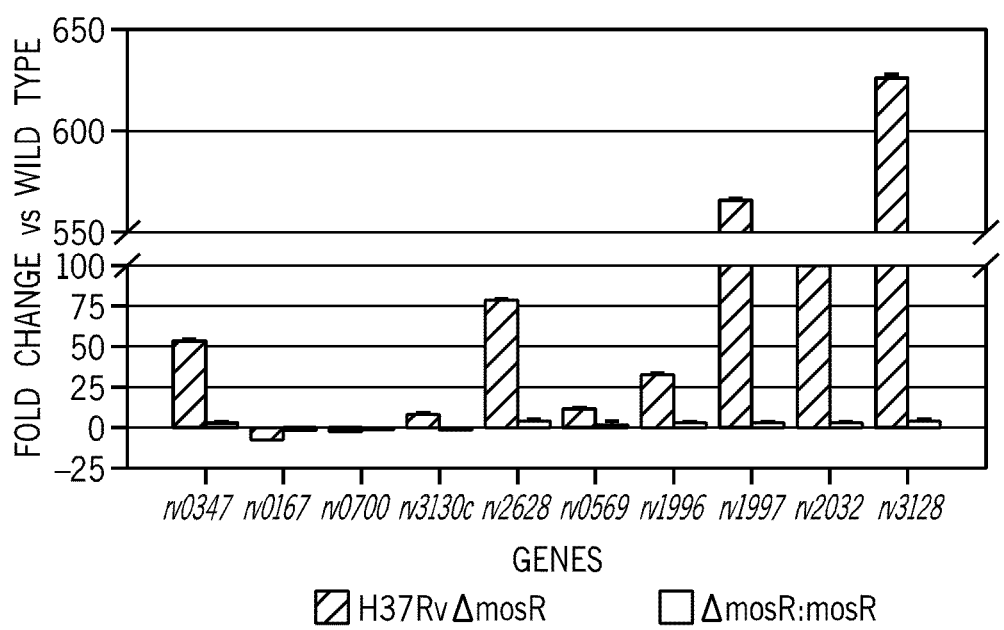
FIG. 24 shows fold changes of ten genes utilizing RNA from both mutant Δrv0348 and complemented Δrv0348::rv0348 strains relative to H37Rv wild type strain.

FIG. 24 shows fold changes of ten genes utilizing RNA from both mutant Δrv0348 and complemented Δrv0348::rv0348 strains relative to H37Rv wild type strain. Both the Δrv0348 and Δrv0348::rv0348 are represented by black and grey bars, respectively.

Figure 25:
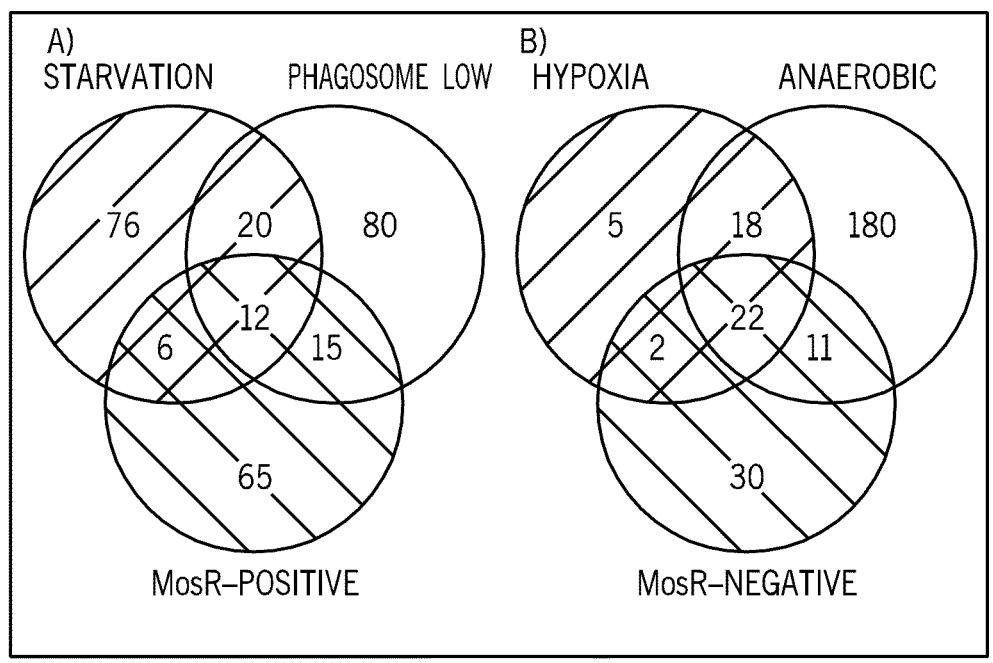
FIG. 25 shows a comparative analysis of the transcriptome of M. tb exposed to variable conditions.

Genes involved in survival during stationary and persistent phases (rpoB) of growth as well as those regulating transcription (e.g., rho, rpmE) (TubercuList database) were among genes under positive control of Rv0348. The positively-regulated operons (Table 6) included the mce1 operon (rv0167-rv0177), indicating a role for rv0348 in regulating virulence of M. tb. Other genes induced in the presence of rv0348 included a tryptophan biosynthesis gene (trpA), translation apparatus operon (fusA-tuf) and the ribosomal biosynthesis operon (rv0700-rv0723) (Table 6). Several other regulatory genes were also among the Rv0348-regulon including the hupB (encodes a DNA-binding protein) and rho (transcription termination factor). In E. coli, the expression of the tryptophan operon is regulated by inhibition of ribosomal binding sites. It is noteworthy to mention here that functional orthologues to trp operon regulatory genes are induced by rv0348 (e.g., 50S ribosomal operon, rho gene) indicating the ability of Rv0348 to exert its regulatory role(s) through transcriptional inhibition. Further comparative analysis to the starvation-induced transcriptome analyzed before identified a set of eighteen genes that are positively-regulated by Rv0348. FIG. 25(A) shows a Venn diagram representing the number of rv0348-positively regulated genes compared to genes induced under nutrient starvation (Betts et al., 2002, Mol. Microbiol., 43:717-31) and those repressed in the phagosome environment (Schnappinger, D. et al., 2003, J. Exp. Med., 198:693-704). Among the rv0348-positively regulated genes are a group of twenty-nine genes that were repressed during macrophage infection. This profile indicates the ability of M. tb to modulate levels of gene transcripts to survive the macrophage environment using a rv0348-dependent mechanism.

Rv0348-negatively regulated genes included a significant number of phagosome-activated genes (N=33). Among this group is rv3130c which encodes triglyceride synthase (tgs1), a protein that is involved in triglyceride synthesis in M. tb, indicating a role for rv0348 in regulating mycobacterial fatty acid metabolism. A set of the rv0348-negatively regulated genes (N=24) were among the 47 genes responsive to hypoxia (see, FIG. 25(B)) or to the 48 genes responsive to reactive nitrogen intermediates ("RNI") and gradual adaptation to low levels of oxygen. Additionally, a list of thirty-three genes that were activated during anaerobic growth of M. tb were also found among the rv0348-negatively regulated genes in this study. FIG. 25(B) shows a Venn diagram representing the number of rv0348-negatively regulated genes compared to genes induced under hypoxia (Park, H. D. et al., 2003, Mol. Microbiol., 48:833-43) and anaerobic conditions (Muttucumaru, D. G. N. et al., 2004, Tuberculosis, 84:239-46). Previously, a significant level of overlap existed between the hypoxia and RNI regulons and were shown to be under the two-component regulator, dosR. Transcripts for the dosR regulator did not change in the present analysis, indicating an additional and/or alternative role(s) for the set of twenty-four genes in the pathobiology of M. tb. However, the activation of the acr gene is usually considered a strong indication of the activation of the dosR regulon. The acr gene was previously confirmed to contribute to M. tb survival in macrophages, hence its inclusion under negative control of rv0348 indicates a potential role for rv0348 in down-regulating genes involved in hypoxia, in stages when they are not needed. Finally, hypergeometric distribution analysis of the Rv0348-dependent genes and each of the compared transcriptomes indicated the significant association between the rv0348-induced transcriptome and starvation, phagosome survival, hypoxia and anaerobic conditions (p<0.001), as shown in Table 8.

TABLE 8

Analysis of Groups Overrepresented in the Transcriptome of *Mycobacterium tuberculosis* as Determined by Hypergeometric Distribution

| Category | # in rv0348 Transcriptome | # in Conditions | P-value |
| --- | --- | --- | --- |
| Starvation | 16 | 114 | 9.0E−06 |
| Low in Phagosome | 27 | 127 | 3.2E−13 |
| Hypoxia | 24 | 48 | 0.0E+00 |
| Anaerobic | 33 | 231 | 6.3E−11 |

Overall, the presented analyses show the previously undiscovered, yet broad and far reaching potential regulatory roles exerted by the rv0348 in M. tb survival strategies.

3. rv0348 Expression in *M. smegmatis* Model of Hypoxia

The study of rv0348 expression under hypoxic conditions in *M. smeg*::pML21 was performed using the Wayne model of hypoxia in M. tb, which has proven equally useful in studies of *M. smegmatis*. Briefly, a single colony of *M. smeg*::pML21 (see, EXAMPLE II section B.3 for construction) harboring the rv0348 operon was grown with shaking at 37° C. to an $OD_{600}$ of 1.0 in Dubos Tween Albumin medium (BD Biosciences) supplemented with kanamycin (30 μg/ml). This culture was used to inoculate 6×30 ml screw-capped tubes containing stir bars to an $OD_{600}$ of 0.1 in Dubos media containing methylene blue (1.5 μg/ml) to serve as an indicator of oxygen levels. Three tubes were used as aerobic controls with loose caps, a head space ratio ("HSR") of 1.5, and were stirred at 200 rpm. The remaining 3 tubes were used for the anaerobic cultures with tightened, parafilm-sealed caps, an HSR of 0.5, and were stirred at 120 rpm. The color of the tubes was monitored and aerobic/anaerobic tubes were taken for analysis when the methylene blue first showed signs of fading (day 1) and after the anaerobic cultures became completely colorless (day 6 and 7). An aliquot (100 μl) of each sample was plated for colony counts while the rest was used for total RNA extraction and qRT-PCR as described above. The whole experiment was repeated 3 times.

Using the Wayne model of hypoxia in M. tb, transcripts of rv0348 operon were modestly induced under anaerobic conditions indicating the rv0348 operon's involvement in hypoxic responses. Since large number of the dormancy regulon genes were suggested to be controlled by rv0348, it is possible that rv0348 could be involved in mycobacterial hypoxic responses. To test this hypothesis, an in vitro model of hypoxia where the influence of hypoxia and anaerobic conditions on rv0348 operon could be studied in a recombinant strain *M. smegmatis* (*M. smeg*::pML21) was developed that was shown to express Rv0348, as shown in FIG. 20(A). FIG. 20 shows the transcriptional regulation of Rv0348-dependent genes in presence or absence of the rv0348 operon. Referring to FIG. 20, the * denotes significant change in a Student's t-Test (p<0.001). FIG. 20(A) shows a Western blot analysis of the recombinant strain of *M. smegmatis* mc²155 expressing Rv0348 protein. FIG. 20(B) shows the survival curve of *M. smeg*::pML21 under aerobic and anaerobic conditions (left scale) and fold change in rv0348 transcripts as measured by qRT-PCR (right scale).

Figure 26A:
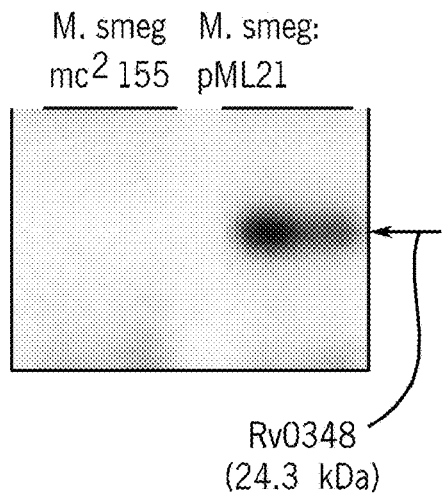
FIG. 26A-F shows Western blot analysis of the recombinant strain of M. smegmatis mc$^2$155 expressing rv0348 protein (A); the survival curve of M. smeg::pML21 under aerobic and anaerobic conditions (left scale) and fold change in mosR transcripts as measured by qRT-PCR (right scale) (B); Lac-Z repression for constructs for rv3130c promoter (C); Lac-Z repression for constructs for rv0347 (D); Lac-Z repression for constructs for rv0700 (E); Lac-Z induction for constructs for rv0167 (F) ("*" denotes significant change in a Student's t-Test (p<0.001)).
Figure 26B:
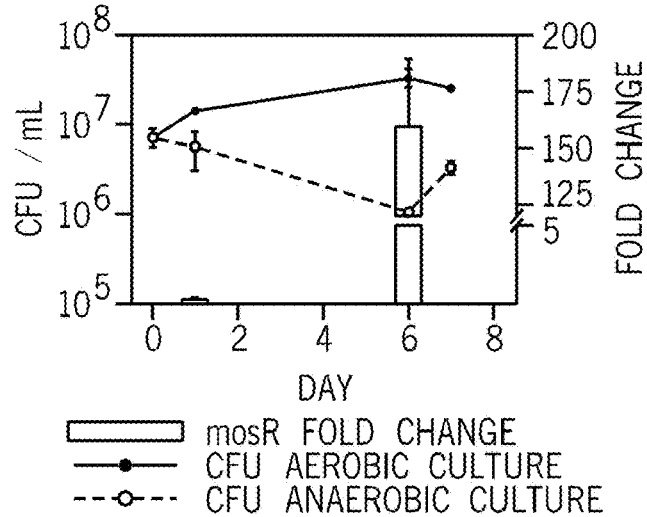
Figure 26C:
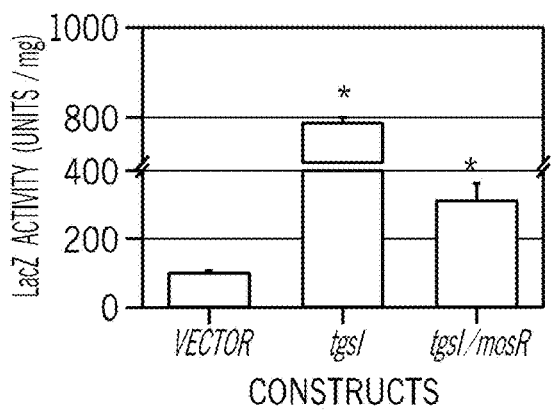
Figure 26D:
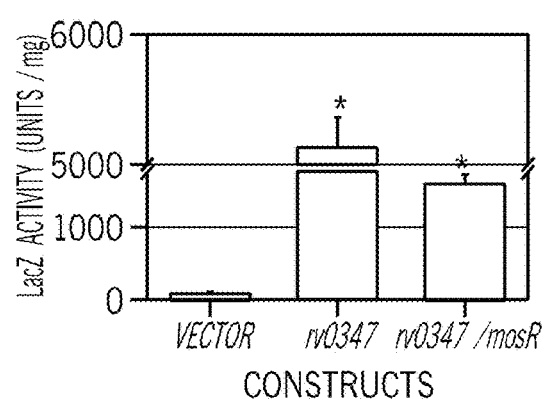
Figure 26E:
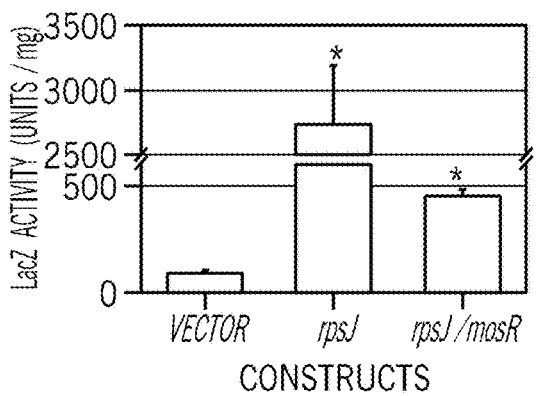
Figure 26F:
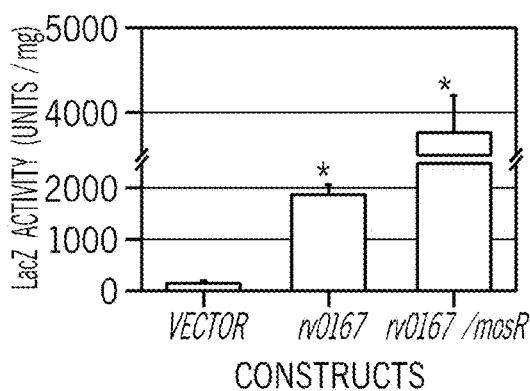

Construction of LacZ vectors and β-galactosidase assays were performed as follows. The DNA fragment corresponding to the putative promoter regions of rv3130c, rv0167, rv0700, rv0347 and hsp60 genes were cloned by PCR using gene-specific primers (Table 5). The different promoters were cloned into pML24 shuttle vector (a derivative of pCV77 vector where a hygromycin cassette was cloned into a SpeI site). *M. smegmatis* was first electroporated by pML21 and positive clones were selected and verified by PCR and Western blot to ensure the expression of Rv0348 protein. Recombinant *M. smegmatis* were electroporated with a different shuttle vector (pML24 derivative) and incubated on selective LB plates supplemented with 5-bromo-4-chloro-3-indoyl-β-D-galactopyranoside (X-Gal). All recombinant *M. smegmatis* developed blue color on plates except the negative control (pML24). Assessment of β-galactosidase activity in different constructs was performed in sonicated extracts of *M. smegmatis* strains using a β-galactosidase assay kit (Stratagene, Cedar Creek, Tex.) according to the manufacturer protocol. Experiments were carried out in triplicate and repeated twice from independent cultures with different amounts of soluble fraction proteins. β-galactosidase was expressed as Miller units/mg of soluble lysate. FIG. 26(C) shows Lac-Z repression for constructs for rv3130c promoter. FIG. 26(D) shows Lac-Z repression for constructs for rv0347. FIG. 26(E) shows Lac-Z repression for constructs of rv0700. FIG. 26(F) shows Lac-Z induction for constructs of rv0167.

BLAST analysis indicated that the rv0348 operon is absent from the genome of *M. smegmatis*, allowing for the expression of Rv0348 and assessment of its function(s) in the rapidly growing *M. smegmatis*. Using a modified version of the Wayne model of hypoxia, it was found that aerobic cultures of *M. smeg*::pML21 grew to a higher density than the anaerobic cultures, as expected (see, FIG. 26(B)). Interestingly, transcripts of rv0348 were significantly up-regulated in the cultures grown under hypoxic conditions (at day 1) with a more profound induction when cultures reach anaerobic phase by day 6 of incubation. This dramatic increase in rv0348 transcripts strongly supports the hypothesis that rv0348 participates in M. tb response to anaerobic stress, in addition to its role in M. tb survival during infection. Currently, experiments are underway to examine the survival of H37RvΔrv0348 mutant under anaerobic environment.

4. Rv0348 binding to New Promoter Regions

Figure 27A:
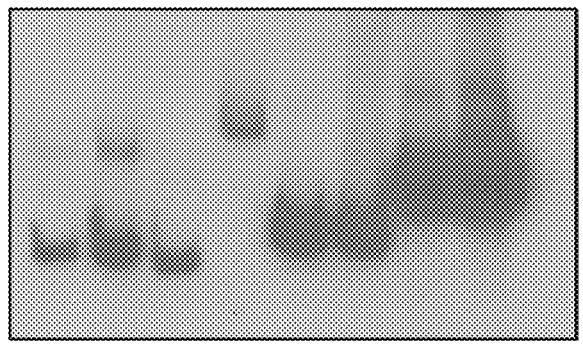
FIG. 27A-C shows results of various EMSA assays.
Figure 27B:
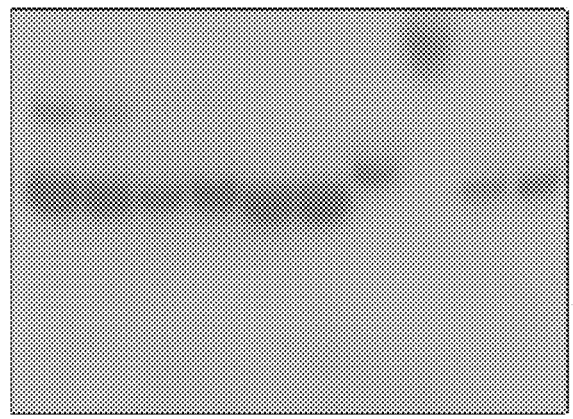
Figure 27C:
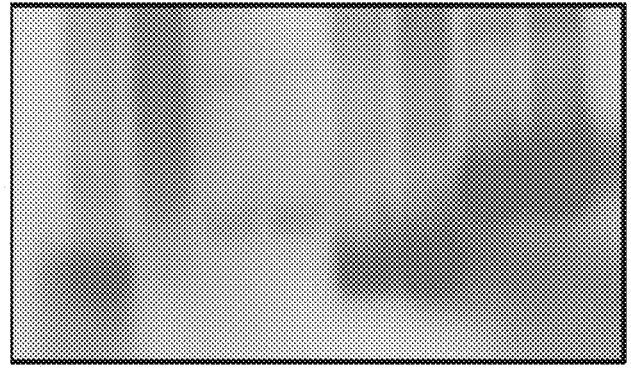

It has been shown that rv0348 encodes a transcriptional regulator that binds to its own promoter. Electrophoresis mobility shift assay ("EMSA") assays were performed using the predicted regulatory sequences of ten genes that changed their transcriptional profile based on presence/absence of intact rv0348 gene to examine the ability of Rv0348 to regulate other genes. For EMSA assays, the Rv0348 protein was purified as detailed in Talaat et al., 2007, J. Bacteriol. 189:4265-4274. Probes were generated using standard PCR amplification protocols and primers designed by Primer3 v. 0.4.0 by providing the upstream probable regulatory sequences of selected genes. Potential promoter regions of several selected genes were amplified by PCR and end-labelled by radioactive P32. The different probes were allowed to bind to recombinant MBP-Rv0348 and subsequently run on 4% native polyacrylamide gel. The gel was then dried and exposed to Kodak film. As shown in FIG. 27, the presence of Rv0348 did not impact the migration pattern of DNA fragments representing any of the ten putative promoters indicating an indirect regulatory function for Rv0348. Only when the positive control was used (upstream region of the rv0348 operon), a retardation of the DNA migration was noticeable. It is possible that other regulatory elements are needed to amplify the regulatory role(s) of rv0348.

5. Rv0348 Regulatory Functions

Because of the lack of a direct binding of Rv0348 to any of the examined genes with differential gene expression profile, the LacZ reporter gene was employed to examine the regulatory role of Rv0348. For this purpose, the generated M. smeg::rv0348 (M. smeg::pML21) construct was used to examine the transcriptional regulation of a selected list of genes that belong to rv0348-regulon. A verified clone of the M. smeg::rv0348 was electroporated with derivatives of the pML24 plasmid, listed in Table 4, where the putative promoter regions of several genes were cloned upstream of a promoterless reporter gene (lacZ).

Figure 28:
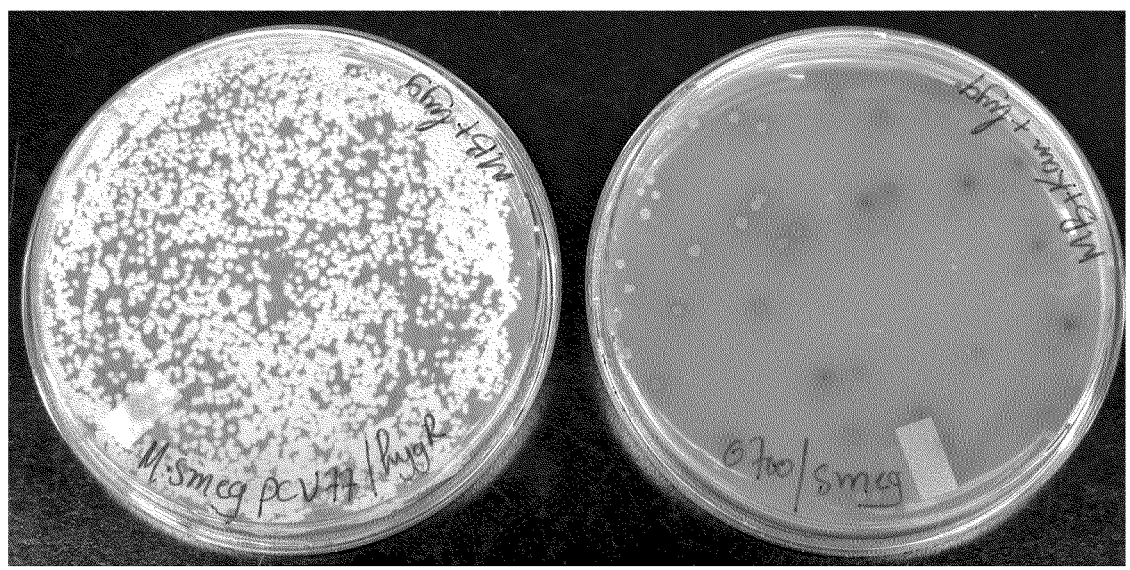
FIG. 28 shows recombinant colonies of M. smegmatis without (left) or with (right) promoters for the target genes.
Figure 29:
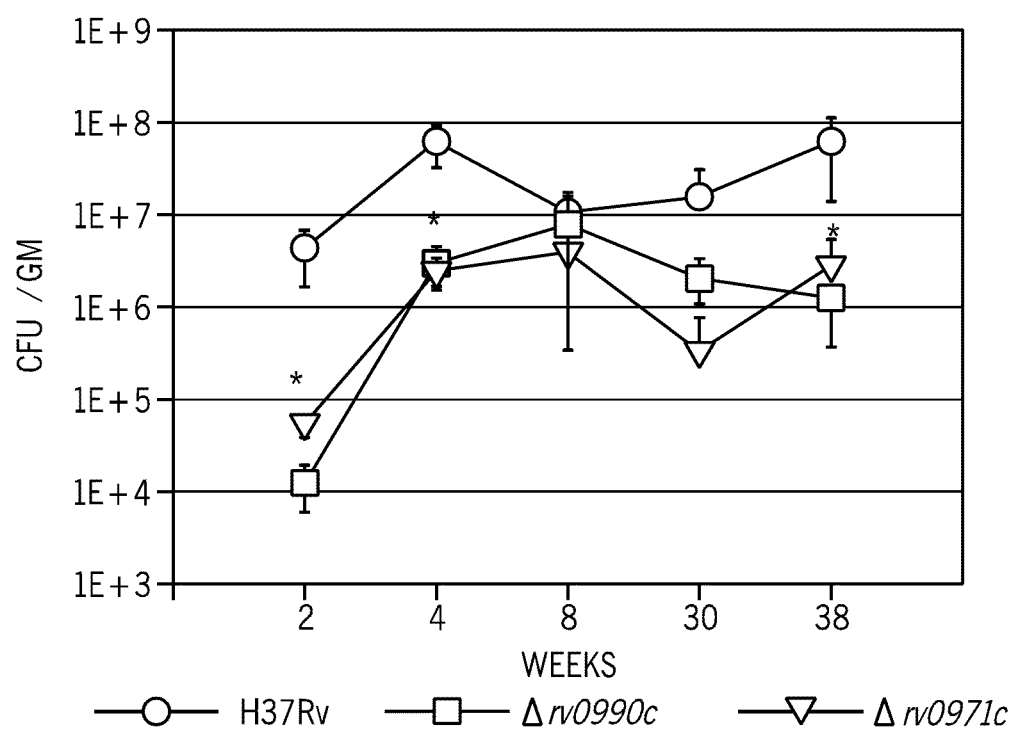
FIG. 29 shows CFU/g tissue in murine lungs at various times for H37Rv wild-type strain, Δrv0990c strain, and Δrv0971c strain.
Figure 30:
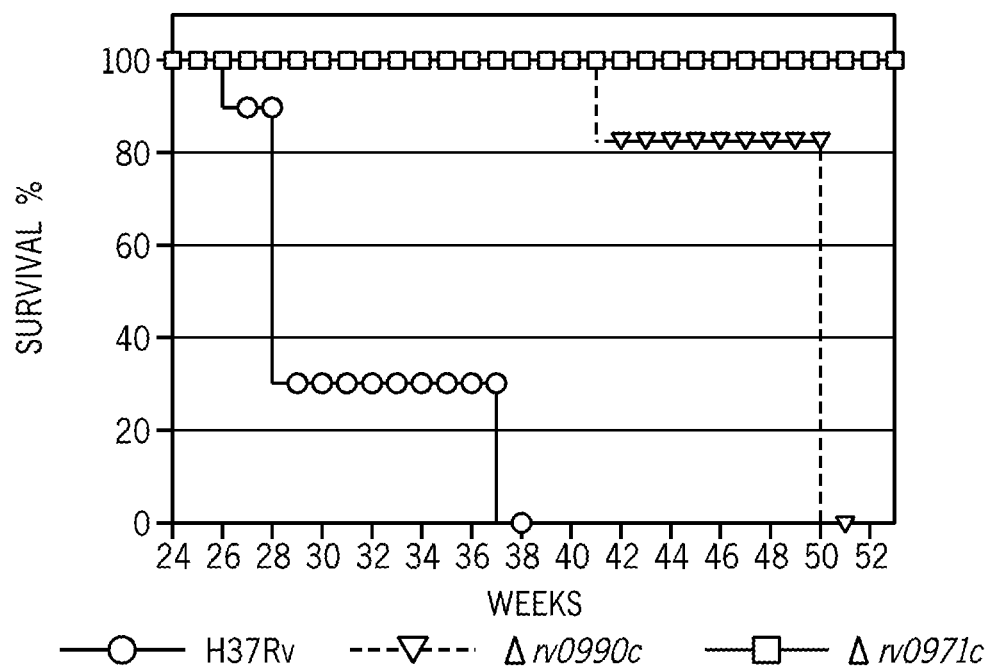
FIG. 30 shows survival curves of three mice groups infected with H37Rv wild-type strain, Δrv0990c strain, and Δrv0971c strain.
Figure 31:
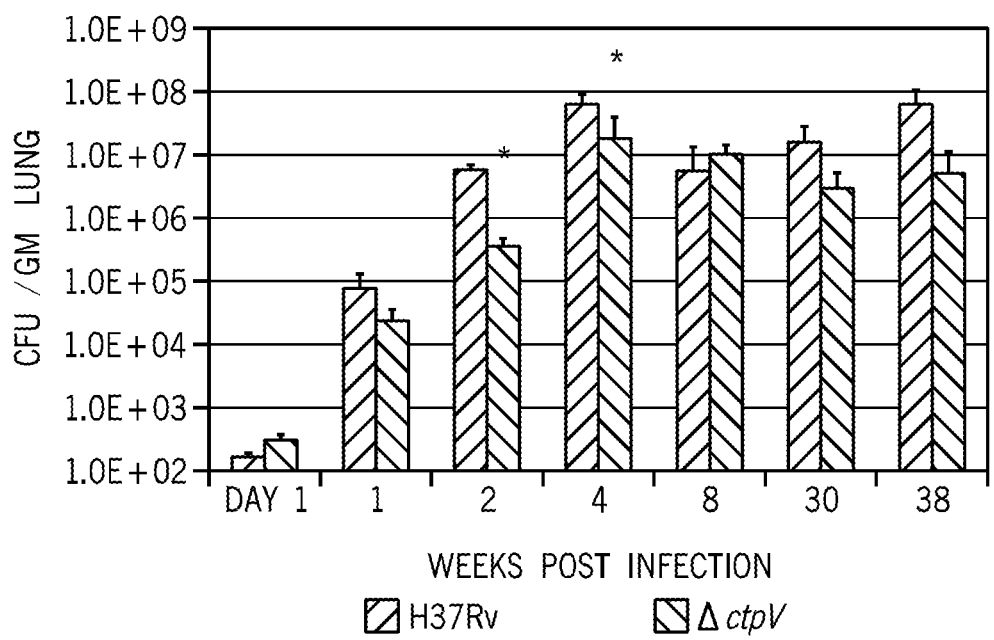
FIG. 31 shows the colonization and survival data of ΔctpV and the corresponding wild-type H37Rv M. tb strain.
Figure 35:
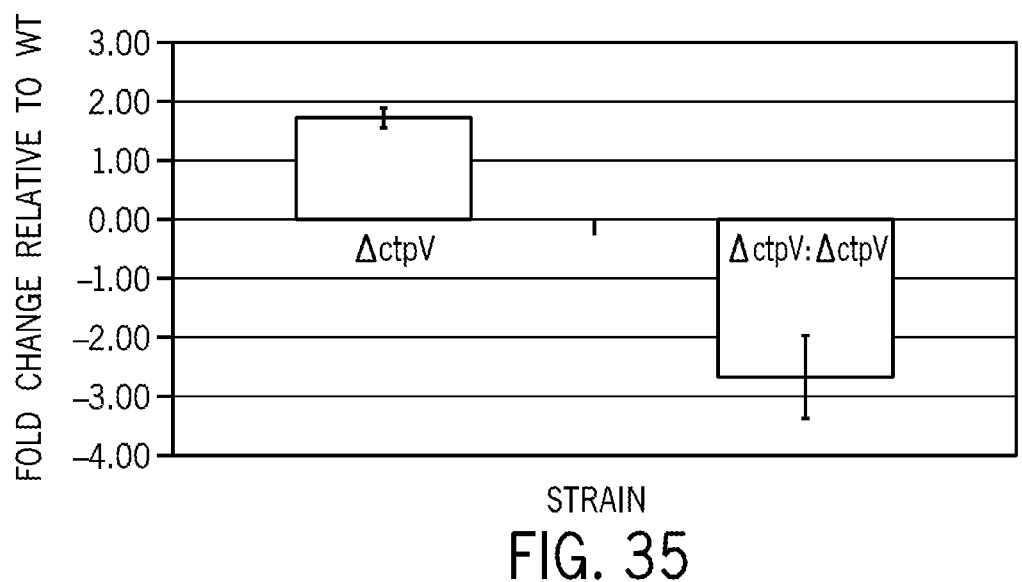
FIG. 35 is a graph showing fold change in expression of csoR at 500 μM copper in the ΔctpV mutant and the ΔctpV:ctpV mutant relative to csoR expression in the corresponding WT M. tb strain.
Figure 37:
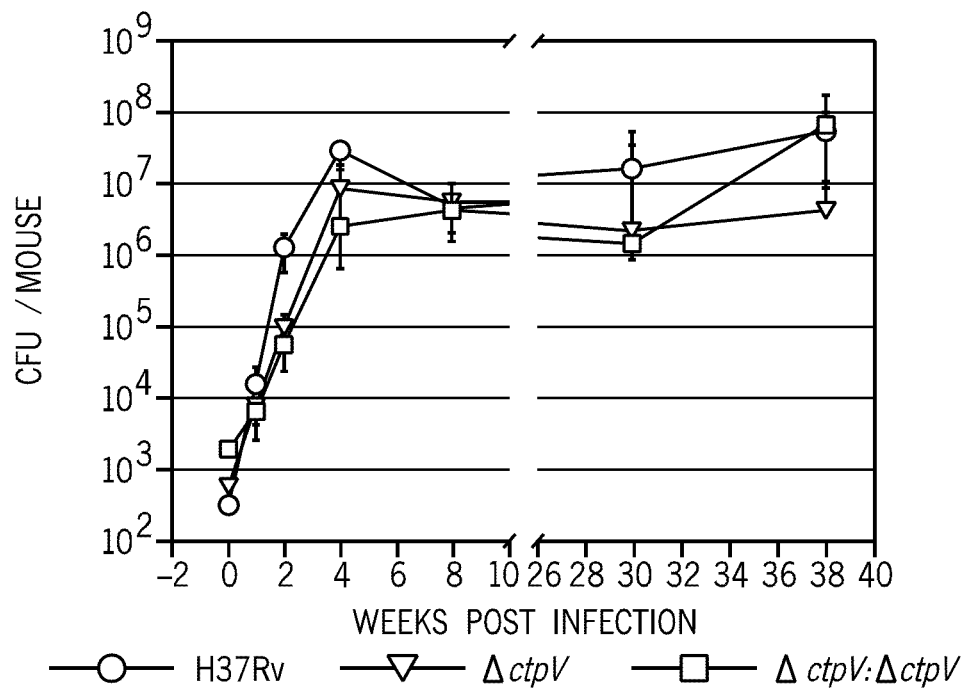
FIG. 37 shows CFU/g tissue in murine lungs at various times for H37Rv wild-type strain, ΔctpV strain, and ΔctpV::ctpV strain.
Figure 38:
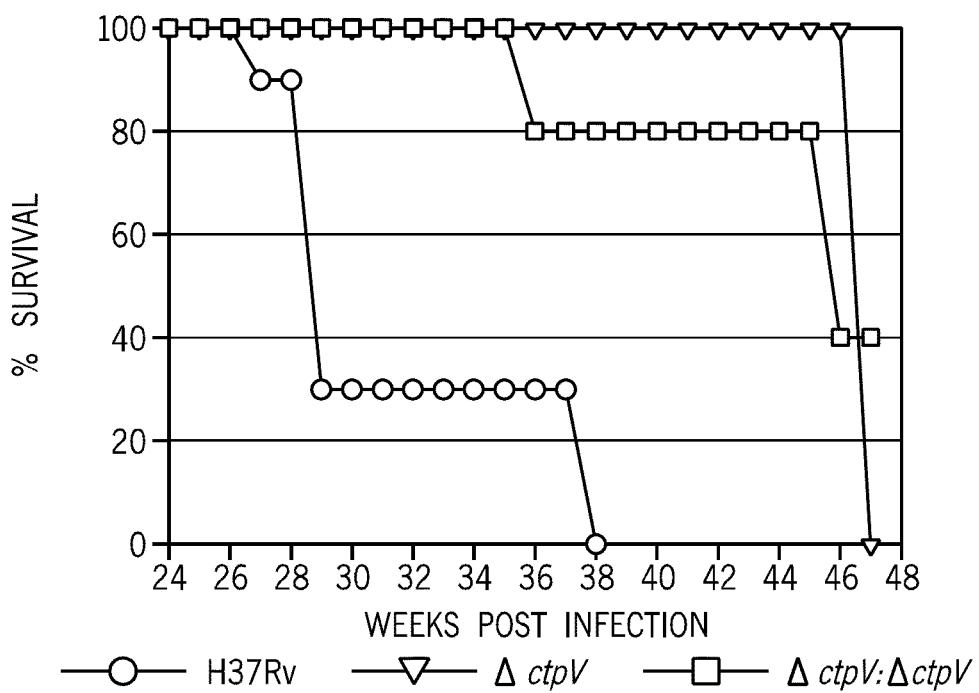
FIG. 38 shows survival curves of three mice groups infected with H37Rv wild-type strain, ΔctpV strain, and ΔctpV::ctpV strain.
Figure 39A:
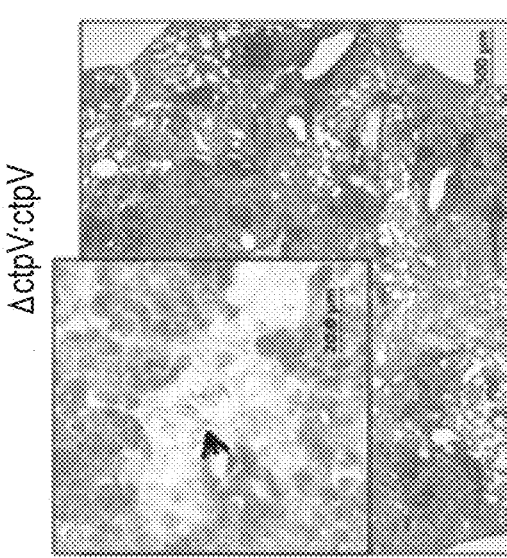
Figure 39B:
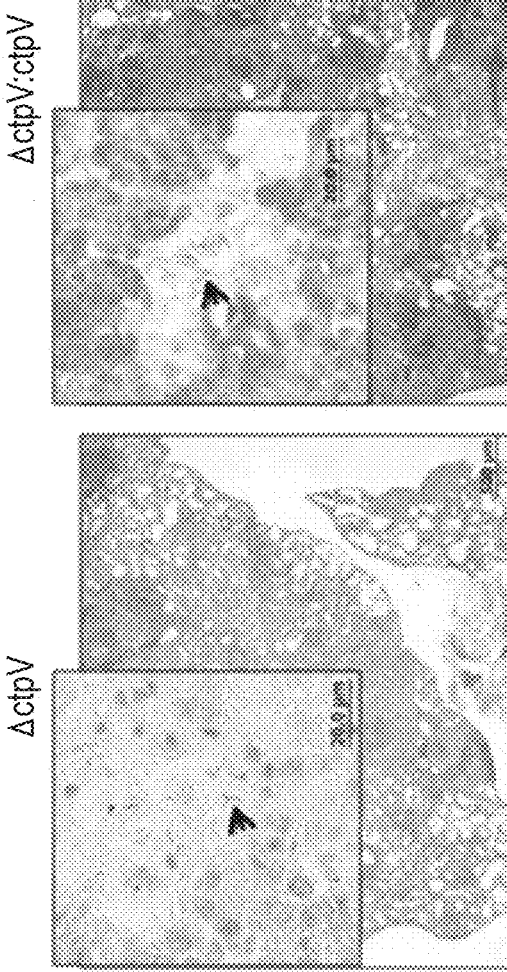
Figure 39C:
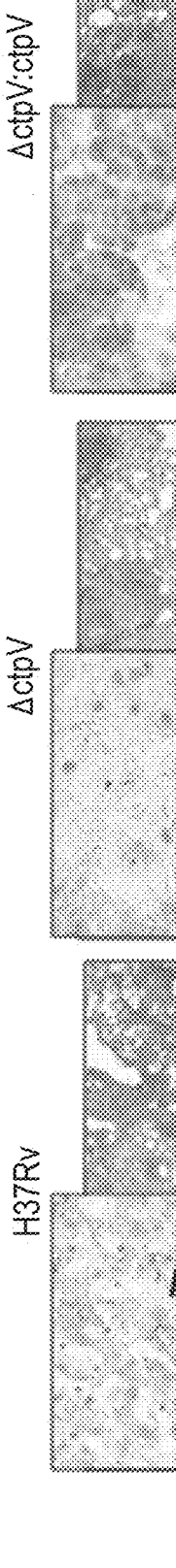
Figure 39D:
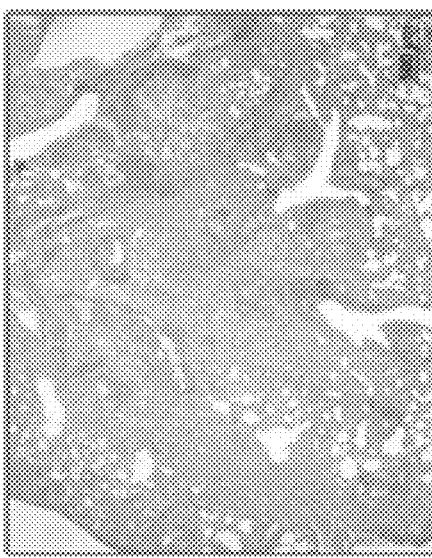
Figure 39E:
Figure 39F:
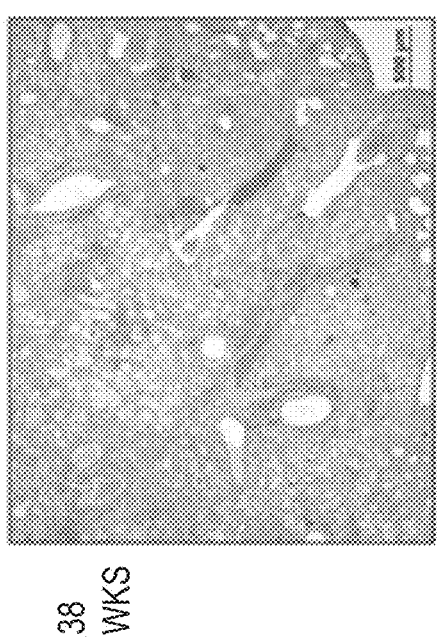
Figure 39J:
Figure 39K:
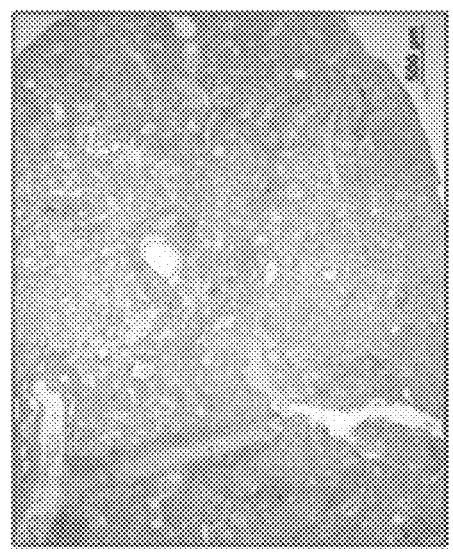
Figure 39L:
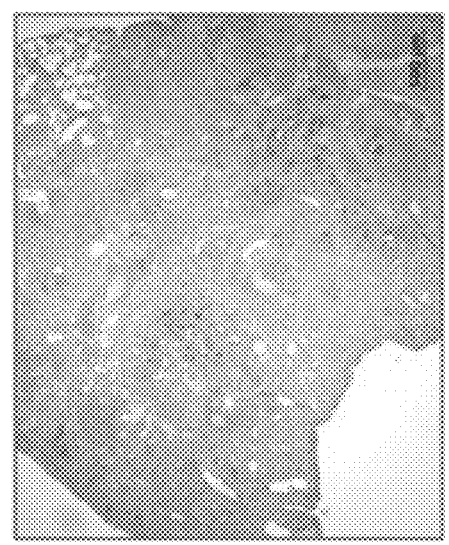

Screening of transformants showed that all constructs formed blue colonies on plates supplemented with X-Gal except when a promoterless Lac-Z vector was used for transformation (see FIG. 28). Nonetheless, quantitative analysis of β-galactosidase activity of each construct in the presence/absence of the rv0348 operon showed significant differences among constructs depending on presence of the rv0348 operon.

In all examined promoters, a significant change in the expression level of LacZ was found between constructs where the rv0348 operon was present compared to those without. Both the repression of rv0347 (promoter for rv0348) and rv3130c promoters and the induction of rv0167 (promoter for mce1) were in agreement with the negative and positive regulation by Rv0348, respectively, as indicated by DNA microarrays. However, in the case of rv0700 (promoter for ribosomal protein operon), the LacZ assay indicated its repression despite evidence that it is under positive control of Rv0348, indicating the presence of other regulatory mechanisms, besides rv0348, that control rv0700 in M. smegmatis. Interestingly, the LacZ reporter technology was able to show differential regulation for mce1, rv3130c and rv0700 genes in M. smegmatis expressing Rv0348, despite the inability of Rv0348 to bind to their putative promoter regions indicating an alternative strategy for gene regulation exerted by Rv0348.

To further confirm the regulatory role of rv0348, qRT-PCR was employed to estimate the transcript levels of regulated genes in the complemented strain, H37Rv Δrv0348::rv0348, compared to the mutant strain H37Rv Δrv0348 (see FIG. 24). Such analysis was intended to test the ability of rv0348 expression in trans to maintain the functional role(s) played by rv0348 and provide an additional confirmation of the regulatory role of Rv0348. In all examined genes, the induction/repression levels of transcripts in the Δrv0348 were consistent with DNA microarray analysis. However, transcripts in the complemented strain for the ten examined genes were restored to the wild type level (±1) confirming the regulatory role for the rv0348 gene and the success of the complementation for in vitro cultures. Overall, both the reporter assay and quantitative PCR analysis supported a regulatory role for the Rv0348 as a transcriptional factor.

Figure 40:
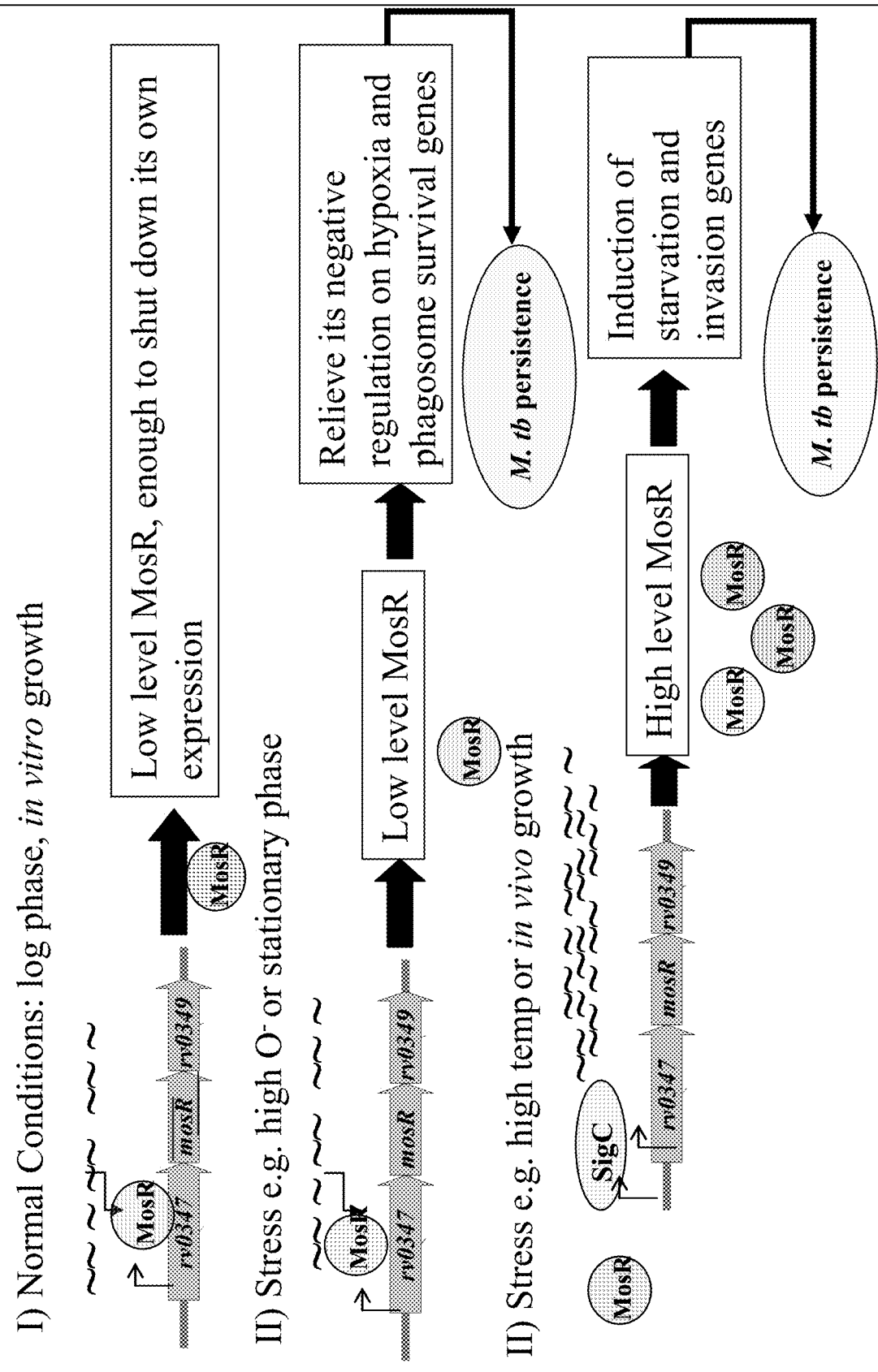
FIG. 40 shows a schematic depicting several scenarios in which rv0348 can play a role in M. tb survival strategies.

It has been shown that rv0348 encodes a transcriptional regulator with both inducer and repressor activities that are used to regulate key mycobacterial responses to stressors such as starvation and low oxygen tensions. Based on the presented analyses, a model was generated that delineates possible pathways that can be utilized by Rv0348 to explain its role in establishing chronic tuberculosis. Though not wishing to be bound by any particular theory, in this model, as depicted in FIG. 40 (a schematic depicting several scenarios in which rv0348 can play a role in M. tb survival strategies), Rv0348 can bind to its own promoter in order to maintain a low level of expression especially during log phase culture or under in vitro growth, in general. During certain stressors (e.g., high O⁻ level), the expression of Rv0348 will be even lower (see FIG. 26(B)) which will relieve its repression of other genes such as hypoxia- and phagosome-responsive genes.

During other stressors (e.g., high temp or in vivo growth), the rv0348 is induced (see FIG. 22), most likely through the activity of other transcriptional regulators (e.g. SigC) which share a transcriptional binding sites upstream of rv0348 operon. Such binding could prevent the binding of Rv0348 to its promoter, and hence, its own expression will be induced which in turn could activate genes involved in starvation and invasion among the rv0348-regulon (see, FIG. 25(A)). Under all of these scenarios (relieve of hypoxia gene repression or induction of starvation genes), the general outcome of the induction of the rv0348-regulon is the fitness of M. tb to persist under variable host microenvironments.

Example III: rv0990c Knockout Mutant

A. Overview

The rv0990c gene is the central gene of an operon of three genes (rv0989c-0991c) located in the iVEGI (see FIG. 1). Bioinformatics analysis suggested that rv0990c could be a DNA-binding protein. To investigate the role of rv0990c in the regulatory pathways and pathogenesis of M. tb, the coding sequence of rv0990c was deleted using a phage-mediated delivery technique. The animal data obtained (e.g., cfu count, histopathology, and survival curves) following aerosol infection confirmed the attenuation phenotype of Δrv0990c.

B. Construction of Δrv0990c Knockout Mutant

A knockout mutant of rv0990c, Δrv0990c, was prepared using the virulent M. tb strain H37Rv. The rv0990c gene is 657 base pairs. 490 base pairs of the coding sequence of rv0990c (from 70-560) were deleted from the genome of M. tb and replaced by the hygromycin cassette using the same phage delivery technique employed to disrupt the rv0348 gene and generate the knockout mutant. Briefly, ~800 base-pair fragments of both the upstream and downstream portion of the rv0990c gene were amplified by PCR and cloned into the pGEM-T Easy vector (Promega, Madison, Wis.). The fragments were then digested at the flanking restriction enzyme sites and ligated into pYUB854. The restriction sites used were SpeI/HindIII and XbaI/KpnI for left flank and right flank respectively.

As described for the rv0348 knockout, the pYUB845 construct was used to form specialized transduction mycobateriophages. Transduction protocols were performed as described in Bardarov et. al., 2002, *Microbiol.,* 148:3007-3017. Following 6 weeks of incubation at 37° C., hygromycin-resistant colonies were selected for further analysis.

Confirmation of the mutant genotype was performed as described previously for the ctpV and the rv0348 knockouts, using PCR and Southern blot analyses. (See also, Talaat, et al., 2000, *Am. J. Vet. Res.* 61:125-128 and Wu et al., 2007, *J. Bacteriol.* 189:7877-7886). Primers used to generate and test this mutant are shown in Table 9.

TABLE 9

Gene-Specific Primers for Construction of Δrv0990c Mutant (SEQ ID NOs: 95-102, respectively, in order of appearance)

| Primer | Sequence | Purpose |
|---|---|---|
| AMT533 | ATCACTACTAGTGATAGCGTAGCGGAGTCACC | Rv0990c flank cloning |
| AMT534 | ATCACTAAGCTTAGTGACCGGGTCGTTTTGGT | Rv0990c flank cloning |
| AMT535 | ATCACTTCTAGAGGTCCAGTCCGGGCGCAAAA | Rv0990c flank cloning |
| AMT536 | ATCACTGGTACCGAACCTTGGCTGCCGGAAGC | Rv0990c flank cloning |
| AMT926 | TGGTGGACCTCGACGACCTGCAGG | Rv0990c mutant screening |
| AMT899 | GTGGACAGCTTGGCCAAGGTCGGC | Rv0990c mutant screening |
| AMT900 | GCACGCTGGGGACTGCTCGAAC | Rv0990c mutant screening |
| AMT885 | GGAACTGGCGCAGTTCCTCTGGGG | Rv0990c mutant screening |

C. Construction of the rv0990c Complement

One of rv0990c mutants was electroporated with a copy of rv0990c gene cloned under the control of hsp60 promoter in pMV361. The transformants were verified by PCR for the construct stability M. tb. One of the complemented strains was used to infect a group of BALB/c mice to confirm the observed attenuation phenotype of the mutant.

Example IV: rv0971c Knockout Mutant

A. Overview

The rv0971c gene is the last gene of an operon of six genes located in to the iVEGI of M. tb. (See FIG. 1). Although, the exact function of rv0971c is largely unknown, it was annotated as a crotonase in the Tuberculist, and the operon is believed to play a crucial role in lipid metabolism (biosynthesis and degradation). The unique location of the operon in the M. tb pathogenicity island suggested a role in mycobacterial virulence. Attempts to delete the whole operon from the genome of M. tb were unsuccessful. Instead, the rv0971c gene was deleted and virulence of the mutant was studied in an animal model.

B. Construction of the rv0971c Knockout Mutant

The rv0971c gene is 810 base pairs. 674 base pairs of the coding sequence of rv0971c (66-740) were deleted and replaced by a hygromycin cassette using the same phage delivery technique described above for the rv0990v knockout. The mutants were verified by PCR and Southern blot techniques. The restriction sites were SpeI/HindIII and XbaI/KpnI for left and right arm respectively. Primers used to generate and test this mutant are in Table 10:

TABLE 10

Gene-Specific Primers for Construction of Δrv0971c Mutant (SEQ ID NOs: 103-110, respectively, in order of appearance)

| Primer | Sequence | Purpose |
|---|---|---|
| AMT563 | ATCACTACTAGTCAACTCACTGCGGTTACGCC | Rv0971c flank cloning |
| AMT564 | ATCACTAAGCTTATGCTGGCCTTCCTGCAGAA | Rv0971c flank cloning |
| AMT565 | ATCACTTCTAGAGCGGTTGTGCGGAGAGTTCA | Rv0971c flank cloning |
| AMT566 | ATCACTGGTACCGACTGGATCATCAAGGGCCA | Rv0971c flank cloning |
| AMT885 | GGAACTGGCGCAGTTCCTCTGGGG | Rv0971c mutant screening |
| AMT897 | GTTCTCCTCGGTCAGCGTGGTGAC | Rv0971c mutant screening |
| AMT926 | TGGTGGACCTCGACGACCTGCAGG | Rv0971c mutant screening |
| AMT898 | AAGATCACCACCACCGCGCGTC | Rv0971c mutant screening |

C. Construction of the rv0971c Complement

One of the verified mutants was electroporated with a functional copy of rv0971c under hsp60 promotor control, in the integrative shuttle vector pMV361. The complementation study is in progress.

Example V: Evaluation of Wild-Type M. Tb Strain H37Rv and M. Tb Knockout Mutants BALB/c mice can be infected with an M. tb knockout mutant (e.g., Δrv0990c and/or Δrv0971c) or corresponding wild-type M. tb using a low-dose aerosolization protocol. Bacterial survival and mouse lung pathology can be measured at short-term as well as long-term time points via the homogenization and plating of infected lung tissue as well as organ histology. Additionally, mice infected with the M. tb strains can be monitored over the long-term course of the infection and the survival of the infected mice can be recorded.

Briefly, BALB/c mice (Harlan, Indianapolis, Ind.) can be infected in a Glas-Col chamber (Glas-Col, LLC, Terra Haute, Ind.) loaded with 10 mL of an M. tb knockout mutant such as Δrv0990c and/or Δrv0971c, or the corresponding wildt-type M. tb strain at OD 0.30. Infectious dose of approximately 300 CFU/animal can be confirmed via a 1-day time point. CFUs can be determined at different time points (e.g., 2 weeks, 4 weeks, and 38 weeks, etc.) by homogenizing lung tissue in PBS buffer and plating on Middlebrook 7H10+10% ADC, followed by incubation at 37° C. for one month. Final CFUs can be normalized to the weight of the lung tissue used. Sections of lung, liver, and spleen tissue can be taken and incubated in formalin prior to sectioning and staining with H&E and AFS. Histopathology slides can be examined and scored by a pathologist not associated with the study.

Example VI: A 0990c Infected Mice

Three groups of mice were infected with 40990c M. tb knockout mutant as describe above in Example V. The progression of the disease was monitored in the three groups of infected mice by cfu count and survival curves. As shown in FIG. 29, a decrease in CFUs of a Δrv0990c knockout mutant (derived from M. tb strain H37RV) relative to the corresponding WT H37Rv strain was observed at both short-term and long-term time points. Referring to FIG. 29, the bacterial load of mice after infection with either wild-type (H37Rv) or its isogenic mutant Δrv0990c was determined at 2, 4, 8, 30 and 38 weeks.

Mice infected with Δrv0990c lived longer than mice infected with the wild-type H37Rv strain, resulting in an increase in time to death, as shown in FIG. 30. Referring to FIG. 30, the survival of mouse groups after infection with WT or Δrv0990c is shown.

Example VII: A 0971c Infected Mice

Two groups of mice were infected with wild-type and Δrv0971c with aerosol challenge as described above in Example V, and the cfu count and survival were monitored in the two groups. As shown in FIG. 29, a decrease in lung CFUs of a Δrv0971c knockout mutant (derived from M. tb strain H37Rv) relative to the corresponding H37Rv WT strain was observed at both short-term and long-term time points. Referring to FIG. 29, the bacterial load infection with either wild type (H37Rv) or its isogenic mutant Δrv0971c was determined at 2, 4, 8, 30 and 38 weeks.

Mice infected with Δrv0971c lived longer than mice infected with WT, as shown in FIG. 30. Referring to FIG. 30, the survival of mouse groups after infection with WT or Δrv0971c is shown.

Example VIII: Knockout Mutants Used to Generate an Immune Response in Mammals and as Vaccines Live attenuated mutants can be used as vaccines candidates against tuberculosis. Additionally, genetic vaccines based on the targeted genes can be used to develop a genetic immunization protocol that can elicit protection against tuberculosis.

In a typical immunization experiment, hosts (e.g. mice or non-human primates) will be immunized with the attenuated mutants. At 4 weeks post infection, sera or organ tissues can be collected from inoculated animals to evaluate the generated immune responses. Both humoral and cellular-based assays can be used to evaluate the host responses to immunization.

Although humoral and cellular assays can estimate the level of immunity generated following vaccination, it will not provide estimate of the level of protection offered by each vaccine construct. To estimate the protective power of vaccine candidates, immunized animals can be challenged by aerosolization of the virulent strain of *M. tuberculosis*. The readout of such assays includes animal survival curves, the level of organ colonization with the virulent strain of *M. tuberculosis* as well as immunological and histopathological responses elicited by challenge.

A. Vaccination and challenge of guinea pigs: Female Dunkin-Hartley guinea pigs (350-450 g) free of infection can be used. Four groups of ten guinea pigs can be immunized with 75 μl of a $5\times10^4$ CFU live knockout mutant formulation subcutaneously in the nape of the neck. Group I can be immunized with the ΔctpV mutant; Group II can be immunized with the Δrv0348 mutant; Group III can be immunized with the Δrv0990c mutant, and Group IV can be immunized with the Δrv0971c mutant. A control groups of 10 guinea pigs can be vaccinated with a $5\times10^4$ CFU live BCG Pasteur formulation, and a control group of 10 guinea pigs can be injected with saline. Five weeks after vaccination, all but two guinea pigs (the controls) from each group can be challenged aerogenically with a live suspension of M. tb strain H37Rv to achieve an inhaled retained dose in the lungs of approximately 300 organisms.

B. Vaccination and challenge of guinea pigs: Female Dunkin-Hartley guinea pigs (350-450 g) free of infection can be used. Four groups of ten guinea pigs can be immunized with 75 μl of a $5\times10^4$ CFU live knockout mutant formulation subcutaneously in the nape of the neck. Group I can be immunized with the ΔctpV mutant; Group II can be immunized with the Δrv0348 mutant; Group III can be immunized with the Δrv0990c mutant, and Group IV can be immunized with the Δrv0971c mutant. A control groups of 10 guinea pigs can be vaccinated with a $5\times10^4$ CFU live BCG Pasteur formulation, and a control group of 10 guinea pigs can be injected with saline. Five weeks after vaccination, the guinea pigs can vaccinated as described above, but with 50% of the CFUs. Five weeks after the second vaccination, all but two guinea pigs (the controls) from each group can be challenged aerogenically with a live suspension of M. tb strain H37Rv to achieve an inhaled retained dose in the lungs of approximately 300 organisms.

C. Testing for an immune response in vaccinated guinea pigs: Prior to exposure to the infectious M. tb strain H37Rv., a blood sample can be taken from each of the guinea pigs, including vaccinated and saline-injected, and the presence or absence of antibodies directed to M. tb can be determined by methods known in the art.

D. Post mortem examination of guinea pigs: Guinea pigs can be sacrificed according to institutional protocol after 20 weeks. Tissues of interest (e.g., lung, spleen, etc.) can be harvested immediately after death and analyzed for M. tb colonization.

E. Bacterial enumeration: CFUs can be determined by homogenizing lung tissue in PBS buffer and plating on Middlebrook 7H10+10% ADC, followed by incubation at 37° C. for one month. Final CFUs can be normalized to the weight of the lung tissue used. Sections of lung, liver, and spleen tissue can be taken and incubated in formalin prior to sectioning and staining with H&E and AFS. Histopathology slides can be examined and scored by a pathologist not associated with the study.

F. Results: Guinea pigs from Groups I-IV and control guinea pigs vaccinated with BCG Pasteur formulation are expected to have developed antibodies directed to M. tb.

Additionally, guinea pigs from these groups are expected to live longer and have fewer CFUs in organs and tissues tested, post infection, as compared to guinea pigs injected with saline. Additionally, further challenges of vaccinated guinea pigs with infectious M. tb strains is expected to result in less sever symptoms. For example, re-challenged guinea pigs are expected to exhibit an increased post-infection life span and fewer CFUs in lung, liver and spleen than non-vaccinated guinea pigs. Similar results are expected with the "boosted" guinea pigs described in section VIII.B.

In contrast, no or very low titer antibodies directed to M. tb are expected in the saline-injected guinea pigs. Moreover, subjects in this test group are expected to die due to the M. tb infection at about 38 weeks post infection.

Example IX: ΔctpV Infected Mice

Three groups of mice were infected with ΔctpV M. tb knockout mutant as described above in Example V. BALB/c mice (Harlan Laboratories, Inc., Indianapolis, Ind., USA) were infected in a Glas-Col chamber (Glas-Col, LLC, Terra Haute, Ind., USA) loaded with 10 ml of either ΔctpV or wildtype bacteria at $OD_{600}$ 0.30. Infectious dose of approximately 300 CFU/animal was confirmed via a 1-day time-point. CFUs were determined by homogenizing lung tissue in PBS buffer and plating on Middlebrook 7H10+10% ADC, followed by incubation at 37° C. for one month. For the survival curve, animals were monitored daily by animal care staff not associated with the study. As specified in our animal protocol, mice were sacrificed after being identified by our animal care staff as morbidly ill, using criteria such as haunched posture, extreme weight loss, and slow or pained movements. Sections of lung, liver, and spleen tissue were taken and incubated in formalin prior to sectioning and staining with hematoxylin and eosin (H&E) and acid-fast staining (AFS). Histopathology slides were examined and scored by a pathologist not associated with the study. For immunohistochemistry, the primary antibody, rabbit anti-interferon gamma (Invitrogen), was diluted 1:1000 in Van Gogh Yellow antibody diluent (Biocare Medical, Concord, Calif., USA) and incubated for one hour. Negative control slides received only diluent in lieu of antibody. Primary antibody was detected using biotinylated goat anti-rabbit IgG secondary antibody (Biocare Medical) and Streptavidin-horseradish peroxidase (Biocare Medical). Staining was visualized with DAB+(diaminobenzidine) (Dako, Glostrup, Denmark) and counterstained with CAT hematoxylin (Biocare Medical) mixed 1:1 with distilled water.

The ctpV gene is part of a 29-gene genomic island previously shown to be preferentially induced in mice relative to in vitro culture (termed the in vivo expressed genomic island, iVEGI). This suggested that ctpV might play a role specific to the in vivo lifestyle of Mtb. In addition, experiments showed that CtpV is a copper exporter, and data suggest that copper homeostasis in bacteria may play a role in pathogenesis, although this had never been tested in Mtb. To investigate this hypothesis, groups of BALB/c mice (n=30-40) were infected with H37Rv, ΔctpV, or ΔctpV::ctpV using a low-dose aerosolization protocol. Bacterial colony counts from mouse lung tissue over the course of the infection revealed that, overall, bacterial survival between the three strains over the course of infection was similar, and differences in colonization levels did not reach statistical significance at any time point (FIG. 37).

FIG. 37 shows bacterial colonization of mouse lungs after aerosol infection with either wild-type H37Rv, its isogenic mutant ΔctpV, or the complemented strain ΔctpV::ctpV. CFUs were determined via homogenization of lungs from infected mice (N=3-5 per time point) in PBS and plating on 7H10+ADC, with hygromycin added in the case of the mutant and complemented strain. CFUs were normalized to grams of lung tissue homogenized. Colonization levels between the three strains did not display a statistically significant difference over the course of the infection. The experiment was performed twice, with a representative experiment shown.

Survival of mouse groups after aerosol infection with H37Rv, ΔctpV, or ΔctpV::ctpV is shown in FIG. 38. Survival is displayed as the time from infection (week 0) until the time declared morbid by animal care staff. Morbid mice were subsequently euthanized, with tuberculosis determined as the cause of illness via necropsy. A log-rank statistical test was used to analyze survival of mice groups. Survival of mice infected with H37Rv was significantly different from those infection with ΔctpV (p-value=0.002), and those infected with survival was ΔctpV::ctpV strain (p-value=0.02). Experiment was performed once with 10 mice/group.

In contrast to the similarity in bacterial load of the mice infected with H37Rv, ΔctpV, and ΔctpV::ctpV, the mice infected with ΔctpV lived significantly longer than mice infected with wild type, with 16-week increase in time to death of mice infected with ΔctpV versus mice infected with H37Rv (FIG. 38 shows survival curves of three mice groups infected with H37Rv wild-type strain, ΔctpV strain, and ΔctpV::ctpV strain). In fact, the median survival time for mice infected with H37Rv was 31 weeks, versus 47 weeks for mice infected with ΔctpV and 42 weeks for mice infected with ΔctpV::ctpV. As determined by a log-rank statistical test (Ref), survival was significantly different between the H37Rv and ΔctpV infection (p-value=0.002), and survival was also significantly different between the H37Rv and ΔctpV::ctpV infection (p-value=0.02).

FIG. 39 shows histological (A-F) and immunohistochemisty (G-L) analysis of lung sections of mice lungs at 8 or 38 weeks post infection with wild-type ("WT") M. tb and ΔctpV and ΔctpV::ctpV. Hematoxylin and eosin (H&E) stained mouse lung tissue (40× magnification) throughout the infection show increased lung damage of the mice infected with H37Rv and ΔctpV::ctpV relative to mice infected with ΔctpV FIG. 39 A-F shows representative images at 8 and 38 weeks post-infection. Inset images (1000× magnification) show the Mtb bacilli (arrow heads) which were visible in lung tissue starting from 8 weeks forward. Immunohistochemisty of infected lung tissue at variable times of infection is shown in FIG. 39G-L. Lung tissue was sectioned and stained with antibody for mouse IFN-γ, which appears brown in the images (40× magnification). Inset images show 200× magnification of lesions displaying IFN-γ expression.

Despite carrying similar levels of bacteria throughout the infection, histology staining of the infected mouse tissue revealed consistently lower levels of tissue damage in mice infected with ΔctpV versus the wild-type and complemented strains. For example, at 8 weeks post-infection, lung tissue from mice infected with ΔctpV displayed granulomatous inflammation, whereas mice infected with H37Rv displayed massive granulomatous inflammation with more lymphocytic infiltration (FIG. 39 A-F). By 38 weeks post-infection, granulomas became more developed (presence of giant cells) and occupied almost the whole lungs of mice infected with H37Rv, compared to only 50% of tissues of mice infected with the ΔctpV mutant. Lesions observed in the complemented strain were very similar to those observed in mice infected with H37Rv strain. Overall, animal survival and histopathological data indicated the attenuation of the ΔctpV mutant compared to other tested strains.

Lung pathology in tuberculosis is thought to be caused mainly by the host immune response. In order to investigate a possible mechanism for the decreased lung pathology and increased survival time of mice infected with ΔctpV relative to H37Rv and ΔctpV::ctpV, the lung sections were stained with an antibody against mouse interferon-γ, a key cytokine known to be highly expressed during tuberculosis infection. As expected, no indication of IFN-γ expression was seen at 2 weeks post infection, prior to the start of the adaptive immune response (data not shown). However, by 8 weeks post infection, mice infected with H37Rv show significant IFN-γ expression, localized in areas of lung tissue damage, yet mice infected with ΔctpV showed only small amounts of IFN-γ expression (FIG. 39G-L). Mice infected with ΔctpV::ctpV showed an intermediate level of IFN-γ expression. Interestingly, even at the 38 week time point where mice infected with ΔctpV display large amounts of tissue damage, there was still little expression of IFN-γ relative to mice infected with H37Rv.

TABLE 11

| No. | Gene_ID | Product | Function_Class | Foldchange (Mutant/WT) | GG_PDE | Functional category |
|---|---|---|---|---|---|---|
| Positive Regulation | | | | | | |
| 1 | Rv0006 | gyrA | DNA gyrase subunit A | −2.5 | 0.92 | 2 |
| 2 | Rv0007 | | conserved hypothetical protein | −2.0 | 0.49 | 3 |
| 3 | Rv0058 | dnaB | DNA helicase (contains intein) | −2.4 | 0.88 | 2 |
| 4 | Rv0108c | | hypothetical protein | −2.4 | 0.87 | 16.6 |
| 5 | Rv0145 | | conserved hypothetical protein | −2.7 | 0.97 | 10.5 |
| 6 | Rv0166 | fadD5 | acyl-CoA synthase | −4.2 | 1.00 | 1 |
| 7 | Rv0167 | yrbE1A | part of mce1 operon | −8.9 | 1.00 | 0 |
| 8 | Rv0168 | yrbE1B | part of mce1 operon | −2.0 | 0.50 | 0 |
| 9 | Rv0169 | mce1 | part of mce1 operon, cell invasion protein | −5.1 | 1.00 | 0 |
| 10 | Rv0170 | mce1B | part of mce1 operon | −7.2 | 1.00 | 0 |
| 11 | Rv0171 | mce1C | part of mce1 operon | −13.3 | 1.00 | 0 |
| 12 | Rv0172 | mce1D | part of mce1 operon | −5.0 | 1.00 | 0 |
| 13 | Rv0173 | lprK | part of mce1 operon | −3.0 | 0.99 | 0 |
| 14 | Rv0174 | mce1F | part of mce1 operon | −5.0 | 1.00 | 0 |
| 15 | Rv0175 | | conserved hypothetical protein (mce1) | −2.0 | 0.55 | 3 |
| 16 | Rv0176 | | conserved hypothetical protein (mce1) | −2.2 | 0.69 | 3 |
| 17 | Rv0177 | | conserved hypothetical protein (mce1) | −4.0 | 1.00 | 10.5 |
| 18 | Rv0249c | | probable membrane anchor protein | −2.2 | 0.71 | 7 |
| 19 | Rv0364 | | conserved hypothetical protein | −2.2 | 0.74 | 3 |
| 20 | Rv0430 | | hypothetical protein | −3.7 | 1.00 | 10.5 |
| 21 | Rv0469 | umaA1 | unknown mycolic acid methyltransferase | −2.3 | 0.52 | 1 |
| 22 | Rv0635 | | conserved hypothetical protein | −3.1 | 0.99 | 10.5 |
| 23 | Rv0636 | | hypothetical protein | −2.6 | 0.85 | 7 |
| 24 | Rv0637 | | conserved hypothetical protein | −2.2 | 0.69 | 10.5 |
| 25 | Rv0642c | mmaA4 | methoxymycolic acid synthase 4 | −2.1 | 0.41 | 1 |
| 26 | Rv0667 | rpoB | [beta] subunit of RNA polymerase | −2.4 | 0.91 | 2 |
| 27 | Rv0684 | fusA | elongation factor G | −2.7 | 0.98 | 2 |
| 28 | Rv0685 | tuf | elongation factor EF-Tu | −3.7 | 1.00 | 2 |
| 29 | Rv0700 | rpsJ | 30S ribosomal protein S10 | −3.5 | 1.00 | 2 |
| 30 | Rv0701 | rplC | 50S ribosomal protein L3 | −4.7 | 1.00 | 2 |
| 31 | Rv0703 | rplW | 50S ribosomal protein L23 | −4.1 | 1.00 | 2 |
| 32 | Rv0704 | rplB | 50S ribosomal protein L2 | −10.1 | 1.00 | 2 |
| 33 | Rv0705 | rpsS | 30S ribosomal protein S19 | −9.5 | 1.00 | 2 |
| 34 | Rv0708 | rplP | 50S ribosomal protein L16 | −2.4 | 0.66 | 2 |
| 35 | Rv0709 | rpmC | 50S ribosomal protein L29 | −4.2 | 1.00 | 2 |
| 36 | Rv0710 | rpsQ | 30S ribosomal protein S17 | −6.2 | 1.00 | 2 |
| 37 | Rv0718 | rpsH | 30S ribosomal protein S8 | −3.0 | 0.99 | 2 |
| 38 | Rv0719 | rplF | 50S ribosomal protein L6 | −5.0 | 1.00 | 2 |
| 39 | Rv0721 | rpsE | 30S ribosomal protein S5 | −2.4 | 0.91 | 2 |
| 40 | Rv0723 | rplO | 50S ribosomal protein L15 | −2.1 | 0.58 | 2 |
| 41 | Rv0988 | | conserved hypothetical protein | −2.1 | 0.65 | 3 |
| 42 | Rv1182 | papA3 | PKS-associated protein, unknown function | −5.3 | 1.00 | 1 |

TABLE 11-continued

| No. | Gene_ID | Product | Function_Class | Foldchange (Mutant/WT) | GG_PDE | Functional category |
|---|---|---|---|---|---|---|
| 43 | Rv1183 | mmpL10 | conserved large membrane protein | −2.6 | 0.96 | 3 |
| 44 | Rv1184c | | conserved hypothetical protein | −3.4 | 1.00 | 3 |
| 45 | Rv1185c | fadD21 | acyl-CoA synthase | −2.1 | 0.49 | 1 |
| 46 | Rv1198 | | conserved hypothetical protein | −2.0 | 0.03 | 3 |
| 47 | Rv1297 | rho | transcription termination factor rho | −2.4 | 0.82 | 2 |
| 48 | Rv1298 | rpmE | 50S ribosomal protein L31 | −2.0 | 0.33 | 2 |
| 49 | Rv1535 | | hypothetical protein | −2.1 | 0.58 | 16.6 |
| 50 | Rv1613 | trpA | tryptophan synthase [alpha] chain | −2.5 | 0.92 | 7 |
| 51 | Rv1614 | lgt | prolipoprotein diacylglyceryl transferase | −4.6 | 1.00 | 3 |
| 52 | Rv1643 | rplT | 50S ribosomal protein L20 | −2.5 | 0.93 | 2 |
| 53 | Rv1794 | | conserved hypothetical protein | −2.0 | 0.46 | 10.5 |
| 54 | Rv1810 | | conserved hypothetical protein | −4.4 | 1.00 | 10.5 |
| 55 | Rv1826 | gcvH | glycine cleavage system H protein | −2.5 | 0.92 | 7 |
| 56 | Rv1883c | | conserved hypothetical protein | −2.4 | 0.70 | 10.5 |
| 57 | Rv1886c | fbpB | antigen 85B, mycolyltransferase | −2.3 | 0.80 | 1 |
| 58 | Rv2067c | | conserved hypothetical protein | −2.1 | 0.60 | 10.5 |
| 59 | Rv2080 | lppJ | lipoprotein | −2.7 | 0.98 | 3 |
| 60 | Rv2147c | | hypothetical protein | −2.2 | 0.22 | 10.5 |
| 61 | Rv2190c | | putative p60 homologue | −3.1 | 1.00 | 0 |
| 62 | Rv2391 | nirA | probable nitrite reductase/sulphite reductase | −3.5 | 1.00 | 7 |
| 63 | Rv2392 | cysH | 3'-phosphoadenylylsulfate (PAPS) reductase | −3.5 | 1.00 | 7 |
| 64 | Rv2441c | rpmA | 50S ribosomal protein L27 | −2.2 | 0.65 | 2 |
| 65 | Rv2840c | | conserved hypothetical protein | −2.3 | 0.72 | 10.5 |
| 66 | Rv2928 | tesA | thioesterase | −2.0 | 0.53 | 1 |
| 67 | Rv2948c | fadD22 | acyl-CoA synthase | −2.8 | 0.98 | 1 |
| 68 | Rv2949c | | hypothetical protein | −16.1 | 1.00 | 10.5 |
| 69 | Rv2950c | fadD29 | acyl-CoA synthase | −3.2 | 1.00 | 1 |
| 70 | Rv2959c | | some similarity to methyltransferases | −2.2 | 0.67 | 7 |
| 71 | Rv2986c | hupB | DNA-binding protein II | −2.4 | 0.89 | 2 |
| 72 | Rv3135 | PPE50 | PPE-family protein | −2.0 | 0.55 | 6 |
| 73 | Rv3148 | nuoD | NADH dehydrogenase chain D | −2.4 | 0.87 | 7 |
| 74 | Rv3152 | nuoH | NADH dehydrogenase chain H | −2.2 | 0.64 | 7 |
| 75 | Rv3153 | nuoI | NADH dehydrogenase chain I | −3.6 | 1.00 | 7 |
| 76 | Rv3154 | nuoJ | NADH dehydrogenase chain J | −2.5 | 0.88 | 7 |
| 77 | Rv3377c | | similar to many cyclases involved in steroid biosynthesis | −2.2 | 0.73 | 7 |
| 78 | Rv3456c | rplQ | 50S ribosomal protein L17 | −3.3 | 1.00 | 2 |
| 79 | Rv3457c | rpoA | [alpha] subunit of RNA polymerase | −2.1 | 0.59 | 2 |
| 80 | Rv3460c | rpsM | 30S ribosomal protein S13 | −2.7 | 0.96 | 2 |
| 81 | Rv3461c | rpmJ | 50S ribosomal protein L36 | −2.5 | 0.78 | 2 |
| 82 | Rv3477 | PE31 | PE-family protein | −4.8 | 1.00 | 6 |
| 83 | Rv3478 | PPE60 | PPE-family protein | −4.1 | 1.00 | 6 |
| 84 | Rv3487c | lipF | probable esterase | −4.4 | 1.00 | 7 |
| 85 | Rv3600c | | conserved hypothetical protein | −2.1 | 0.63 | 10.5 |
| 86 | Rv3680 | | probable anion transporter | −2.3 | 0.80 | 3 |
| 87 | Rv3686c | | conserved hypothetical protein | −3.2 | 1.00 | 10.5 |
| 88 | Rv3763 | lpqH | 19 KD lipoprotein antigen precursor | −3.2 | 0.99 | 3 |
| 89 | Rv3783 | rfbD | integral membranememebrane protein, ABC-2 SUBFAMILY | −2.5 | 0.94 | 3 |

TABLE 11-continued

| No. Gene_ID | Product | Function_Class | Foldchange (Mutant/WT) | GG_PDE | Functional category |
|---|---|---|---|---|---|
| 90 Rv3806c | | possible integral membrane protein | −2.1 | 0.62 | 3 |
| 91 Rv3822 | | conserved hypothetical protein | −2.6 | 0.97 | 10.5 |
| 92 Rv3823c | mmpL8 | conserved large membrane protein | −4.0 | 1.00 | 3 |
| 93 Rv3824c | papA1 | PKS-associated protein, unknown function | −3.7 | 1.00 | 1 |
| 94 Rv3825c | pk52 | polyketide synthase | −2.2 | 0.70 | 1 |
| 95 Rv3921c | | unknown membrane protein | −4.5 | 1.00 | 3 |
| 96 Rv3922c | | possible hemolysin | −4.7 | 1.00 | 0 |
| 97 Rv3923c | rnpA | ribonuclease P protein component | −2.4 | 0.88 | 2 |
| 98 Rv3924c | rpmH | 50S ribosomal protein L34 | −3.0 | 0.99 | 2 |
| Negative Regulation | | | | | |
| 99 Rv0079 | | hypothetical protein | 3.7 | 1.00 | 16.6 |
| 100 Rv0129c | fbpC2 | antigen 85C, mycolytransferase | 2.7 | 0.53 | 1 |
| 101 Rv0188 | | putative methyltransferase | 6.4 | 1.00 | 3 |
| 102 Rv0211 | pckA | phosphoenolpyruvate carboxykinase | 3.8 | 1.00 | 7 |
| 103 Rv0233 | nrdB | ribonucleoside-diphosphate reductase B2 | 3.0 | 0.97 | 2 |
| 104 Rv0276 | | conserved hypothetical protein | 2.2 | 0.51 | 10.5 |
| 105 Rv0341 | | conserved hypothetical protein | 5.6 | 1.00 | 3 |
| 106 Rv0347 | | conserved hypothetical protein | 4.6 | 1.00 | 3 |
| 107 Rv0569 | | conserved hypothetical protein | 6.4 | 1.00 | 10.5 |
| 108 Rv0570 | nrdZ | ribonucleotide reductase, class II | 2.7 | 0.67 | 2 |
| 109 Rv0572c | | hypothetical protein | 2.1 | 0.01 | 16.6 |
| 110 Rv0677c | mmpS5 | conserved small membrane protein | 2.1 | 0.25 | 3 |
| 111 Rv0805 | | conserved hypothetical protein | 2.8 | 0.92 | 10.5 |
| 112 Rv0823c | ntrB | transcriptional regulator, ntrB (NifR3/Smm1 family) | 2.6 | 0.53 | 9 |
| 113 Rv0824c | desA1 | acyl-[ACP] desaturase | 2.7 | 0.17 | 1 |
| 114 Rv0885 | | unknown transmembrane protein | 3.0 | 0.98 | 10 |
| 115 Rv0967 | | conserved hypothetical protein | 2.2 | 0.43 | 10.5 |
| 116 Rv0968 | | conserved hypothetical protein | 2.0 | 0.27 | 10.5 |
| 117 Rv1303 | | conserved hypothetical protein | 2.3 | 0.45 | 3 |
| 118 Rv1304 | atpB | ATP synthase a chain | 2.4 | 0.64 | 7 |
| 119 Rv1332 | | putative transcriptional regulator | 2.0 | 0.18 | 9 |
| 120 Rv1461 | | conserved hypothetical protein | 2.1 | 0.10 | 10.5 |
| 121 Rv1577c | | phiRV1 possible prohead protease | 2.4 | 0.65 | 5 |
| 122 Rv1622c | cydB | cytochrome d ubiquinol oxidase subunit II | 12.1 | 1.00 | 7 |
| 123 Rv1623c | appC | cytochrome bd-II oxidase subunit I | 7.5 | 1.00 | 7 |
| 124 Rv1733c | | possible membrane protein | 2.8 | 0.77 | 3 |
| 125 Rv1737c | narK2 | nitrite extrusion protein | 2.2 | 0.12 | 3 |
| 126 Rv1738 | | conserved hypothetical protein | 2.9 | 0.17 | 10.5 |
| 127 Rv1813c | | conserved hypothetical protein | 9.6 | 1.00 | 10.5 |
| 128 Rv1846c | | putative transcriptional regulator | 2.4 | 0.70 | 9 |
| 129 Rv1894c | | some similarity to dioxygenases | 2.2 | 0.44 | 10.5 |
| 130 Rv1955 | | hypothetical protein | 2.5 | 0.79 | 16.6 |
| 131 Rv1996 | | conserved hypothetical protein | 12.7 | 1.00 | 10.5 |
| 132 Rv1997 | ctpF | probable cation transport ATPase | 3.4 | 1.00 | 3 |

TABLE 11-continued

| No. | Gene_ID | Product | Function_Class | Foldchange (Mutant/WT) | GG_PDE | Functional category |
|---|---|---|---|---|---|---|
| 133 | Rv2031c | hspX | 14 kD antigen, heat shock protein Hsp20 family | 2.5 | 0.04 | 2 |
| 134 | Rv2032 | acg | conserved hypothetical protein | 3.8 | 0.99 | 10.5 |
| 135 | Rv2160c | | hypothetical regulatory protein | 2.4 | 0.66 | 9 |
| 136 | Rv2193 | ctaE | cytochrome c oxidase polypeptide III | 2.3 | 0.04 | 7 |
| 137 | Rv2280 | | similar to D-lactate dehydrogenase | 2.2 | 0.30 | 7 |
| 138 | Rv2495c | pdhC | dihydrolipoamide acetyltransferase | 2.1 | 0.31 | 7 |
| 139 | Rv2497c | pdhA | pyruvate dehydrogenase E1 component [alpha] subunit | 2.5 | 0.70 | 7 |
| 140 | Rv2557 | | conserved hypothetical protein | 4.6 | 1.00 | 16.5 |
| 141 | Rv2623 | | conserved hypothetical protein | 7.1 | 1.00 | 10.5 |
| 142 | Rv2624c | | conserved hypothetical protein | 4.3 | 1.00 | 10.5 |
| 143 | Rv2625c | | conserved hypothetical protein | 5.8 | 1.00 | 3 |
| 144 | Rv2626c | | conserved hypothetical protein | 5.1 | 1.00 | 10.5 |
| 145 | Rv2627c | | conserved hypothetical protein | 11.5 | 1.00 | 10.5 |
| 146 | Rv2628 | | hypothetical protein | 15.0 | 1.00 | 16.6 |
| 147 | Rv2629 | | hypothetical protein | 4.0 | 1.00 | 10.5 |
| 148 | Rv2630 | | hypothetical protein | 2.0 | 0.27 | 16.6 |
| 149 | Rv2780 | ald | L-alanine dehydrogenase | 8.0 | 1.00 | 7 |
| 150 | Rv2846c | efpA | putative efflux protein | 2.4 | 0.47 | 3 |
| 151 | Rv3048c | nrdG | ribonucleoside-diphosphate small subunit | 2.5 | 0.77 | 2 |
| 152 | Rv3053c | nrdH | glutaredoxin electron transport component of NrdEF | 2.2 | 0.16 | 2 |
| 153 | Rv3127 | | conserved hypothetical protein | 5.3 | 1.00 | 10.5 |
| 154 | Rv3129 | | conserved hypothetical protein | 7.2 | 1.00 | 10.5 |
| 155 | Rv3130c | | conserved hypothetical protein | 4.4 | 0.99 | 10.5 |
| 156 | Rv3131 | | conserved hypothetical protein | 3.5 | 0.93 | 10.5 |
| 157 | Rv3139 | fadE24 | acyl-CoA dehydrogenase | 3.7 | 1.00 | 1 |
| 158 | Rv3140 | fadE23 | acyl-CoA dehydrogenase | 8.8 | 1.00 | 1 |
| 159 | Rv3230c | | similar to various oxygenases | 2.7 | 0.89 | 7 |
| 160 | Rv3675 | | hypothetical protein | 2.6 | 0.76 | 3 |
| 161 | Rv3841 | bfrB | bacterioferritin | 6.2 | 1.00 | 7 |
| 162 | Rv3842c | glpQ1 | glycerophosphoryl diester phosphodiesterase | 2.3 | 0.26 | 7 |
| 163 | Rv3854c | ethA | probable monooxygenase | 2.8 | 0.91 | 7 |

What is claimed is:

1. An immunogenic composition comprising a pharmaceutically acceptable carrier and an engineered attenuated *Mycobacterium tuberculosis* strain whose genome comprises a knockout mutation of gene rv0348.

2. A method of stimulating an immune response comprising administering to a mammal an immunogenic composition according to claim 1.

3. The immunogenic composition of claim 1, wherein the knockout mutation is an insertion of a heterologous sequence into the rv0348 gene.

4. The immunogenic composition of claim 1, wherein the knockout mutation is a deletion of a portion of the rv0348 gene.

5. The immunogenic composition of claim 4, wherein the knockout mutation is a deletion of at least 10% of the rv0348 gene.

6. The immunogenic composition of claim 5, wherein the knockout mutation is a deletion of at least 20% of the rv0348 gene.

7. The immunogenic composition of claim 6, wherein the knockout mutation is a deletion of at least 30% of the rv0348 gene.

8. The immunogenic composition of claim 1, wherein the knockout mutation is an engineered non-function copy of the wild-type rv0348 gene.

9. The immunogenic composition of claim 1, wherein the rv0348 gene is silent.

10. The immunogenic composition of claim 1, wherein the knockout mutation is a null-mutation and the rv0348 gene expresses a non-functional protein.

11. The immunogenic composition of claim 1, wherein the composition additionally comprises an adjuvant.

12. The immunogenic composition of claim 11, wherein the adjuvant is Fruend's incomplete adjuvant.

* * * * *